United States Patent [19]
Browne et al.

[11] Patent Number: 5,864,033
[45] Date of Patent: Jan. 26, 1999

[54] ADENOSINE KINASE INHIBITORS

[75] Inventors: Clinton E. Browne, Vista; Bheemarao G. Ugarkar, Escondido; Kevin M. Mullane, Del Mar; Harry E. Gruber; David A. Bullough, both of San Diego; Mark D. Erion, Del Mar; Angelo Castellino, San Diego, all of Calif.

[73] Assignee: Metabasis Therapeutics, Inc., San Diego, Calif.

[21] Appl. No.: 451,236

[22] Filed: May 26, 1995

Related U.S. Application Data

[60] Division of Ser. No. 812,916, Dec. 23, 1991, abandoned, which is a continuation-in-part of Ser. No. 647,117, Jan. 23, 1991, abandoned, which is a continuation-in-part of Ser. No. 466,979, Jan. 18, 1990, abandoned, which is a continuation-in-part of Ser. No. 408,707, Sep. 18, 1989, abandoned.

[51] Int. Cl.$^6$ ..................................................... C07H 19/16
[52] U.S. Cl. .................. 536/27.13; 536/27.1; 536/27.21; 536/27.6; 536/27.62; 536/27.7; 536/27.8; 536/27.81

[58] Field of Search .................................. 536/27.21, 27.6, 536/27.62, 27.8, 27.81, 27.13, 27.1, 27.7

[56] References Cited

U.S. PATENT DOCUMENTS 4,904,666 2/1990 Friebe et al. .

FOREIGN PATENT DOCUMENTS

| 0 496 617 A | 7/1992 | European Pat. Off. . |
| WO 94/17803 | 8/1994 | WIPO . |
| WO 94/18215 | 8/1994 | WIPO . |

*Primary Examiner*—James O. Wilson
*Attorney, Agent, or Firm*—Darby & Darby

[57] ABSTRACT

Novel compounds which selectively inhibit adenosine kinase and methods of preparing adenosine kinase inhibitors are provided. Also provided are methods of treating various conditions which may be ameliorated by increased local concentrations of adenosine using adenosine kinase inhibitors.

68 Claims, 12 Drawing Sheets

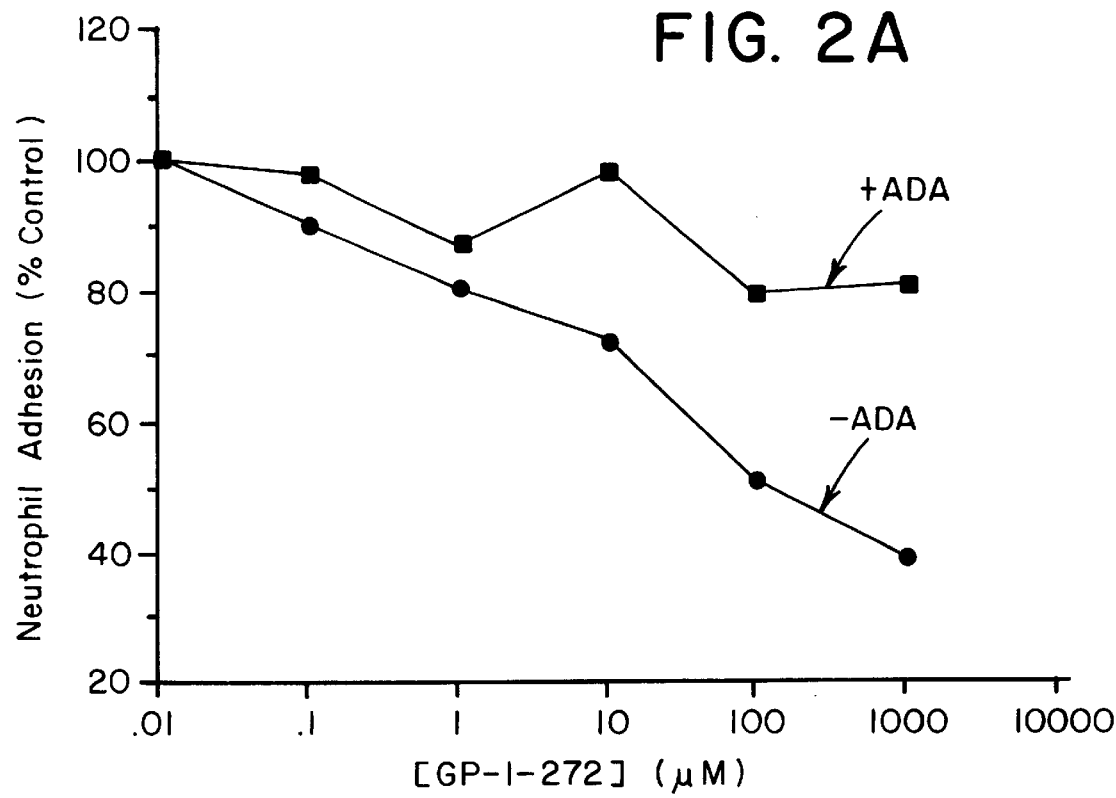
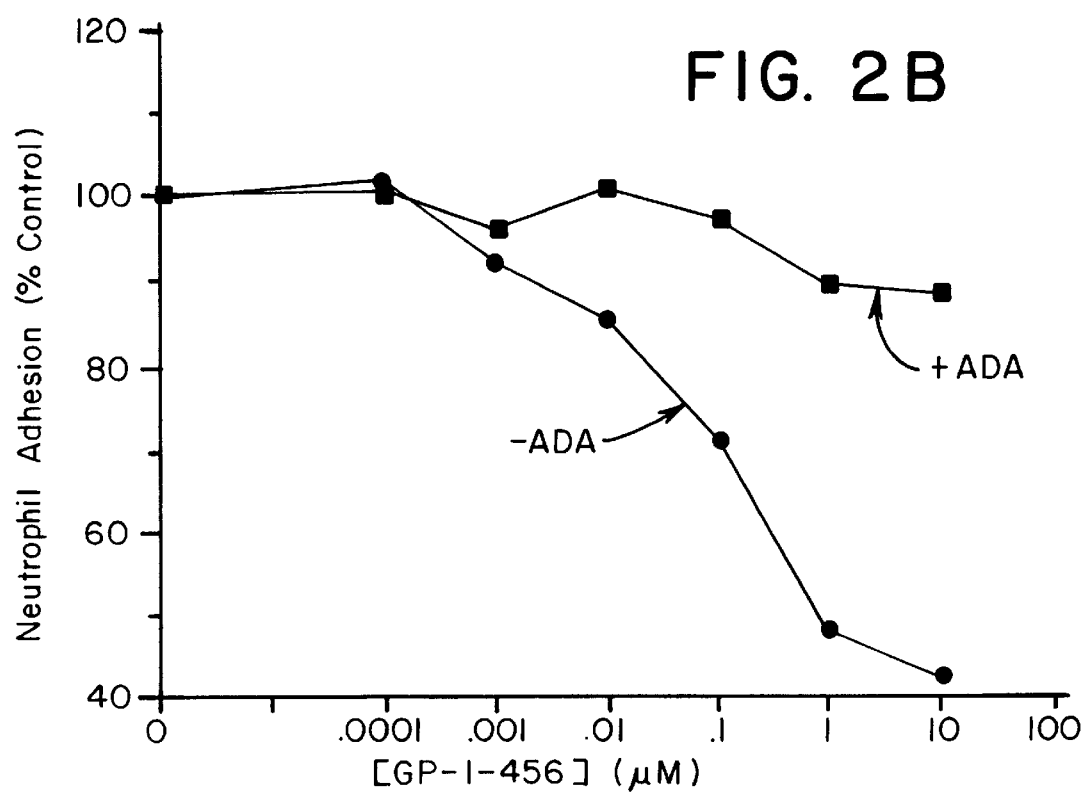

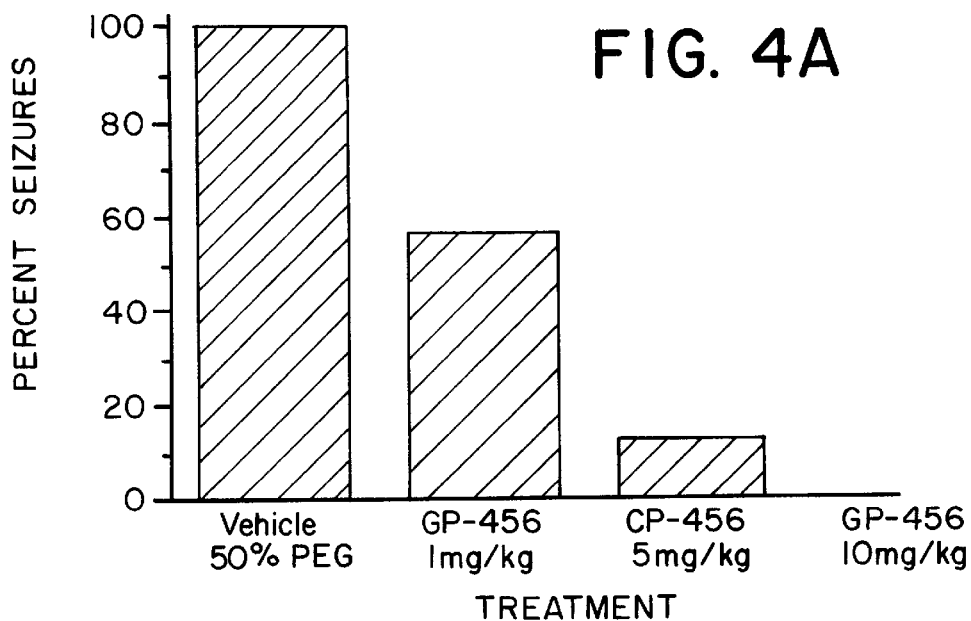
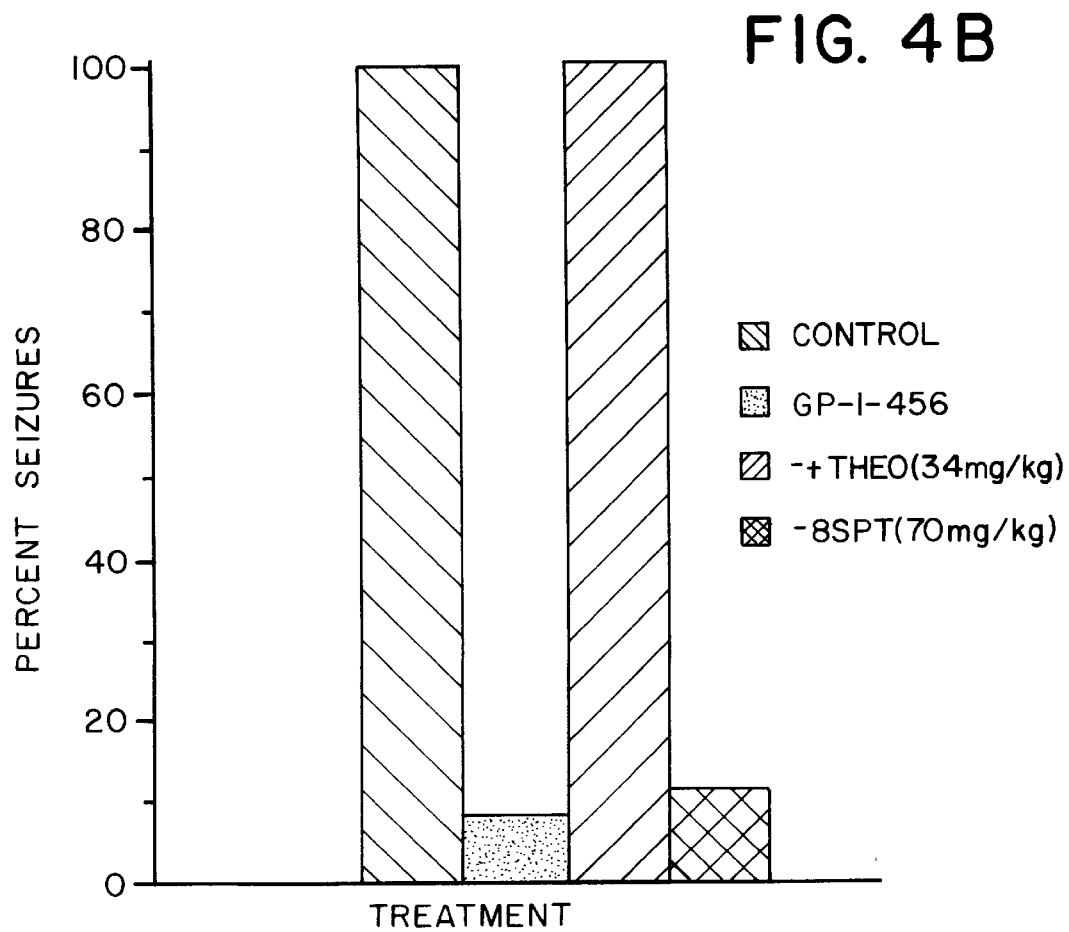

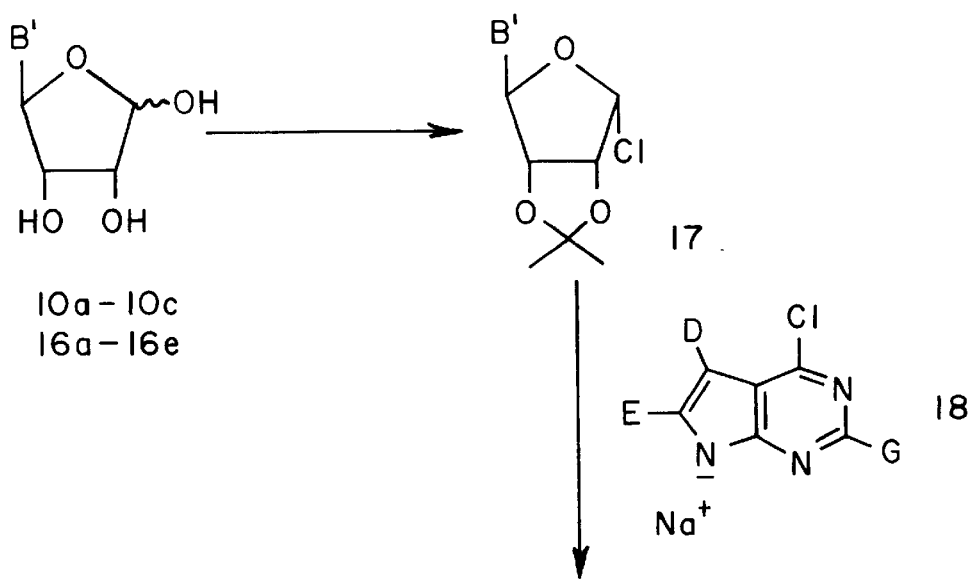
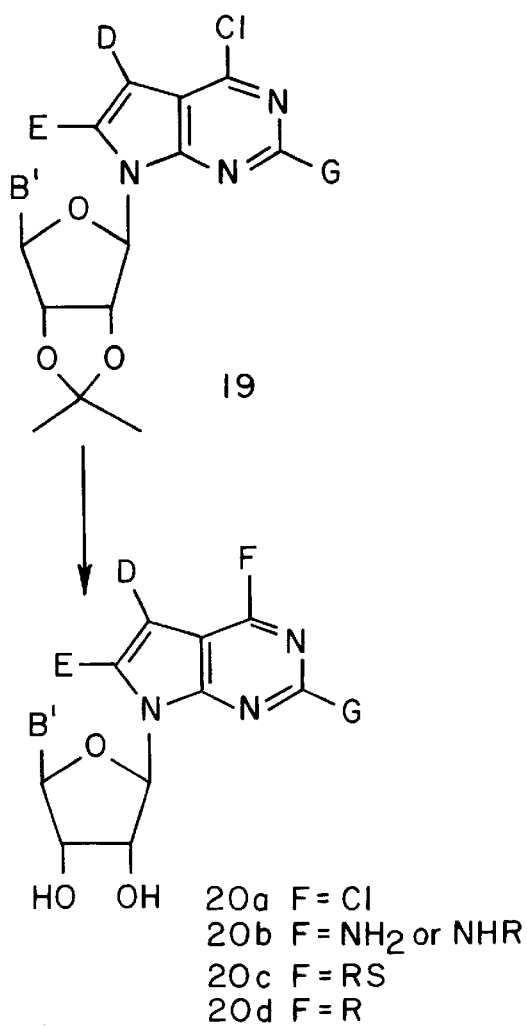
FIG. 8

24a F = O(H)
24b F = NH₂ or NHR
24c F = R

| B | D | E | F | G |
|---|---|---|---|---|
| $CH_3$ | Br | H | Cl | H |
| $CH_3$ | I | H | Cl | H |
| $CH_3$ | I | H | SH | H |
| $-CH_2-CH_3$ | Br | H | Cl | H |
| $-CH_2-CH_3$ | I | H | Cl | H |
| $-CH=CH_2$ | Br | H | Cl | H |
| $-CH=CH_2$ | I | H | Cl | H |
| $-CH_2-N_3$ | I | H | Cl | H |
| $-CH_2-CH_2-N_3$ | I | H | Cl | H |
| $-CH_2-N_3$ | Br | H | Cl | H |
| $CH_3$ | Br | H | HN-aryl | H |
| $CH_3$ | I | H | HN-aryl | H |
| $CH_2OH$ | I | H | HN-aryl | H |
| $CH_2OH$ | Br | H | HN-aryl | H |

ADENOSINE KINASE INHIBITORS

CROSS-REFERENCE TO RELATED APPLICATIONS

This application is a divisional application of Ser. No. 07/812,916 filed Dec. 23, 1991, now abandoned, which is a continuation-in-part of Ser. No. 07/647,117, filed Jan. 23, 1991, now abandoned; which is a continuation-in-part of Ser. No. 07/466,979, filed Jan. 18, 1990, now abandoned; which is a continuation-in-part of Ser. No. 07/408,707, filed Sep. 18, 1989, now abandoned; the disclosures of these applications are incorporated herein by reference.

FIELD OF INVENTION

This invention relates to adenosine kinase inhibitors and to novel nucleoside analogs, specifically to purine, pyrrolo [2,3-d] pyrimidine and pyrazolo[3,4-d]pyrimidine nucleoside analogs having activity as adenosine kinase inhibitors. The invention also relates to the preparation and use of these and other adenosine kinase inhibitors in the treatment of cardiovascular, and cerebrovascular diseases, inflammation and other diseases which can be regulated by increasing the local concentration of adenosine.

BACKGROUND OF THE INVENTION

Adenosine has been reported to have cardioprotective (Olafsson et al., *Circulation,* 1987, 76:1135–1145) and neuro-protective properties (Dragunow and Faull, *Trends in Pharmacol. Sci.,* 1988, 9:193; Marangos, *Medical Hypothesis,* 1990, 32:45). It is reportedly released from cells in response to alterations in the supply of or demand for oxygen (Schrader, *Circulation,* 1990, 81:389–391), is said to be a potent vasodilator, and is believed to be involved in the metabolic regulation of blood flow (Berne, *Circ. Res.,* 1980, 47:808–813). However, adenosine has a short half life (<1 sec) in human blood (Moser, et al., *Am. J. Physiol.,* 1989, 256:C799–C806), and therefore high doses of adenosine would need to be administered continuously to achieve effective levels. Adenosine has been reported to exhibit negative inotropic, chronotropic and dromotropic effects (Belardinelli et al., *Prog. in Cardiovasc. Diseases,* 1989, 32:73–97) and to cause coronary steal by preferentially dilating vessels in nonischemic regions. Consequently, high doses of adenosine are toxic and severely limit its therapeutic potential. However, it is believed that by increasing adenosine concentration locally, i.e. at the target site within the target tissue, the beneficial effects of adenosine can be provided without the toxic systemic effects.

Adenosine kinase is a cytosolic enzyme which catalyzes the phosphorylation of adenosine to AMP. Inhibition of adenosine kinase can potentially reduce the ability of the cell to utilize adenosine, leading to increased adenosine outside of the cell where it is pharmacologically active. However, the regulation of adenosine concentration is complex and involves other adenosine-metabolizing enzymes each with different kinetic properties and mechanisms of regulation. Adenosine can also be deaminated to inosine by adenosine deaminase (ADA) and condensed with L-homocysteine to S-adenosylhomocysteine (SAH) by SAH hydrolase. The role of each of these enzymes in modulating adenosine concentration is dependent on the prevailing physiological conditions, is tissue specific and is not well understood.

A number of nucleosides including purine, pyrrolo[2,3-d]pyrimidine and pyrazolo[3,4-d]pyrimidine analogs have been evaluated for inhibition of adenosine kinase but were reported to have $K_i$'s of greater than 800 nM (Caldwell and Henderson *Cancer Chemother. Rep.,* 1971 2:237–246; Miller et al., *J. Biol. Chem.,* 1979, 254:2346–2352). A few compounds have been reported as potent inhibitors of adenosine kinase with $K_i$'s of less than 100 nM. These are the purine nucleosides, 5'-amino-5'-deoxyadenosine (Miller et al., *J. Biol. Chem.,* 1979, 254:2346–2352) and 1,12-bis (adenosin-$N^6$-yl)dodecane (Prescott et al., *Nucleosides & Nucleotides,* 1989, 8:297), and the pyrrolopyrimidine nucleosides, 5-iodotubercidin (Henderson et al., *Cancer Chemotherapy Rep. Part 2,* 1972, 3:71–85; Bontemps et al., *Proc. Natl. Acad. Sci. USA,* 1983, 80:2829–2833; Davies et al., *Biochem. Pharmacol.,* 1986, 35:3021–3029) and 5'-deoxy-5-iodotubercidin (Davies et al., *Biochem. Pharmacol.,* 1984, 33:347–355; Davies et al., *Biochem. Pharmacol.,* 1986, 35:3021–3029).

Some of these compounds have been used to evaluate whether adenosine kinase inhibition might lead to increased extracellular adenosine concentrations. In rat cardiomyocytes, inhibition of adenosine deaminase by 2'-deoxycoformycin was reported to have no effect on adenosine release from the cells. In contrast, inhibition of ADA together with adenosine kinase by 5'-amino-5'-deoxyadenosine resulted in a 6-fold increase in adenosine release (Zoref-Shani et al., *J. Mol. Cell. Cardiol.,* 1988, 20:23–33). The effects of the adenosine kinase inhibitor alone were not reported. Similar results were reported in isolated guinea pig hearts; in these studies addition of 5'-amino-5'-deoxyadenosine to the perfusion medium, in the presence of EHNA to inhibit deamination, was reported to result in a 15-fold increase of adenosine release (Schrader in *Regulatory Function of Adenosine;* (Berne et al.) eds. pp. 133–156, 1983). These effects were not apparent in the absence of ADA inhibition and other studies using isolated rat hearts perfused with 5-iodotubercidin alone, have reported no increase in perfusate adenosine concentration under normoxic conditions (Newby et al., *Biochem. J.,* 1983, 214:317–323) or under hypoxic, anoxic or ischemic conditions (Achtenberg et al., *Biochem. J.,* 1986, 235:13–17). In other studies, adenosine release has been measured in neuroblastoma cells in culture and compared with that of a variant deficient in adenosine kinase (AK$^-$). The AK$^-$ cells used in this study were said to release adenosine at an accelerated rate; the concentration of adenosine in the growth medium was reported to be elevated compared to the normal cells (Green, *J. Supramol. Structure,* 1980, 13:175–182). In rat and guinea pig brain slices, adenosine uptake was reportedly inhibited by the adenosine kinase inhibitors, 5-iodotubercidin and 5'-deoxy-5-iodotubercidin (Davis et al., *Biochem. Pharmacol.,* 1984, 33:347–355). However, inhibition of uptake and intracellular trapping via phosphorylation does not necessarily result in increased extracellular adenosine, since the adenosine could enter other metabolio pathways or the percentage of adenosine being phosphorylated could be insignificant compared to the total adenosine removed The effects of adenosine and certain inhibitors of adenosine catabolism, including 5-iodotubericidin were evaluated in an experimental model in which dog hearts were subjected to ischemia and reperfusion; 5-iodotubericidin was reported to have inconsistent effects. (Wu, et al., *Cytobios,* 1987, 50:7–12).

Although the adenosine kinase inhibitors, 5'-amino-5'-deoxyadenosine and 5-iodotubercidin have been widely used in experimental models, the susceptibility of 5'-amino-5'-deoxyadenosine to deamination, and hence its potentially short half life, and the cytotoxicity of 5-iodotubercidin make their clinical utility limited and may limit interpretations based on these compounds. The pyrrolo[2,3-d]pyrimidines, 5-iodotubercidin and 5'-deoxy-5-iodotubercidin have been reported to cause pronounced general flaccidity and much-reduced spontaneous locomotor activity in mice, interpreted to be skeletal muscle relaxation; to cause hypothermia in mice; and to decrease blood pressure and heart rate in anesthetized rats (Daves et al., *Biochem. Pharmacol.*, 1984, 33:347–355; Daves et al., *Biochem. Pharmacol.*, 1986, 35:3021–3029; U.S. Pat. No. 4,455,420). The skeletal muscle effects of these compounds have been poorly documented, while the other effects were considered significant toxicities. It is believed that studies using these compounds were curtailed due to these toxicities and also because of their limited availability.

SUMMARY OF THE INVENTION

The present invention is directed to novel compounds which are potent and selective adenosine kinase inhibitors.

In one aspect, the present invention is directed to certain novel compounds which inhibit adenosine kinase, to the preparation of these compounds, and to the in vitro and in vivo adenosine kinase inhibition activity of these compounds. Another aspect of the present invention is directed to the clinical use of adenosine kinase inhibitors as a method of increasing adenosine concentrations in biological systems. In vivo inhibition of adenosine kinase prevents phosphorylation of adenosine resulting in higher local concentrations of endogenous adenosine. As a result of the very short half-life of adenosine and very low quantities of adenosine in tissues, this effect is most pronounced in regions producing the most adenosine such as ischemic regions. Hence, the beneficial effects of adenosine are enhanced in a site and event specific manner and toxic systemic effects are reduced.

In particular, in one preferred aspect, the present invention is directed to novel nucleoside analogs which comprise a 5'-modified ribose linked to a substituted purine, pyrrolo[2,3-d]pyrimidine, or pyrazolo[3,4-d]pyrimidine base. Certain preferred compounds within these groups possess potencies many times greater than previously described inhibitors of adenosine kinase. The compounds of the present invention possess advantages for pharmaceutical use such as enhanced pharmacological selectivity, efficacy, bioavailability, ease of manufacture and compound stability. This invention also discloses novel processes for the preparation of these compounds.

The novel compounds of the present invention and other adenosine kinase inhibitors may be used clinically to treat medical conditions where an increased localized adenosine concentration is beneficial. Accordingly, the present invention is directed to the prophylactic and affirmative treatment of ischemic conditions such as myocardial infarction, angina, percutaneous transluminal coronary angiography (PTCA), stroke, other thrombotic and embolic conditions, neurological conditions such as seizures and psychosis, and other conditions benefitted by enhanced adenosine levels such as inflammation, arthritis, autoimmune diseases, cardiac arrhythmias, ulcers and irritable bowel syndrome. These compounds are useful as muscle relaxants and also in inducing sleep and in treating anxiety.

The present invention is also directed to prodrugs and pharmaceutically acceptable salts of the compounds described herein and to pharmaceutical compositions suitable for different routes of drug administration and which comprise a therapeutically effective amount of an adenosine kinase inhibitor compound described herein admixed with a pharmacologically acceptable carrier.

Definitions

In accordance with the present invention and as used herein, the following terms, are defined with the following meanings, unless explicitly stated otherwise.

The term "hydrocarbyl" refers to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

The term "aryl" refers aromatic groups which have at least one ring having a conjugated pi electron system and includes carbocyclic aryl, heterocyclic aryl and biaryl groups, all of which may be optionally substituted.

Carbocyclic aryl groups are groups wherein the ring atoms on the aromatic ring are carbon atoms. Carbocyclic aryl groups include monocyclic carbocyclic aryl groups and optionally substituted naphthyl groups.

The term "monocyclic carbocyclic aryl" refers to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino or lower alkoxycarbonyl. "Optionally substituted naphthyl" refers to 1- or 2-naphthyl or 1- or 2-naphthyl preferably substituted by lower alkyl, lower alkoxy or halogen.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

Optionally substituted furanyl represents 2- or 3-furanyl or 2- or 3-furanyl preferably substituted by lower alkyl or halogen.

Optionally substituted pyridyl represents 2-, 3- or 4-pyridyl or 2-, 3- or 4-pyridyl preferably substituted by lower alkyl or halogen.

Optionally substituted thienyl represents 2- or 3-thienyl, or 2- or 3-thienyl preferably substituted by lower alkyl or halogen.

The term "biaryl" represents phenyl substituted by carbocyclic aryl or heterocyclic aryl as defined herein, ortho, meta or para to the point of attachment of the phenyl ring, advantageously para; biaryl is also represented as the —$C_6H_4$—Ar substituent where Ar is aryl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" refers to hydrocarbyl—CO— or HCO—.

The terms "acylamino" refers to RC(O)NCR)— and $(RCO)_2N$— respectively, wherein each R is independently hydrogen or hydrocarbyl.

The term "α-alkoxyalkylidene" refers to hydrocarbyl—O—CR (an orthoester) wherein R is hydrogen or hydrocarbyl.

The term "hydrocarbyloxycarbonyloxy" refers to the group ROC(O)O— wherein R is hydrocarbyl.

The term "lower carboalkoxymethyl" or "lower hydrocarbyloxycarbonymethyl" refers to hydrocarbyl—OC(O)CH$_2$— with the hydrocarbyl group containing ten or less carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "halogen" refers to fluorine, chlorine, bromine or iodine.

The term "hydrocarbyloxycarbonylamino" refers to a urethane, hydrocarbyl—O—CONR— wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methine" refers to

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

The term "prodrug" as used herein refers to any compound that has less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein as examples. The groups illustrated are exemplary, not exhaustive and one skilled in the art could prepare other known varieties of prodrugs. Such prodrugs of the compounds of Formula I, fall within the scope of the present invention.

The term "pharmaceutically acceptable salt" includes salts of compounds of Formula I derived from the combination of a compound of this invention and an organic or inorganic acid. The compounds of Formula I are useful in both free base and salt form. In practice the use of salt form amounts to use of base form; both forms are within the scope of the present invention.

BRIEF DESCRIPTION OF THE DRAWINGS

FIGS. 2A and 2B depict the dose-dependent inhibition of neutrophil adhesion to endothelial cells by the adenosine kinase inhibitors GP-1-272 and GP-1-456 respectively and the reversal of these inhibitions by co-treatment with adenosine deaminase ("ADA").

FIG. 4A depicts the dose-dependent inhibition of pentylenetetrazole (PTZ) induced seizures by the adenosine kinase inhibitor GP-1-456, and FIG. 4B depicts the reversal of this inhibition by the central adenosine receptor antagonist theophylline but not the peripheral antagonist 8-sulfophenyltheophylline.

FIG. 8 depicts the overall process for preparign 5-modified pyrrolo[2,3]pyrimidine riboside compounds of Formula I.

DETAILED DESCRIPTION OF THE INVENTION

NOVEL ADENOSINE KINASE INHIBITORS

Figure 1A:
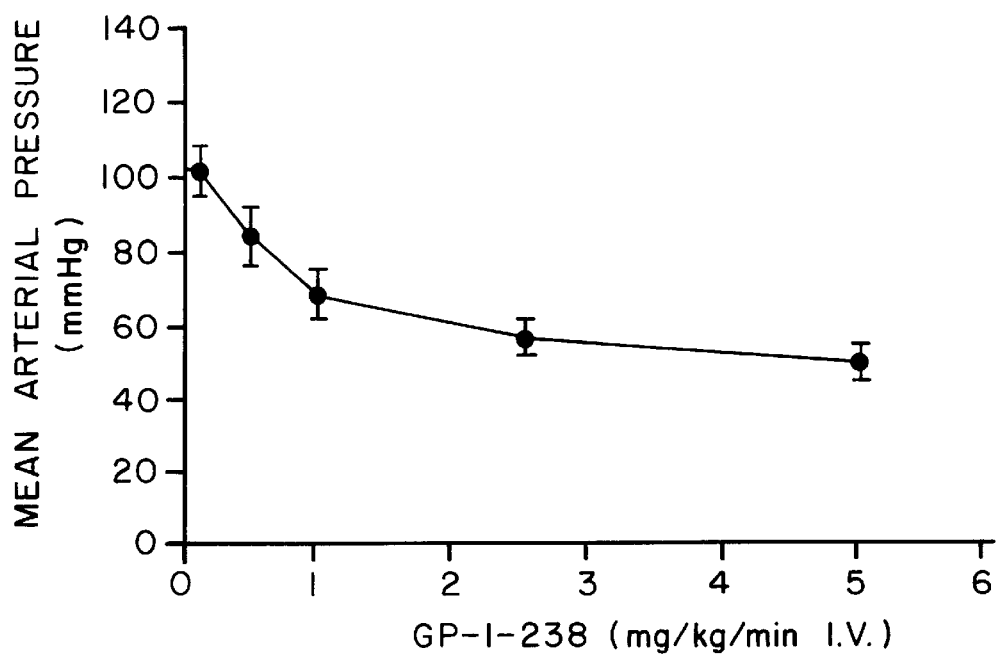
FIGS. 1A and 1B depict the effects of the adenosine kinase inhibitor GP-1-238 on mean arterial pressure following intravenous administration to anesthetized and conscious rats, respectively.
Figure 1B:
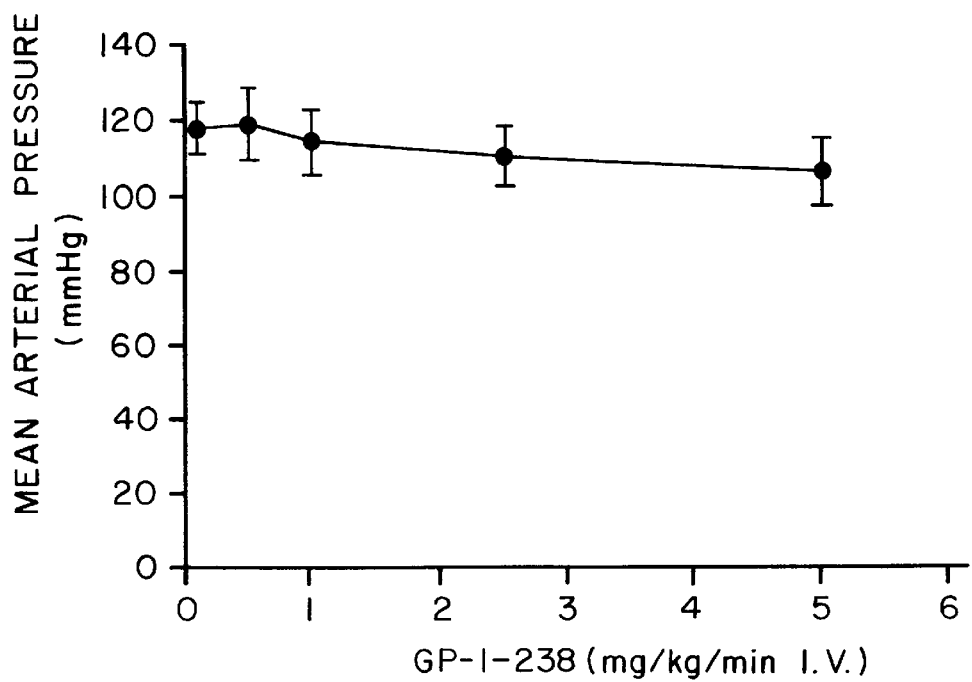
Figure 1C:
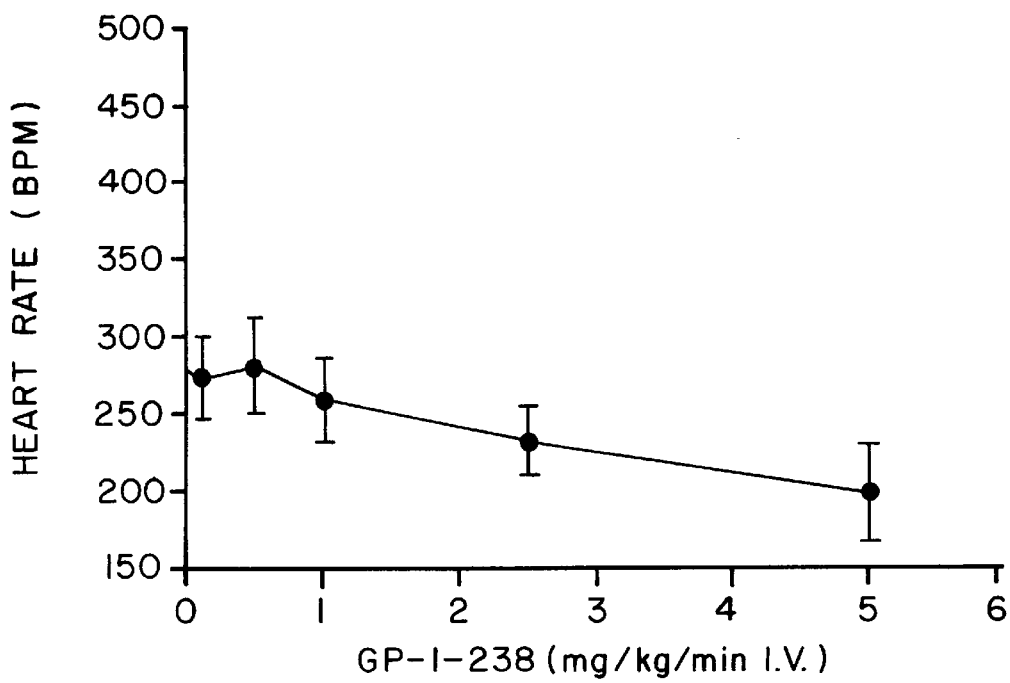
FIGS. 1C and 1D depict the effects of the adenosine kinase inhibitor GP-1-238 on heart rate following intravenous administration to anesthetized and conscious rats, respectively.
Figure 1D:
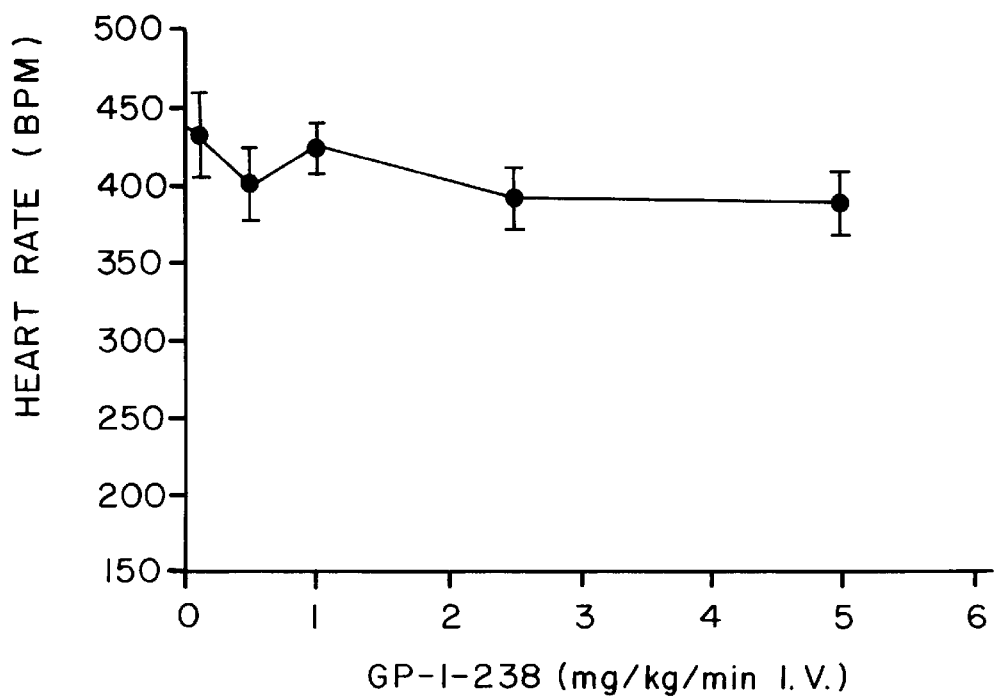
Figure 1E:
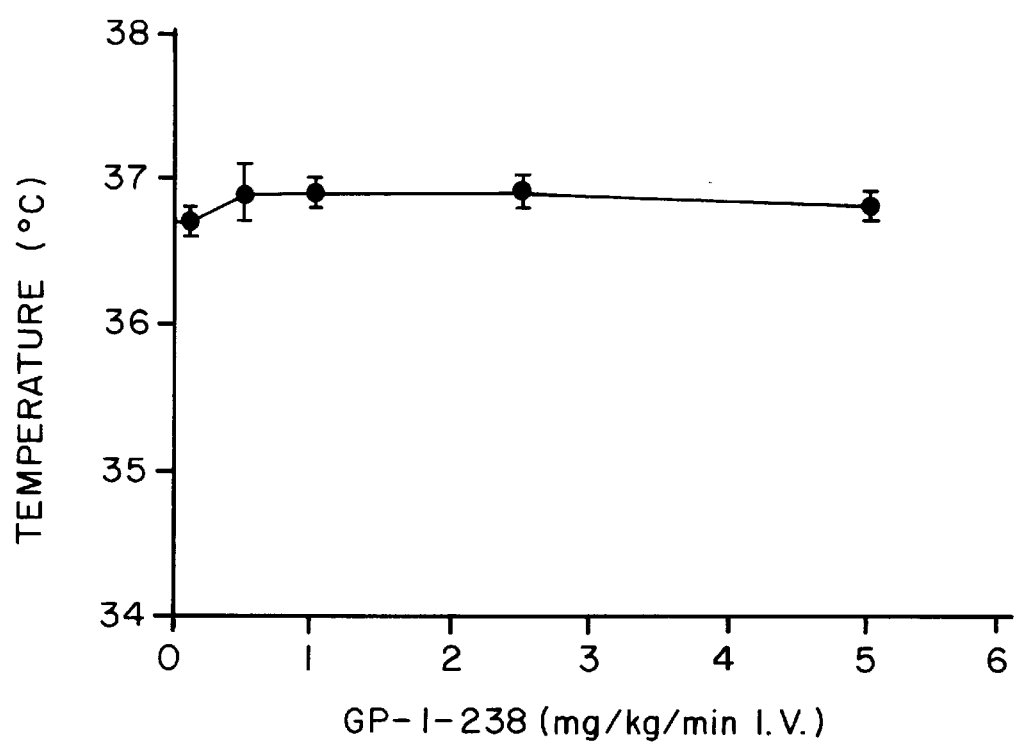
FIGS. 1E and 1F depict the effects of the adenosine kinase inhibitor GP-1-238 on body temperature following intravenous administration to anesthetized and conscious rats, respectively.
Figure 1F:
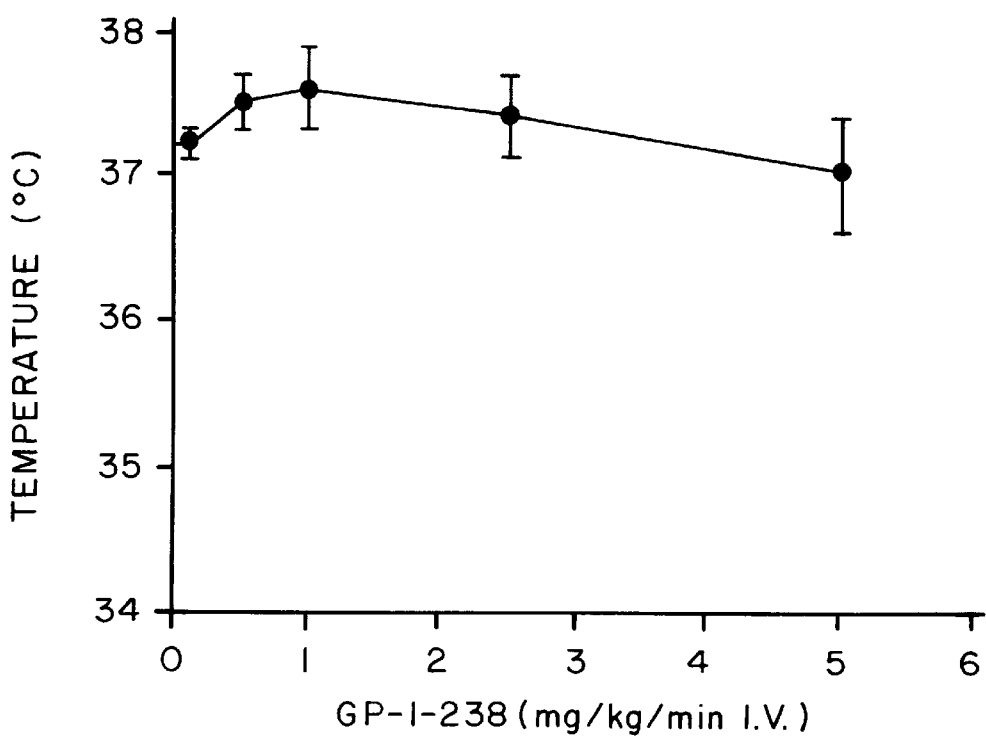

The present invention relates to novel adenosine kinase inhibitors which comprise compounds of the general formula I.

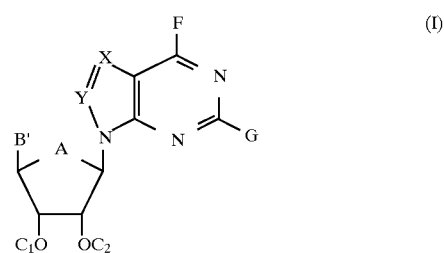

wherein:

(a) A is oxygen, methylene or sulfur;

(b) B' is —(CH$_2$)$_n$—B wherein n is 1, 2, 3 or 4 and B is hydrogen, alkyl, alkoxy, amino, alkylamino, acylamino, hydrocarbyloxycarbonylamino, mercapto, alkylthio, azido, cyano, halogen, or B' is alkenyl or alkynyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is

and Y is —N= or

(e) D is hydrogen, halogen, alkyl, aryl, aralkyl, alkenyl, alkynyl, haloalkyl, cyano, cyanoalkyl, acyl, carboxamido, a carboxylic acid or carboxylic acid ester group, alkoxy, aryloxy, aralkyloxy, alkylthio, arylthio, aralkylthio, amino, alkylamino arylamino, aralkylamino, acylamino, or nitro;

(f) E is hydrogen, halogen, alkyl, or alkylthio;

(g) F is alkyl, aryl, aralkyl, halogen, amino, alkylamino, arylamino, aralkylamino, cyano, cyanoalkyl, alkoxy, aryloxy, aralkoxy, alkylthio, arylthio, aralkylthio; optionally substituted indolinyl or indolyl; pyrrolidinyl or piperazinyli and (h) G is hydrogen, halogen, lower alkyl, lower alkoxy, lower alkylamino or lower alkylthio; and pharmaceutically acceptable salts thereof; with the proviso that: when A is oxygen and (i) X is

and Y is

then if B' is methyl, D is halogen, cyano or carboxamido, F is amino, then G is not hydrogen; or if D is hydrogen, then F is not amino; or (ii) X is

and Y is —N=, if B is hydrogen or halogen, D and G are hydrogen, then F is not amino;
or when A is methylene, X is

Y is

B, D, E and G are hydrogen, then F is not amino.

According to an alternative aspect of the present invention, novel adenosine kinase inhibitors are provided which have a 5'-group which comprises a hydroxyl or hydroxyl derivative. However, it is believed due to their overall structures, those compounds which have a 5'-hydroxyl would not act as substrates for phosphorylation enzymes and, thus, would be unlikely to undergo 5'-phosphorylation or would be phosphorylated at an extremely slow rate.

One preferred group of these adenosine kinase inhibitors comprise compounds of the formula:

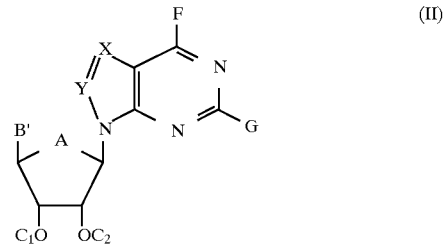

(II)

wherein:

(a) A is oxygen, methylene or sulfur;

(b) B' is —(CH$_2$)$_n$B wherein n is 1, 2, 3 or 4 and B is hydroxy, acyloxy, hydrocarbyloxycarbonyloxy, or —OCONR$_2$ wherein R is independently hydrocarbyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is

and Y is —N=;

(e) D is halogen, aryl or aralkyl;

(f) F is alkyl, aryl, aralkyl, halogen, amino, alkylamino, arylamino, aralkylamino, cyano, cyanoalkyl, alkoxy, aryloxy, aralkoxy, alkylthio, arylthio, aralkylthio, optionally substituted indolinyl or indolyl, pyrrolidinyl or piperazinyl; and (g) G is hydrogen, halogen, lower alkyl, lower alkoxy, or lower alkylthio; and pharmaceutically acceptable salts thereof; with the proviso that when A is oxygen and D is halogen, then F is not amino.

Another preferred group of these adenosine kinase inhibitors comprise compounds of the formula:

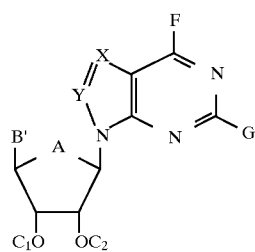

(III)

wherein:

(a) A is oxygen, methylene or sulfur;

(b) B' is —(CH$_2$)$_n$B wherein n is 1, 2, 3 or 4 and B is hydroxy, acyloxy, hydrocarbyloxycarbonyloxy, or —OCONR$_2$ wherein R is hydrocarbyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is

and Y is

(e) D is aryl or aralkyl;

(f) E is hydrogen, halogen, alkyl, or alkylthio;

(g) F is alkyl, aryl, aralkyl, halogen, amino, alkylamino, arylamino, aralkylamino, cyano, cyanoalkyl, alkoxy, aryloxy, aralkyloxy, alkylthio, arylthio, aralkylthio, optionally substituted indolinyl or indolyl, pyrrolidinyl or piperazinyl; and (h) G is hydrogen, halogen, lower alkyl, lower alkoxy, or lower alkylthio; and pharmaceutically acceptable salts thereof; with the proviso that: when A is oxygen, D is oxadiazolyl, triazolyl or triazinyl, E and G are both hydrogen, then F is not amino.

Also included within the present invention are adenosine kinase inhibitors which comprise modified purine nucleosides of the formula:

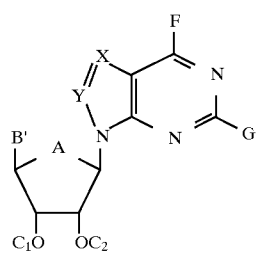

(IV)

wherein (a) A is oxygen, methylene or sulfur;

(b) B' is —CH$_2$B wherein and B is amino, alkylamino, or acylamino;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is —N= and Y is

(e) E is hydrogen, halogen, alkyl, amino, alkylamino, azido, acylamino, alkoxy or alkylthio;

(f) F is halogen, amino, alkylamino, arylamino, aralkylamino, cyanoalkyl, alkoxy, aryloxy, aralkoxy, alkylthio, arylthio, aralkylthio, alkyl, aryl, aralkyl, optionally substituted indolinyl or indolyl, pyrrolidinyl or piperazinyl; and (g) G is hydrogen, halogen, lower alkyl, lower alkoxy, or lower alkylthio and pharmaceutical acceptable salts thereof; with the proviso that:

when A is oxygen, B is amino or hydrocarbylamino, E and G are hydrogen, then F is not amino.

According to a further aspect of the present invention, novel adenosine kinase inhibitors are provided that comprise dimeric compounds of the formula:

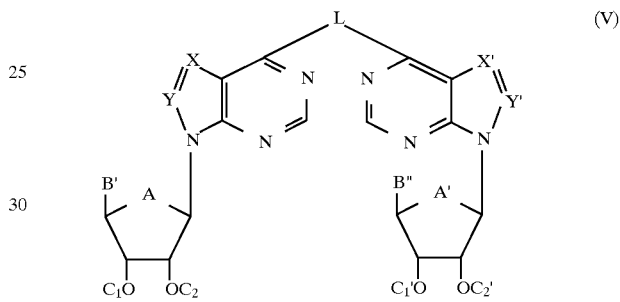

(V)

wherein (a) A and A' are independently oxygen, methylene or sulfur;

(b) B' and B" are independently —(CH$_2$)$_n$B wherein n is independently 1, 2, 3 or 4 and B is independently hydrogen, hydroxy, alkyl, alkoxy, amino, alkylamino, acylamino, hydrocarbyloxycarbonylamino, mercapto, alkylthio, azido, or either or both of B' or B" is independently alkenyl or alkynyl;

(c) C$_1$ and C$_1$' and C$_2$ and C$_2$' are each independently hydrogen, acyl, hydrocarbyloxycarbonyl, or C$_1$ and C$_2$ or C$_1$' and C$_2$' taken together form a 5-membered ring wherein C$_1$ or C$_1$' is a single bond to C$_2$ or C$_2$' and C$_2$ or C$_2$' is carbonyl or α-alkoxyalkylidene;

(d) X and X' are each independently

or —N=; and Y and Y' are each independently —N= or

provided that either of and X and Y or X' and Y' are not both —N=;

(e) D is independently hydrogen, halogen, alkyl, aryl, aralkyl, alkenyl, alkynyl, haloalkyl, cyano, cyanoalkyl, acyl, carboxamido, a carboxylic acid or corresponding carboxylic acid ester group, alkoxy, aryloxy, aralkyloxy, alkylthio, arylthio, aralkylthio, amino, alkylamino, arylamino, aralkylamino acylamino or nitro;

(f) E is independently hydrogen, halogen, alkyl, or alkylthio;

(g) L is an optionally substituted piperazinyl divalent radical or —NH(ALKL)NH— wherein ALKL is a divalent alkylene radical of 2 to 24 carbon atoms; and (h) G and G' are each independently hydrogen, halogen, lower alkyl, lower alkoxy, or lower alkoxy; or pharmaceutically acceptable salts thereof; with the proviso that if B is OH, then X and X' are not both —N=.

In general, preferred are compounds where G is hydrogen, halogen, alkyl or alkylthio. Especially preferred G groups include hydrogen. Preferred $C_1$ and $C_2$ groups include hydrogen and acetyl.

Preferred E groups include hydrogen or halogen, especially preferred are compounds where E is hydrogen.

Preferred are compounds where A is oxygen.

Preferred are compounds where D is hydrogen, halogen, alkyl, aryl, aralkyl, alkenyl or alkynyl, cyano, cyanoalkyl, alkoxy, aryloxy, aralkoxy, alkylthio, arylthio, aralkylthio, amino, alkylamino, arylamino, aralkylamino, carboxamido, or hydrocarbyloxycarbonyl. Especially preferred D groups include hydrogen, halogen, alkyl, aryl, aralkyl, cyano, alkoxy, aryloxy, aralkoxy, alkenyl or alkynyl, more preferably hydrogen, halogen, aryl, cyano, alkoxy or aryloxy. A particularly preferred group of compounds include those wherein D is hydrogen, halogen or aryl. According to one preferred aspect, D is aryl such as heterocyclic aryl or monocyclic carbocyclic aryl, such as optionally substituted phenyl.

Preferred compounds include those where B' is —(CH$_2$)$_n$B, and n is 1 or 2, more preferably n is 1. B may preferably include hydrogen, halogen, alkyl, amino, alkylamino, alkoxy, mercapto, alkylthio, azido or cyano; more preferably B is hydrogen, halogen, lower alkyl, amino, lower alkylamino, azido or cyano. Particularly preferred B groups include hydrogen, amino or azido. Also preferred are compounds wherein B' is vinyl, ethynyl, or propargyl.

Preferred F groups include halogen, amino, alkylamino, arylamino, aralkylamino, alkylthio, arylthio, alkyl, aryl or aralkyl, more preferably amino or arylamino. Especially, preferred F groups include optionally substituted anilino.

A. Preferred Compounds

The compounds of the present invention contain asymmetric carbon atoms and hence can exist as stereoisomers, both enantiomers and diastereomers. The individual preferred stereoisomers and mixtures thereof are considered to fall within the scope of the present invention. The compounds described by Formula I contain a 5-modified 1-β-D-ribofuranosyl group and that isomer comprises a particularly preferred diastereomeric and enantiomeric form for compounds of the present invention. Aptly, the synthetic examples cited herein provide the most preferred isomer. It is evident that in addition to the sugar moiety, additional asymmetric carbons may be present in compounds of Formula I, being present in moieties B', $C_1$ or $C_2$ or the substituted heterocyclic purine, pyrrolo[2,3-d]pyrimidine or pyrazolo[3,4-d]pyrimidine ring. In this event, both of the resulting diastereomers are considered to fall within the scope of the present invention.

It is noted that compounds of formula I where B is hydroxy (i.e. a 5'-hydroxyl moiety) are in many cases potent inhibitors of adenosine kinase. The use of compounds having formula I wherein B' replaced by —CH$_2$OH, as adenosine kinase inhibitors are included in the scope of this invention. However, since some of these compounds may be phosphorylated in vivo and since the resulting 5'-phosphates may be toxic, mutagenic or teratogenic, 5'-hydroxy compounds which can serve as substrates for phosphorylation enzymes may not comprise preferred compounds for clinical or therapeutic use. An important aspect of the novel compounds of the present invention is that these preferred compounds are either non-phosphorylatable at the 5' position or are not substrates of enzymes that lead to phosphorylation.

(i) Preferred Pyrazolo[3,4-d]pyrimidines

Preferred adenosine kinase inhibitor compounds of the present invention include certain pyrazolo[3,4-d]pyrimidine compounds of Formulas I and II.

Preferred pyrazolo[3,4-d]pyrimidine compounds of Formula I include those where G is hydrogen and A is oxygen. Preferred D groups include hydrogen, alkyl, aryl, aralkyl, cyano, alkoxy, aryloxy, aralkoxy, alkenyl or alkynyl, more preferably hydrogen, halogen, aryl, cyano, alkoxy or aryloxy, more particularly hydrogen, halogen or aryl. An especially preferred group of compounds includes those where D is aryl, especially heterocyclic aryl or monocyclic carbocyclic aryl, more preferably optionally substituted phenyl. Preferred B' groups include —(CH$_2$)$_n$B wherein B is hydrogen, halogen, alkyl, amino, alkylamino, alkoxy, mercapto, alkylthio, azido or cyano; more preferably B is hydrogen, halogen, lower alkyl, amino, lower alkylamino, azido or cyano. Particularly preferred B groups include hydrogen, amino or azido. Preferably, n is 1 or 2, more preferably 1. Other preferred B' groups include vinyl and ethynyl. Preferred are compounds of formula I wherein F is halogen, amino, alkylamino, arylamino, aralkylamino, alkylthio, arylthio, alkyl, aryl or aralkyl, more preferably amino or arylamino. Certain preferred compounds include F groups which comprise optionally substituted anilino.

Examples of preferred pyrazolo[3,4-d]pyrimidine compounds include those noted as GP-1-515, GP-1-547, GP-1-560, GP-1-665, GP-1-666 GP-1-667, GP-1-695, and GP-1-704.

Preferred pyrazolo[3,4-d]pyrimidine compounds of Formula II include those where G is hydrogen and A is oxygen. Preferred D groups include aryl. Preferred aryl groups include heterocyclic carbocyclic aryl groups, especially optionally substituted phenyl. Preferred F groups include halogen, amino, alkylamino, arylainino, aralkylamino, alkylthio, arylthio, alkyl, aryl, or aralkyl, more preferably amino or arylamino. Certain preferred compounds of Formula II may include F groups which comprise optionally substituted anilino groups.

(ii) Preferred Pyrrolo[2,3-d]pyrimidines

Preferred adenosine kinase compounds of the present invention include pyrrolo[2,3-d]pyrimidine compounds of Formulas I and II.

Preferred pyrrolo[2,3-d]pyrimidine compounds of Formula I include those wherein G is hydrogen. Preferred are compounds wherein E is hydrogen or halogen; more preferably E is hydrogen. Preferred are compounds where A is oxygen. Preferred compounds include those where D is hydrogen, halogen, alkyl, aryl, aralkyl, cyano, alkenyl or alkynyl, more preferably hydrogen, halogen or aryl. An especially preferred group of compounds includes those where D is aryl, especially heterocyclic aryl or monocyclic carbocyclic aryl, especially optionally substituted phenyl. Preferred B' groups include —(CH$_2$)$_n$B wherein n is 1 or 2, preferably 1. Preferably, B is hydrogen, halogen, alkyl, amino, alkylamino, alkoxy, mercapto, alkylthio, azido or cyano, more preferably B is hydrogen, halogen, lower alkyl, amino, lower alkylamino, lower alkoxy, lower alkylthio, or azido, more particularly hydrogen, lower alkyl, amino, lower alkylamino, or azido. Especially preferred B groups include hydrogen, amino or azido. Other preferred B' groups include vinyl and ethynyl. Preferred pyrrolo[2,3-d] pyrimidine compounds of Formula I include those wherein F is halogen, amino, alkylamino, arylamino, aralkylamino, alkylthio, aralkylthio, alkyl, aryl or aralkyl, more preferably amino or arylamino. Certain preferred compounds include F groups which comprise optionally substituted anilino. Examples of preferred pyrrolo[2,3-d]pyrimidine compounds include those noted as GP-1-448, GP-1-606, GP-1-608, GP-1-639, GP-1-683, GP-1-684, GP-1-691, GP-1-711, GP-1-714, and GP-1-718.

Preferred pyrrolo[2,3-d]pyrimidines of Formula II include those where G is hydrogen and A is oxygen. Preferably E is hydrogen or halogen, more preferably hydrogen. Preferred D groups include aryl. Preferred aryl groups include heterocyclic aryl groups and monocyclic carbocyclic aryl groups, especially optionally substituted phenyl. Preferred heterocyclic aryl groups include 2-furanyl, 2-thienyl and 3-thienyl.

(iii) Preferred Purines

Preferred purine compounds include those where G is hydrogen, halogen, lower alkyl or lower alkylthio, more preferably hydrogen. Preferred are compounds wherein A is oxygen. Preferred E groups include hydrogen, halogen or alkylthio. Preferred are compounds wherein B is amino. Preferred F groups include halogen, amino, alkylamino, arylamino, aralkylamino, alkylthio, arylthio, alkyl, aryl or aralkyl, more preferably amino or arylamino.

(iv) Preferred Dimer Compounds

Preferred dimeric compounds include those which comprises dimers of the above-described pyrazolo[3,4-d] pyrimidines, the pyrrolo[2,3-d]-pyrimidines and purines. These dimers may comprise monomeric units which are the same or different.

SYNTHESIS OF PREFERRED COMPOUNDS

A. General Synthetic Methods

The present invention also directed to processes for preparing compounds of Formula I. Disclosed herein are general synthetic routes for preparing variously substituted purine nucleosides or pyrrolo[2,3-d]pyrimidine nucleosides, including a novel and improved synthesis of 5'-deoxy-5-iodotubercidin; and pyrazolo[3,4-d]pyrimidine nucleosides of the present invention.

Figure 5:
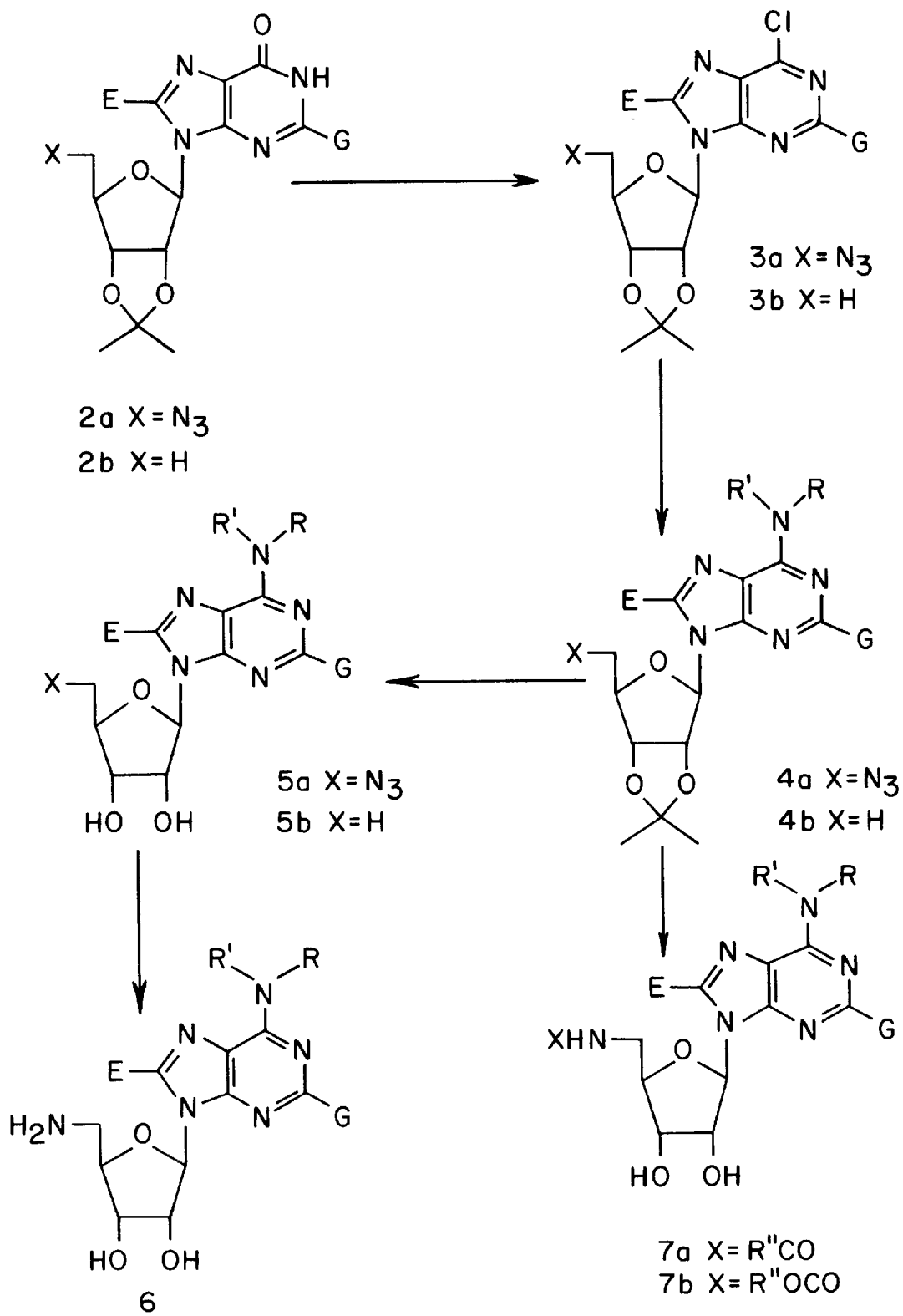
FIG. 5 depicts a process for preparing 5'-azido, 5'-amino and 5'-deoxy analogs of N$^6$-substituted purine ribosides.

A process for preparing 5'-azido, 5'-amino and 5'-deoxy analogs of $N^6$-substituted purine ribosides is depicted in FIG. 5. The protected azide (2a), prepared from 2',3'-O-isopropylideneinosine, is activated for nucleophilic attack at position six by chlorination with thionyl chloride/dimethylformamide. Other standard reagents may also be used to activate position six of 2 such as thionyl bromide, phosphorous oxychloride, triphenylphosphine dibromide-thiophenol-potassium permanganate or hexamethyldisilazane-ammonium sulfate. The chloride (3) or other activated intermediate (Br, $RSO_2$, $R_3SiO$, etc.) is then reacted with ammonia or an appropriate amine such as aniline, piperazine or indoline in solvents such as water, alcohols, THF and the like. The resulting protected $N^6$-substituted azide (4a) is deblocked using an aqueous acid such as 50% formic acid, to provide the $N^6$-substituted 5'-azido-5'-deoxyadenosine (5a). Reduction of the azide (5a) to the amine (6) is effected by catalytic hydrogenation with a catalyst such as platinum oxide, palladium on carbon and the like. For molecules containing other functional groups sensitive to hydrogenation, triphenylphosphine is used to selectively reduce the azide moiety to the amine. To prepare the N-acylamino (7a) and hydrocarbyloxycarbonylamino (7b) compounds, the azide 4a is reduced to the amine and treated with an acyl anhydride or acyl chloride or alkyl chloroformate and deblocked to give (7a) or (7b) respectively. Analogous processes are used to prepare the 2- and 8-substituted analogs beginning with appropriately substituted intermediates. An alternative synthesis of 5'-amino and 5'-hydrocarbylamino compounds comprises deblocking a 2',3'-isopropylidene-5'-tosylate with aqueous acid and then reacting the deblocked tosylate with ammonia or a lower hydrocarbylamine. Further description of these procedures is set forth in the Examples.

A similar process is used to prepare 5'-deoxy purine nucleosides. The appropriately substituted 5'-deoxy-2',3'-O-isopropylideneinosine (2b) is chlorinated or activated using other reagents described above, aminated to 4b and subsequently deblocked to afford the 5'-deoxy nucleoside 5b.

The overall process for preparing 5'-modified pyrrolo[2,3-d]pyrimidine riboside compounds of Formula I, is depicted in FIG. 8. A key step comprises the sodium salt glycosylation method (K. Ramasamy et al., *Tetrahedron Letters*, 1987, 28:5107) using the anion of a substituted 4-chloropyrrolo[2,3-d]pyrimidine (18) and 1-chloro-2,3-O-isopropylidene-5-O-tert-butyldimethylsilyl-α-D-ribofuranoside (17). This method is also suitable for direct preparation of ribofuranosides wherein the 5-hydroxy group has been replaced with substituents such as hydrogen or azido or extended with additional carbons (FIG. 8). The azide sugars further provide for facile synthesis of 5'-amino nucleosides by reductions of the azide function after ribosylation. An alternative to the sodium salt glycosylation method is a solid-liquid phase transfer reaction using the same substrates and potassium hydroxide in place of sodium hydride as described by Rosemeyer H., and Seela, F, *Helvetica Chimica Acta*, 1988, 71:1573.

Figure 6:
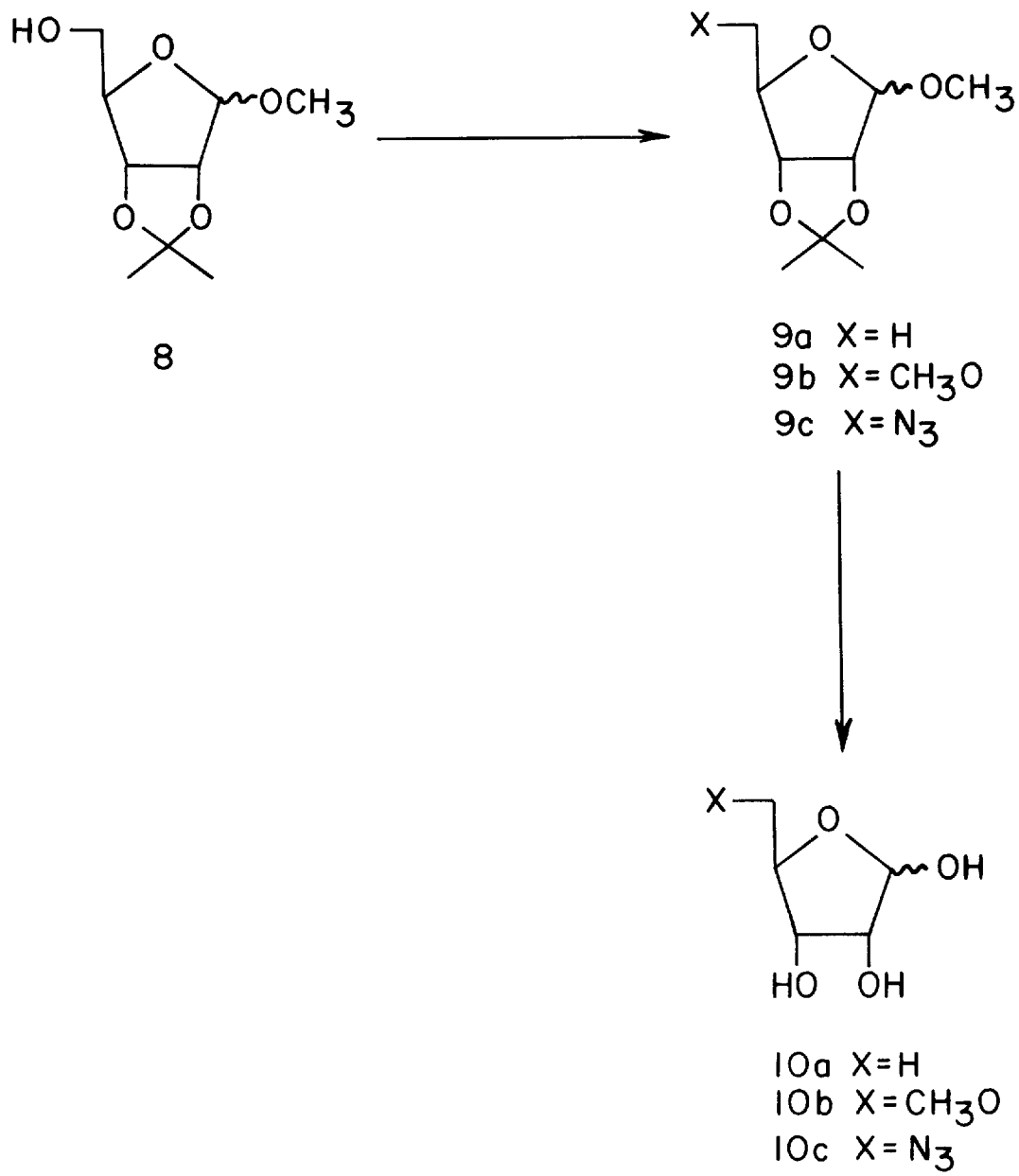
FIG. 6 depicts a process for modification of ribose sugars at the 5-position.
Figure 7:
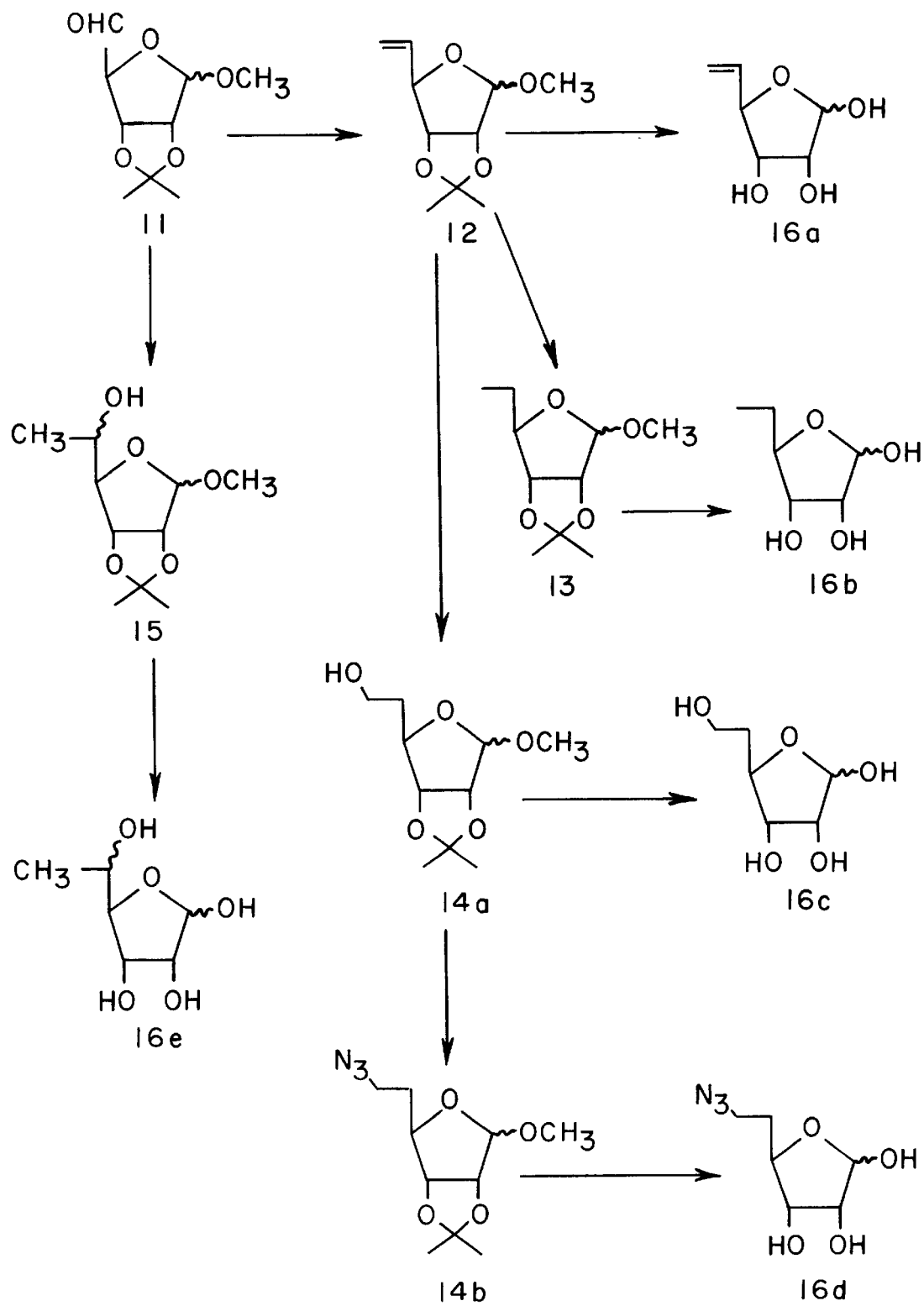
FIG. 7 depicts processes for homoloogation of ribose sugars at the 5-position.

Preparation of the 5-substituted ribose analogs and homologs is outlined in FIGS. 6 and 7. The 5-substituted-5-deoxy ribose analogs 10 are prepared by tosylation of the protected ribose 8, displacement of the tosylate by appropriate nucleophiles and subsequent deblocking (Synder, J.; Serianni, A.; *Carbohydrate Res.*, 1987, 163: 169). The ribose homologs (FIG. 7) are prepared by oxidation of the protected ribose (8) to the aldehyde (11) (Moorman, A.; Borchaedt, R.; *Nucleic Acid Chemistry-Part III*, Townsend, L.; Tipson, R.; John Wiley & Sons, 1986). The aldehyde is homologated via the appropriate Wittig reagent to give the key intermediate protected vinyl sugar (12). The protected intermediate is deblocked to give the vinyl ribose homolog (16a) or reduced to (13) and then deblocked to give the saturated deoxy analog (16b). Alternatively, the vinylated intermediate (12) is hydroborated and oxidized affording the protected homologous ribose (14a) which is deblocked to the ribose homolog or converted to the azide (14b) via tosylation and displacement with azide. Deblocking of (14b) then affords the homologous azido ribose (16d). The protected 5-aldehyde (11) was also methylated to ultimately afford 6-deoxy-D-allofuranose (16e). The various 5- substituted riboses are then converted to the corresponding 2,3-O-isopropylidine ketals (FIG. 8) which are chlorinated stereoselectively to 5-modified 1-chloro-α-D-ribofuranosides (17) using carbon tetrachloride and hexamethylphosphorous triamide (Wilcox, C.; Otaski, R.; *Tetrahedron Lett.*, 1986, 27:1011).

The preparation of various substituted 4-chloro-pyrrolo [2,3-d]pyrimidines is described in the Examples. The initial products from the ribosylation reactions, ribosyl protected 5-substituted-4-chloropyrrolo[2,3-d]pyrimidine nucleosides and the corresponding deblocked compounds are versatile intermediates and comprise an aspect of the present invention. As examples, the 4-chloro substituent of 19 can be displaced by sulfur (such as thiourea or mercaptide anions) leading to thionated and hydrocarbylthio compounds. More importantly, displacement of the 4-chloro substituent by ammonia or amines leads to 4-amino- and 4-arylaminopyrrolo[2,3-d]pyrimidine nucleosides. As further example, and an aspect of the present invention, an improved synthesis of the adenosine kinase inhibitor, 5'deoxy-5-iodotubercidin is described. According to this novel method, coupling of the sodium salt of 4-chloro-5-iodopyrrolo[2,3-d]pyrimidine with 1-chloro-5-deoxy-2,3-isopropylidene-α-D-ribofuranoside (17, B'=CH$_3$) in acetonitrile gives the protected 4-chloro compound. Amination of this product with ammonia, followed by deblocking affords 5'-deoxy-5-iodotubercidin.

Especially preferred intermediates are protected pyrrolo [2,3-d]pyrimidine nucleosides having a 4-chloro and a 5-iodo or bromo substituent.

Another aspect of the present invention is directed to the use of arylboronic acids to prepare 4- and 5-arylated pyrrolo [2,3-d]pyrimidine bases and nucleosides from the corresponding 4- and 5-halogenated compounds. Thus, a halogenated nucleoside such as 19 or the corresponding base was heated with an arylboronic acid and a palladium-phosphine catalyst such as palladium tetrakis(triphenylphospliine) to prepare the analogous arylated compound by displacement of halogen. Various 4- and 5- arylated pyrrolo[2,3-d] pyrimidines also can be prepared using arylstannyl compounds in place of the arylboronic acids (Flynn, B.; Macolino, B.; Crisp, G. *Nucleosides & Nucleosides*, 1991, 10:763). Synthesis of 5-arylpyrrolo[2,3-d]pyrimidines can also be effected by condensation of arylamino ketones and malononitrile to arylated pyrroles and subsequent ring closure to 5-arylpyrrolo[2,3-d]pyrimidines. (Taylor, E.; Hendess, R., *J. Am. Chem. Soc.*, 1965, 87:1995).

The various above-mentioned products of ribosylation reactions may be deblocked at appropriate points with aqueous acids such as 50% formic acid or trifluoroacetic acid. Preparation of 5'-amino compounds consists of reducing an appropriate azide. The 5'-amides and urethanes are prepared analogously to those described previously for purine analogs. Further description of these procedures is set forth in the Examples.

Figure 9:
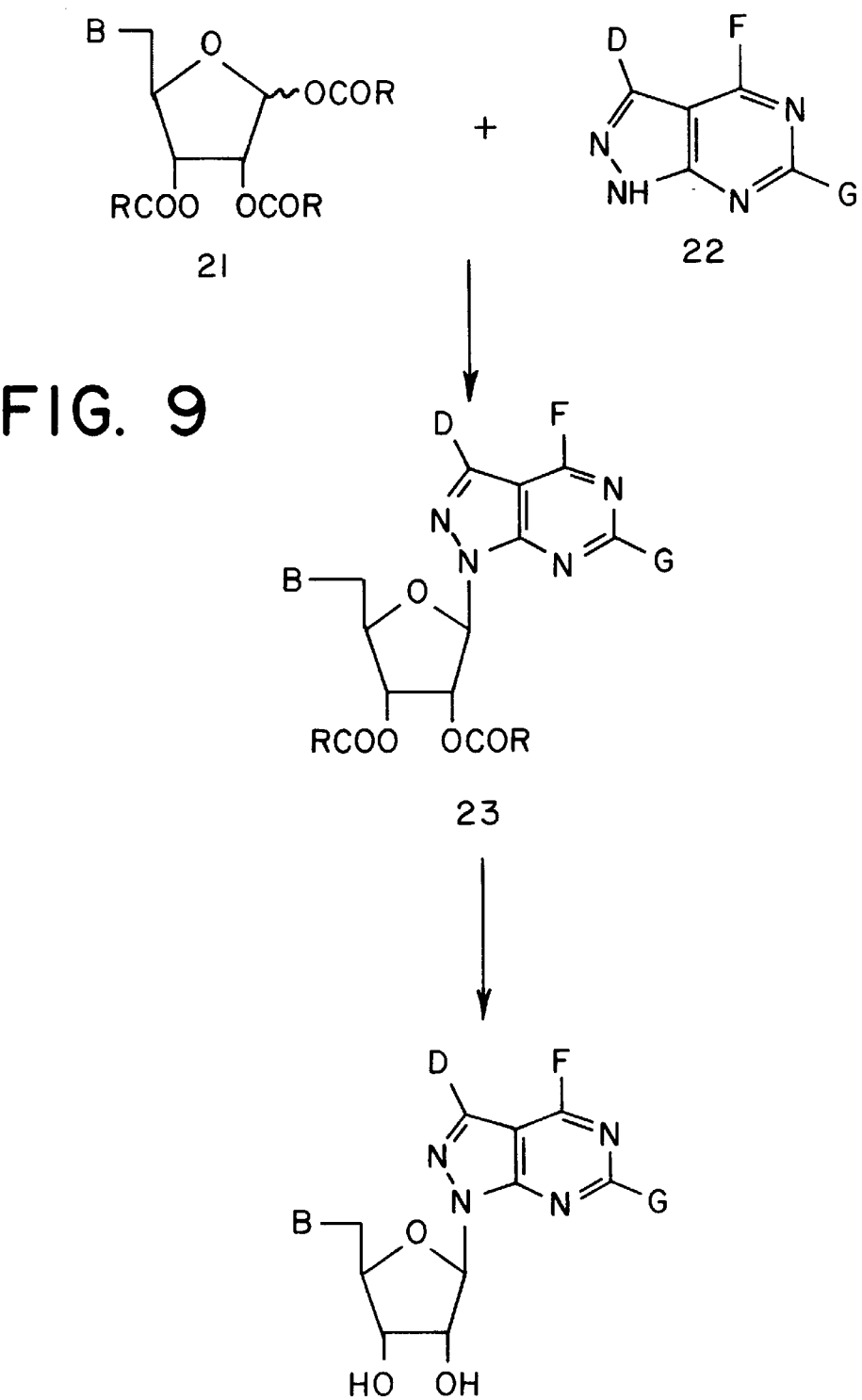
FIG. 9 depicts a process for the synthesis of 5'-substituted pyrazolo[3,4-d]pyrimidine ribosides of Formula I.

Still another aspect of this invention is the preparation of 5'-substituted pyrazolo[3,4-d]pyrimidine ribosides of Formula I as depicted in FIG. 9. Accordingly, a substituted pyrazolo[3,4-d]pyrimidine is ribosylated with an esterified 5-hydroxy, 5-azido or 5-deoxyribofuranoside in the presence of a Lewis acid such as boron trifluoride (Cottam, H., Petrie, C.; McKernan, P.; Goebel, R.; Dalley, N.; Davidson, R.; Robins, R.; Revankar, G.; *J. Med. Chem.*, 1984, 27:1120). The 5-substituted sugar is prepared by esterification of the deblocked sugar 10a to 10c or 16a to 16e (See FIGS. 6 and 7). Suitable esters include the acetate, benzoate, toluate, anisoate and the like. The substituted pyrazolo[3,4-d] pyrimidine base (22) may be prepared by a variety of procedures as illustrated in the Examples. Two general routes to the compounds of the present invention are described below.

The first general route comprises coupling an esterified ribose (21), prepared from 10 or 16, with a 3-substituted pyrazolo[3,4-d]pyrimidin-4-one. After ribosylation the pyrimidone riboside (24a) may be activated by chlorination with thionyl chloride/dimethylformamide or other reagents previously described and then reacted with ammonia or an amine to provide a variety of substituted 5'-modified N$^4$-substituted-amino-pyrazolo[3,4-d]pyrimidine nucleosides (24b). Examples of this aspect of the invention, 3-iodopyrazolo[3,4-d]pyrimidone nucleosides, are prepared by nonaqueous diazotization-iodination of the 3-amino compounds using a nitrite ester such as isoamyl nitrite and methylene iodide. Previous attempts to diazotize the 3-aminopyrazolo[3,4-d]pyrimidones using aqueous nitrous acid gave only N-nitrosated pyrazolo[3,4-d]pyrimidin-3,4-diones (Cottam, H.; Petrie, C.; McKernan, P.; Goebel, R.; Dalley, N.; Davidson, R.; Robins, R.; Revankar, G.; *J. Med. Chem.*, 1984, 27:1119). Further modifications of 23 or 24 include reduction of the 5'-azido moiety to afford the 5'-amino compounds or the 5'-amides and urethanes as described in FIG. 5. Ester prodrugs (C$_1$ and C$_2$) of various 5'-amino nucleosides are prepared by reduction of the 5'-azide esters (23) using previously described reagents.

Various C-4 alkylated pyrazolo[3,4-d]pyrimidine nucleosides are prepared by reaction of the above mentioned suitably protected 4-chloropyrazolo[3,4-d]pyrimidine nucleosides with carbanion nucleophiles. A specific catalyst for this alkylation reaction was found to be trimethylamine; these reactions either do not occur or proceed very slowly and in poor yield in the absence of trimethylamine. Suitable carbanions include those derived from diethyl malonate, ethyl cyanoacetate, malononitrile, nitromethane, cyanide salts and the like. This procedure is also used to prepare C-6 alkylated purine ribosides. The initial C-alkylated products were deblocked and optionally further modified by hydrolysis and decarboxylation to afford the desired products.

An alternative process for synthesis of 5'-azido- and 5'-amino-5'-deoxypyrazolo[3,4-d]pyrimidine ribosides is also described. Accordingly, a substituted allopurinol riboside (24a) is protected by conversion to the 2',3'-isopropylidene derivative, tosylated and reacted with sodium azide in DMSO or DMF to form the azide. Activation of position four by chlorination with thionyl chloride/dimethylformamide or other reagents as described, followed by displacement of the activating group by ammonia or an amine results in a protected 5'-azido-5'-deoxy riboside. The azide is deblocked to afford (24b, B=N$_3$) and subsequently reduced to the 5'-amino riboside using the previously described procedures.

The second general route for preparation of substituted pyrazolo[3,4-d]pyrimidine nucleosides comprises coupling the esterified ribose (21) with various substituted 4-amino or 4-hydrocarbylaminopyrazolo[3,4-d]pyrimidines. The resulting products are then further modified or deblocked to afford the desired compounds. The utility of this procedure is demonstrated in the Examples, by the preparation of 3-phenyl-4-(phenylamino)pyrazolo[3,4-d]pyrimidine 5'-modified ribosides from 3-phenyl-4-(phenylamino) pyrazolo[3,4-d]pyrimidine and various 5'-modified sugars. In another aspect of the present invention, halogenated pyrazolo[3,4]pyrimidine ribosides can be arylated using arylboronic acids and palladium catalysts as described for the pyrrolo[2,3-d]pyrimidines. Alternatively, the base can be boronated and then coupled with an aryl halide. Further description of these procedures is set forth in the Examples.

B. Preferred Methods of Synthesis

According to another aspect of the present invention, certain preferred methods of preparing the adenosine kinase inhibiting compounds of Formula I are provided.

One preferred method of the present invention is a novel procedure for preparing C-6 alkylated purine nucleosides and C-4 alkylated pyrazolo[3,4-d]pyrimidine nucleosides from the 6-chloropurine and 4-chloropyrazolo[3,4-d] pyrimidine nucleosides, respectively, using various carbanions (enolates, cyanide anion, etc.) and trimethylamine as a specific catalyst. Previous methodology for C-alkylation of 6-chloropurines consisted of a multistep route involving alkylthiolation and oxidation to a sulfone followed by nucleophilic displacement with a carbanion (Yame, A.; Matsuda, A.; Veda,4T.; Chem. Pharm. Bull. (Jap.), 1980, 28:150). This multistep route can be accomplished in one step using the specific catalyst trimethylamine which reacts to form a quaternary salt and in turn is displaced by a carbanion in situ, regenerating trimethylamine. The reactions are specifically catalyzed by unhindered trialkylamines.

Another preferred method of the present invention is a process for preparing arylated bases and nucleosides by reaction of a halogenated pyrrolo[2,3-d]pyrimidine or pyrazolo[3,4-d]pyrimidine with an aryl boronic acid in the presence of a palladium-phosphine catalyst. In this process, the halogen atom of a brominated or preferably, iodinated pyrrolo[2,3-d]pyrimidine or pyrazolo[3,4-d]pyrimidine base or nucleoside, is replaced by an aryl moiety such as phenyl, substituted phenyl or a heteroaryl moiety such as furanyl. A catalyst consisting of a metal such as palladium, complexed to an arylphosphine such as triphenylphosphine must be present as well as a base such as sodium carbonate. The resulting arylated nucleosides are important examples of the present invention and this method is shorter and more versatile than alternative syntheses of arylated nucleosides.

Still another preferred method of the present invention is a process for preparing the previously unknown 3-iodo- and 3-chloropyrazolo[3,4-d]pyrimidine nucleoside by nonaqueous diazotization of 3-aminopyrazolo[3,4-d]pyrimidine nucleosides. According to this invention, a suitably substituted 3-aminopyrazolo[3,4-d]pyrimidine nucleoside is diazotized by heating with an alkyl nitrite such as isoamyl nitrite in the presence of an iodine source (such as methylene iodide) resulting in replacement of the 3-amino moiety with an iodine atom. Alternatively, methylene iodide can be replaced by a chlorine source such as carbon tetrachloride resulting in replacement of the amino moiety by a chlorine atom. A previously reported attempt to effect replacement of the amino moiety in a 3-aminopyrazolo[3,4-d]pyrimidine riboside with other moieties using nitrous acid resulted only in replacement of the amino moiety by a hydroxyl group. The resulting 3-chloro- and particularly 3-iodopyrazolo[3,4-d]pyrimidine nucleoside are an important subject of adenosine kinase inhibitors disclosed in the present invention.

C. Preferred Intermediates

According to a further aspect of the present invention, certain novel intermediates are provided which are useful in the synthesis of the adenosine kinase inhibitors of the present invention.

(i) Intermediates for Pyrrolo[2,3-d]pyrimidines

Certain intermediates useful in the preparation of certain preferred adenosine kinase inhibitors which comprise substituted pyrrolo[2,3-d]pyrimidine nucleosides include compounds of the formula:

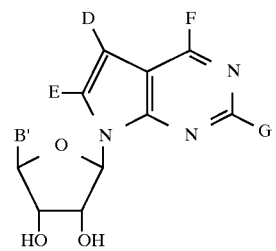

Figure 10:
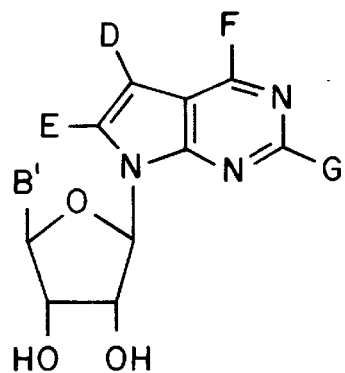
FIG. 10 depicts the structures of certain preferred intermediates useful in the synthesis of adenosine kinase inhibitors.

(VI)

wherein B' is lower alkyl or 1 to 3 carbon atoms optionally substituted with azido or hydroxy, or lower alkenyl of 1 to 3 carbon atoms; D is bromo or iodo, E is hydrogen, F is chloro, mercapto, arylamino and G is hydrogen. Certain especially preferred intermediates are set forth in FIG. 10.

These preferred intermediates include the following compounds:

5-Bromo-4-chloro-7-(5-deoxy-1-β-D-ribofuranosyl) pyrrolo[2,3-d]pyrimidine;
4-Chloro-5-iodo-7-(5-deoxy-1-β-D-ribofuranosyl) pyrrolo-[2,3-d]pyrimidine;
5-Iodo-7-(5-deoxy-1-β-D-ribofuranosyl)pyrrolo[2,3-d]-pyrimidin-4(3H)-thione;
5-Bromo-4-chloro-7-(5,6-dideoxy-1)-β-D-allo-furanosyl)pyrrolo[2,3-d]pyrimidine;
4-Chloro-5-iodo-7-(5,6-dideoxy-1-β-D-ribofuranosyl) pyrrolo-[2,3-d]pyrimidine;
5-Bromo-4-chloro-7-(5,6-dideoxy-5,6-didehydro-1-β-D-allofuranosyl)pyrrolo[2,3-d]pyrimidine;
4-Chloro-5-iodo-7-(5,6-dideoxy-5,6-didehydro-1-β-D-allofuranosyl)pyrrolo[2,3-d]pyrimidine;
4-Chloro-5-iodo-7-(5-azido-5-deoxy-1-β-D-ribofuranosyl)pyrrolo[2,3-d]pyrimidine;
5-Bromo-4-chloro-7-(5-azido-5-deoxy-1-β-D-ribofuranosyl)pyrrolo[2,3-d]pyrimidine;
4-Chloro-5-iodo-7-(6-azido-5,6-dideoxy-1-β-D-allofuranosyl)pyrrolo[2,3-d]pyrimidine;
5-Bromo-4-arylamino-7-(5-deoxy-1-β-D-ribofuranosyl) pyrrolo[2,3-d]pyrimidine;
5-Iodo-4-arylamino-7-(5-deoxy-1-β-D-ribofuranosyl) pyrrolo[2, 3-d]pyrimidine;
5-Iodo-4-arylamino-7-(1-β-D-ribofuranosyl)pyrrolo[2,3-d]pyrimidine; and
5-Bromo-4-arylamino-7-(1-β-D-ribofuranosyl)pyrrolo[2, 3-d]pyrimidine.

In addition to being useful in the preparation of certain preferred adenosine kinase inhibitors, certain of these preferred intermediates exhibit activity as adenosine kinase inhibitors themselves.

(ii) Intermediates for Pyrazolo[3,4-d]pyrimidines

Certain intermediates useful in the preparation of certain preferred adenosine kinase inhibitor compounds comprise substituted pyrazolo[3,4-d]pyrimidines of the formula:

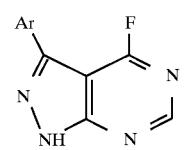

(VI)

wherein Ar is an aryl group and F is halogen, preferably chloro. Preferred aryl groups include heterocyclic aryl groups and monocyclic carbocyclic aryl groups, including optionally substituted phenyl groups. These preferred intermediates include the following compounds:

4-chloro-3-phenylpyrazolo[3,4-d]pyrimidine;
4-chloro-3-(2-thienyl)pyrazolo[3,4-d]pyrimidine;

4-chloro-3-(4-methoxyphenyl)pyrazolo[3,4-d]pyrimidine; and 4-chloro-3-(4-chlorophenyl)pyrazolo[3,4-d]pyrimidine.

UTILITY

The adenosine kinase inhibitors of the present invention may be used in the treatment of a variety of clinical situations where increasing local levels of adenosine are beneficial. In particular, these compounds may be used in treating cardiovascular disorders in which injury or dysfunction is caused by ischemia and/or reperfusion (following a period of ischemia). These include (1) heart attack, a situation that arises from obstruction of one or more of the coronary arteries supplying blood to the heart muscle, and which, if prolonged, leads to irreversible tissue damage; (2) angina pectoris, a clinical condition in which the blood supply to the heart is sufficient to meet the normal needs of the heart but insufficient when the needs of the heart increase (e.g. during exercise), and/or when the blood supply becomes more limited (e.g. during coronary artery spasm); (3) unstable angina associated with pain at rest; and (4) silent ischemia. In each of these conditions, treatment with adenosine kinase inhibitors will increase local levels of adenosine, and thereby blood flow to the ischemic tissue would be increased and tissue damage reduced and function improved. Therefore, according to the present invention adenosine kinase inhibitors may also be used to treat or prevent congestive heart failure.

In advanced coronary artery disease or persistent chest pain at rest, a number of clinical procedures are currently used to improve blood supply to the heart. These include percutaneous transluminal coronary angioplasty (PTCA), percutaneous transluminal directional coronary atherectomy, laser atherectomy, intravascular stents and coronary artery bypass graft surgery. The compounds of this invention will also be useful as adjunctive therapies to these techniques. Other clinical settings that involve ischemia would also be ameliorated by agents effecting regional blood flow including organ transplantation, skin flap grafting and other reconstructive surgery, peripheral vascular disease, endotoxemia, hemorrhagic shock, pulmonary emboli, pulmonary injury secondary to burns (thermal injury) or septicemia, pulmonary hypertension, microembolization, glomerulonephritis or progressive glomerulosclerosis, atherosclerosis, myocarditis, vasculitis, cardiomyopathies, intestinal ischemia, peripheral vascular disease, transient ischemic attacks, stroke and cardiopulmonary arrest. Adenosine kinase inhibitors will enhance protection afforded by preconditioning a tissue with a brief period of ischemia, before a more prolonged period of ischemia.

Thrombolytic therapy has been limited by a number of factors including the resistance of some thrombi to lysis, delays in reperfusion, and reocclusion following successful thrombolysis. These limitations are believed to be mediated, in part, by platelet aggregation (Born and Cross *J. Physiol.*, 1963, 166:29–30) and, since adenosine inhibits platelet aggregation in addition to its other effects on preventing ischemic injury, use of these adenosine kinase inhibitors may comprise a useful adjunctive therapy for thrombolytic therapy or for the treatment or prevention of thrombotic diseases such as myocardial infarction, stroke, angina, deep vein thrombosis, transient ischemic attacks, and pulmonary embolus.

Adenosine has been reported to be an endogenous modulator of inflammation by virtue of its effects on stimulated granulocyte function (Cronstein et al.,*J. Clin. Invest.*, 1986, 78:760–770) and on macrophage, lymphocyte and platelet function. The compounds of this invention may therefore be used in treating conditions in which inflammatory processes are prevalent such as arthritis, osteoarthritis, autoimmune disease, adult respiratory distress syndrome (ARDS), inflammatory bowel disease, necrotizing enterocolitis, chronic obstructive pulmonary disease (COPD), psoriasis, conjunctivitis, iridocyditis, myositis, cerebritis, meningitis, dermitis, renal inflammation, ischemia, reperfusion injury, peripheral vascular disease, atherosclerosis and other inflammatory disorders. Adenosine receptor agonists have been reported to be beneficial in an experimental model of inflammation. (Schrier, et al., *J. Immunol.*, 1990, 145:1874–1879).

Stroke and central nervous system ("CNS") trauma are conditions where tissue injury results from reduced blood supply to the CNS and are thus amenable to an intervention that provides increased levels of adenosine to the compromised tissue. It is reported that a significant component of the neurodegeneration resulting from stroke or CNS trauma or neurodegenerative diseases is caused by increased excitatory amino acid release and sensitivity, which results in neurons being stimulated-to death. In addition to its vasodilatory properties, adenosine has been reported to inhibit excitatory amino acid release (Burke and Nadler *J. Neurochem.*, 1988, 51:1541) and excitatory amino acid responsiveness. The compounds of this invention, which increase adenosine levels, may also be used in the treatment of conditions where release of or sensitivity to excitatory amino acids is implicated such as Parkinson's disease, Amyotrophic Lateral Sclerosis, Huntington's chorea or Alzheimer's disease (Maragos et al., *Trends Neurosci.*, 1987, 10:65 and Sonsella et al. *Science*, 1989, 243:398). These studies, together with results from experimental models of memory (Harris et al. *Brain Res.*, 1984, 323:132) suggest additional utilities of these compounds in the treatment of disorders related to the effects of the aging process on CNS function such as Alzheimer's disease. Other studies have also linked excitatory amino acids with the pathophysiology of schizophrenia. (Komhuber and Fischer, *Neurosci. Lett.*, 1982, 34:32; Kim et al. *Eur. Neurol.*, 1983, 22:367). This suggests that adenosine kinase inhibitors may be useful in treating schizophrenia.

These adenosine kinase inhibitors may also be useful in reducing anxiety, as skeletal muscle relaxants and in preventing skeletal muscle spasm.

Adenosine has been proposed to serve as a natural anticonvulsant (Lee et al., *Brain Res.*, 1984, 321:160–164; Dunwiddie, *Int. Rev. Neurobiol.*, 1985, 27:63–139). Agents that enhance adenosine levels may be used in the treatment of seizure disorders. Adenosine kinase inhibitors may be used in the treatment of patients with seizures or epilepsy or who might have chronic low or insufficient adenosine levels or might benefit from increased adenosine such as those suffering from autism, cerebral palsy, insomnia or other neuropsychiatric symptoms. Other excitatory neuromuscular tissues such as smooth muscle and cardiac muscle may be treated using these adenosine kinase inhibitors. In particular, these adenosine kinase inhibitors may be used to decrease contraction in smooth muscle such as in the gastrointestinal tract, or in vascular tissue such as an artery to prevent vasospasm which may limit blood supply to a tissue. Thus, these adenosine kinase inhibitors may be used to treat conditions such as Buerger's disease, Raynaud's disease, thromboangiitis obliterans, angina, unstable angina, silent ischemia, or transient ischemic attacks. Other conditions suitable for such therapy include cardiac arrhythmias (including supraventricular tachycardia), irritable bowel syndrome, and impotence.

To assist in understanding the present inventions and especially their properties and utilities, the results of a series of experiments are also included. These experiments demonstrated that a number of compounds of Formula I were potent inhibitors of a purified cardiac adenosine kinase with $IC_{50}$'s of less than 1 μM. Moreover, we have shown that these compounds are specific inhibitors of adenosine kinase with low affinity at the $A_1$ adenosine receptor and no significant adenosine deaminase (ADA) inhibition (Example A). We have demonstrated that a number of these compounds are also inhibitors of adenosine kinase in intact cells (Example B). These compounds include pyrrolo[2,3-d] pyrimidine nucleosides modified at the 5'-position or at other positions such that it is less likely to serve as a substrate for phosphorylation enzymes and that, in contrast to 5-iodotubercidin (GP-1-202), these compounds are unlikely to be phosphorylated at the 5'-position, incorporated into nucleotides or DNA, which may cause toxicity to cells or animals. We have demonstrated that inhibition of the cardiac adenosine kinase was achieved in vivo following systemic administration or, in some cases, oral administration of these compounds.

We have demonstrated the ability of these compounds to reduce damage resulting from ischemia and/or reperfusion in an experimental isolated heart model as shown in Example C. A more detailed study demonstrates that functional benefit may be achieved without vasodilatory effects on basal coronary flow which reflects increases in non-ischemic flow (indicative of the potential for coronary steal) or on heart rate. This result was unexpected given the previous descriptions by Newby et al (*Biochem. J.* 1983, 214:317–323) and Schrader (Regulatory Functions of Adenosine, Berne et al. eds., pp. 133–156 1983) of the increases in basal coronary flow caused by adenosine kinase inhibitors. Selected compounds, such as GP-1-238 (5'-amino-5'-deoxyadenosine), were also evaluated to determine the potential for toxic hemodynamic effects or hypothermia associated with administration of adenosine kinase inhibitors. No effects were observed in conscious animals on blood pressure, heart rate or temperature with doses of inhibitor greatly in excess of that required to inhibit the cardiac adenosine kinase (Example D).

Further experiments demonstrated that the adenosine kinase inhibitor GP-1-515 is beneficial in an experimental model of stable angina in dogs. In this study intravenous infusion of the compound attenuated the decline in function associated with repeated episodes of pacing-induced ischemia (Example E). The potential antithrombotic activity of adenosine kinase inhibitors is supported by the ability of GP-1-515 to abolish cyclic flow reductions (CFR's) in 3 out of 8 dogs examined in the Folts model of coronary artery thrombosis (Example F). These results support potential utility of these compounds in thrombotic diseases, such as angina and myocardial infarction.

In other experimental models, the ability of selected adenosine kinase inhibitors (GP-1-272 and GP-1-456) to inhibit neutrophil adherence to endothelial cells, an inflammatory response mediated at the cellular level was evaluated (Example G). Certain adenosine kinase inhibitors were found to exhibit anti-inflammatory activity in animal models of inflammation. The ability of adenosine kinase inhibitors (GP-1-515, GP-1-547) to attenuate contraction in the isolated ileum (Example H) supports the utility of these compounds in gastrointestinal disorders especially irritable bowel syndrome. In the central nervous system (CNS), the potent effects of selected adenosine kinase inhibitors (such as GP-1-456, GP-1-560) in attenuating chemical and electroshock induced seizures in experimental animal models demonstrates that these compounds will be useful as anticonvulsants in epilepsy (Example I), as well as in other CNS diseases treatable by local increases in adenosine levels. (GP-1-560 is 3-iodo-1-(5'-deoxy-B-D-ribofuranosyl) pyrazolo[3,4-d]pyrimidine.)

FORMULATIONS

Compounds of the invention are administered to the affected tissue at the rate of from 0.1 to 200 nmole/min/kg, preferably from 1 to 20 nmol/min/kg. Such rates are easily maintained when these compounds are intravenously administered as discussed below. When other methods are used (e.g., oral administration), use of time-release preparations to control the rate of release of the active ingredient may be preferred. These compounds are administered in a dose of about 0.01 mg/kg/day to about 100 mg/kg/day, preferably from about 0.1 mg/kg/day to about 10 mg/kg/day.

For the purposes of this invention, the compounds of the invention may be administered by a variety of means including orally, parenterally, by inhalation spray, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophylized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 200 $\mu$moles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 20 to about 50 moles of the active ingredient per milliliter of solution in order that infusion of a suitable volume at a rate of about 30 ml/hr can occur.

As noted above, formations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds of formula (I) as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the ddPN ingredient such carriers as are known in the art to be appropriate.

Formations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multidose sealed containers, for example, ampoules and vials, and may be sorted in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine kinase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used following thrombolysis for coronary occlusion. The compound would be given as a sterile injectable preparation with water or isotonic sodium chloride as the solvent. The solution can be administered intravenously or directly into the coronary artery at the time of left heart catheterization or into a carotid artery. The rate of administration could vary from 1 to 20 nmole/min/kg with, for example, an infusion volume of 30 ml/hr. Duration of therapy would typically be about 96 hours.

Angina and early myocardial infarcts can be treated by intravenous administration using a sterile injectable preparation using the rates discussed above.

Capsules comprising adenosine kinase inhibitors suitable for oral administration according to the methods of the present invention may be prepared as follows: (1) for a 10,000 capsule preparation: 1500 g of adenosine kinase inhibitor is blended with other ingredients (as described above) and filled into capsules which are suitable for administration depending on dose, from about 4 capsules per day (1 per 6 hours) to about 8 capsules per day (2 capsules per 6 hours), to an adult human.

The compounds of this invention and their preparation can be understood further by the examples which illustrate some of the processes by which these compounds are prepared. These examples should not however be construed as specifically limiting the invention and variations of the invention, now known or later developed, are considered to fall within the scope of the present invention as herein after claimed.

EXAMPLES

EXAMPLE 1

Preparation of 5'-Azido-5'-deoxy 2',3'-O-(1-methylethylidene) inosine

This material was prepared by tosylation of 2', 3'-(1-methylethylidene)inosine and subsequent reaction with sodium azide in DMSO as described by Hampton, A.; *J. Org. Chem.*, 1968, 11:1220.

EXAMPLE 2

Preparation of 9-[5-Azido-5-deoxy-2,3-O-(1-methylethylidene)-1-β-D-ribofuranosyl]-6-chloropurine A solution of the azide (Example 1) (12.01 g, 0.036 mole) in dry $CH_2Cl_2$ (500 ml) was added, during 1 hr, to a warm solution of $SOCl_2$ (8.1 ml, 0.11 moles) and DMF (4.05 ml, 0.05 moles) in $CH_2Cl_2$ (50 ml). The resulting solution was refluxed for 6 hrs while a continuous stream of a argon gas was bubbled through the reaction mixture to remove HCl. The reaction was cooled and added to a cold, rapidly stirred aqueous solution of $KHCO_3$. After stirring for 15 minutes the layers were separated and the organic layer was washed with cold aqueous $K_2CO_3$, $H_2O$(2x), dried ($Na_2SO_4$) and concentrated under vacuum. The residue was redissolved in $CH_2Cl_2$ and filtered through a plug of $SiO_2$ gel. Evaporation of the filtrate under vacuum gave 11.3 g (89% yield) of the title compound as a pale yellow oil.

EXAMPLE 3

General Procedure for the Preparation of $N^6$-Substituted-5'-azido-5'-deoxy-2',3'-O-(1-methylethylidene) adenosines To a solution of chloride (Example 2) (1 mmole/5 ml) in EtOH or n-BuOH was added amine (1.3.equivalents) and $Et_3N$ (1.8 equivalents). The solution was heated to reflux for 12–24 hours under Ar until judged complete by TLC. The reaction mixture was evaporated under vacuum, dissolved in $CH_2Cl_2$ and washed with aq. $K_2CO_3$ and $H_2O$. The $CH_2Cl_2$ solution was dried ($Na_2SO_4$) concentrated and used directly in the next step or chromatographed on $SiO_2$ gel using $CH_2Cl_2$-MEOH mixtures.

EXAMPLES 4 TO 14

General Procedure for the Preparation of $N^6$-Substituted-5'-azido-5'deoxyadenosines The $N^6$-substituted isopropylidene azide (Example 3) 10 g) was dissolved in $HCO_2H$ (10–20 ml) and diluted with an equal volume of $H_2O$. The reaction was followed by TLC. After disappearance of the starting material (12–48 hr), the reaction mixture was evaporated under vacuum, coevaporated with $H_2O$ (3x) then ETOH (2x). The residue was crystallized from $H_2O$, alcohol or mixtures.

The compounds in Table I (Examples 4–14) were prepared by this procedure:

TABLE I

| GPI-# | Example | F | MP (°C.) |
|---|---|---|---|
| 266 | 4 | ØNH | 121–126° |
| — | 5 | $CH_3NH$ | 180° (d) |
| 317 | 6 | 4-ClØNH | 209–210° |
| 299 | 7 | Ø$CH_2CH_2$NH | 144–146° |
| 337 | 8 | N-indolinyl | 157–159° |
| 346 | 9 | 4-(HOC$H_2CH_2$)ØNH | 147–151° |
| — | 10 | —NH$(CH_2)_{12}$NH— (dimer) | foam |
| 385 | 11 | N-indolyl[1] | 186–188° |
| 391 | 12 | N-(5-bromoindolinyl) | 194–196° |

TABLE I-continued

| GPl-# | Example | F | MP (°C.) |
|---|---|---|---|
| 421 | 13 | N-(5-methoxyindolinyl) | 184–185° |
| 557 | 14 | 1,4-piperazinyl | 198–204° |

[1] Prepared from indole and sodium hydride in DMF.

EXAMPLES 15–20

General Procedure for the Preparation of $N^6$-Substituted-5'-amino-5'-deoxyadenosines and Hydrochloride Salts A solution of the azide in EtOH or MeOH containing 10% Pd-C (25–50% weight of azide) was hydrogenated on a Parr shaker at 25 psi for 4–8 hours. The mixture was filtered, the catalyst rinsed well with solvent and the filtrate evaporated. The residue was recrystallized to give the free base or converted to the salt. The hydrochloride salt was prepared by slurrying or dissolving the free base in a small volume of EtOH, adding dry ethanolic HCl to a pH of 4–6, warming the mixture and then ling to crystalize out the salt (in some cases $Et_2O$ was added to precipitate the salt). The compounds in Table II (Examples 15–20) were prepared by this procedure:

TABLE II

| GPl-# | Example | F | M.P. °C. (salt) |
|---|---|---|---|
| 272 | 15 | $CH_3NH$ | 170–172° ($HCO_2H$) |
| 286 | 16 | ØNH | 169–173° (HCl) |
| 328 | 17 | $ØCH_2CH_2NH$ | 130° (d) (HCl) |
| 345 | 18 | N-indolinyl | 202–203° (HCl) |
| 373 | 19 | —HN(CH$_2$)$_{12}$NH— (dimer) | 151–153° (HCl) |
| 565 | 20 | 1,4-piperazinyl | 140–145° (HCl) |

EXAMPLE 21

Preparation of 5'-deoxy-2',3'-O-(1-methylethylidene) inosine

A solution of 5'-deoxy-5'-iodo-2',3'-O-(1-methylethylidene)inosine (5.45 g, 0.013 mol) in 80 ml of methanol containing triethylamine (2.0 g) and 10% palladium on charcoal (737 mg) was hydrogenated for 2 hr under 50 psi $H_2$. The reaction mixture was filtered and the filtrate concentrated and allowed to crystalize. The product was collected by filtration and dried under vacuum to give 2.45 g (82% yield) of the title compound.

EXAMPLE 22

Preparation of 6-Chloro-9-[5-deoxy-2,3-O-(1-methylethylidene)-1-β-D-ribofuranosyl]purine A solution of the blocked 5'-deoxyinosine (1.4 g, 4.8 mmol) tetraethylammonium chloride (1.9 g, 11.5 mmol), diethylaniline (1.2 ml, 7.2 mmol) and phosphorous oxychloride (3.35 ml, 36 mmole) in $CH_3CN$ (24 ml) was refluxed for 10 minutes then evaporated. The residue was dissolved in $CH_2Cl_2$, washed with water, aqueous $KHCO_3$ solution, water and dried ($Na_2SO_4$). The solution was concentrated and filtered through a plug of $SiO_2$ gel. The filtrate was evaporated to give 860 mg (65% yield) of title compound as a yellow oil.

EXAMPLE 23

General Procedure for Preparation of $N^6$-substituted 5'-deoxyadenosines

The above identified compounds were prepared using the procedures described in Example 3 and Examples 4–14.

The compounds listed in Table III were prepared by this procedure.

TABLE III

| GPl-# | EXAMPLE | F | M.P. (°C.) |
|---|---|---|---|
| 595 | 23 | 1,4-piperazinyl | 220–225° |

EXAMPLE 24

Preparation of 8-Bromo-2',3'-O-(1-methylidene)-5'-O-(4-methylbenzenesulfonyl)adenosine The above-identified compound may be prepared as described: Ikshara, M.; Kaneko, M.; Sagi, M.; *Tetrahedron*, 1970, 26:5757.

EXAMPLE 25

Preparation of $N^6$-Formyl-8-bromo-2',3'-O-(1-methylethylidene)-5'-O-(4-methylbenzenesulfonyl) adenosine To acetic-formic anhydride (prepared by stirring 25 ml of acetic anhydride and 12.5 ml of formic acid for 15 minutes at 45° C.) at 0° C., was added the tosylate (Example 24) (4.0 g, 7.30 mmol). The resulting solution was allowed to warm to 22° C. and stirred for 48 hours. The reaction mixture was evaporated, chased 2x with toluene and the residue dissolved in $CHCl_3$ and filtered through a plug of silica gel. Evaporation of the filtrate and crystallization of the residue from ethanol gave 4.0 g (96%) of the title compound.

EXAMPLE 26

Preparation of 5'-Deoxy-5',8-diazido-2',3'-O-(1-methylethylidene)adenosine

To a hot (75° C.), well stirred slurry of $NaN_3$ (2.23 g, 34.3 mmol) in dimethylsulfoxide (35 ml) was added the formyl tosylate (Example 25) (4.00 g, 6.9 mmoles). The reaction temperature was held at 75° C. for one hour then cooled to 25° C. The mixture was poured into stirring $H_2O$ (90 ml), slurried for ten minutes, the solid was collected by filtration, rinsed with $H_2O$ (3x), cold ethanol and dried. The crude product was dissolved in $CHCl_3$, filtered through silica gel and the filtrate evaporated to give the $N^6$-formyl derivative 1.20 g; m.p. 107°–110° C.

The $N^6$-formyl derivative was deformylated by slurrying in MeOH, adding saturated methanolic ammonia (80 ml) and warning until homogenous. After 15 minutes the solution was evaporated, the residue recrystallized from EtOH and dried to give the title compound; 0.900 g (60% yield); m.p. 166°–168° C.

EXAMPLE 27

Preparation of 5'-Deoxy-5'-8-diazidoadenosine

The isopropylidene diazide of Example 26 (1.00 g, 3.15 mmol) was deblocked as described under Example 4 and recrystallized from $H_2O$; 760 mg (85% yield); m.p. 128°–130°.

EXAMPLE 28

Preparation of 5'-Deoxy-5'-8-diaminoadenosine Formate

The diazide of Example 27 (0.660 g, 2.0 mmol) was hydrogenated as described under Example 15 and recrystal-

EXAMPLE 29

Preparation of 5'-Deoxy-5'-formylaminoadenosine

To cold (5° C.) acetic-formic anhydride (10 ml acetic anhydride and 5 ml formic acid) was added 5'-amino-5'-deoxy-2',3'-O-(1-methylethylidene)adenosine (670 mg, 2.0 mmol). The solution was stirred for 24 hours then evaporated, and coevaporated with toluene (2x) then EtOH. The residual foam was dissolved in methanolic ammonia containing $CH_2Cl_2$ and stirred overnight. TLC ($SiO_2$ gel, 9:1 $CHCl_3$-MeOH) indicated the initial product was converted to a more polar product. The solution was evaporated, the residue dissolved in $CHCl_3$ with 3% MeOH and filtered through a plug of $SiO_2$ gel. Evaporation of the filtrate gave 520 mg of a white foam. This material (500 mg) was deblocked with $HCO_2H$ as described for Example 4 and recrystallized from EtOH-$H_2O$ to give the title compound: yield 0.35 g (55%); m.p. 212°–213° C.

EXAMPLE 30

Preparation of 6-(N-Indolinyl)-9-[2,3-O-(1-methylethylidene)-1-β-D-ribofuranosyl]purine A mixture of the isopropylidene of 6-chloropurine riboside (11.5 g, 0.035 mol), indoline (5.13 ml, 0.046 mole) and triethylamine (8.82 ml, 0.063 mole) in n-butanol (60 ml) was stirred and heated to reflux for 24 hours. The reaction was cooled and the solid collected by filtration, rinsed with EtOH and dried to give the title compound: 10.70 g (75% yield); m.p. 119°–125° C.

EXAMPLE 31

Preparation of 6-(N-Indolinyl)-9-[2,3-O-(1-methylethylidene)-5-O-(4-methylbenzenesulfonyl)-1-β-D-ribofuranosyl)]purine To a cold (0° C.) solution of the alcohol (Example 30) (6.0 g, 0.015 mol) in dry pyridine (40 ml) was added with stirring, p-toluenesulfonyl chloride (6.96 g, 0.36 mol). The solution was sealed and stored at 0°–10° C. for 72 hours then poured with stirring into cold $H_2O$ (30 ml). The solid was collected by filtration and rinsed 3x with $H_2O$. After drying at 25° C. under vacuum, the title compound was obtained: 6.85 g (83% yield); m.p. 195° C. (d).

EXAMPLE 32

Preparation of 6-(N-Indolinyl)-9-[5-O-(4-methylbenzenesulfonyl)-1-β-D-ribofuranosyl)]purine A slurry of the protected tosylate (Example 31) (5.80 g, 10.0 mmole) in hydrochloric acid (23 ml) and EtOH (255 ml) was heated until homogenous then refluxed for 15 minutes. The solution was cooled in an ice bath and neutralized with $KHCO_3$. The solid was collected by filtration, washed with $H_2O$, EtOH then MeOH. After drying, 3.38 g (65% yield) of the title compound were obtained; m.p. 112° C.(d).

EXAMPLE 33

Preparation of 6-(N-Indolinyl)-9-(5-methylamino-5-deoxy-1-β-D-ribofuranosyl)purine Hydrochloride To 40% aqueous methylamine (40 ml) was added the tosylate (Example 32) (2.0 g, 3.8 mmol) and sufficient MeOH to give a clear solution. The solution was stirred for one week then concentrated under vacuum. The residue was coevaporated 3x with MeOH then recrystallized from MeOH to give the free base, 0.310 g (21% yield). A portion of this material was converted (ethanolic HCl) to the hydrochloride salt, m.p. 170°–172°.

EXAMPLE 34

Preparation of 4-Chloro-7H-pyrrolo[2,3-d]pyrimidine

The above-identified compound was prepared as described: Davoll, J.; *J. Chem. Soc.,* 1960, 131.

EXAMPLE 35

Preparation of 5-Bromo-4-chloro-7H-pyrrolo[2,3-d]pyrimidine

The above identified compound was prepared as described: Hinshaw, B.; Gerster, J.; Robins, R.; Townsend, L.; *J. Heterocyclic Chem.,* 1969, 215.

EXAMPLE 36

Preparation of 4-Chloro-5-iodo-7H-pyrrolo[2,3-d]pyrimidine

The above-identified compound was prepared as described: Pudlo, J.; Nassiri, M.; Kern, E.; Wartiny, L.; Drach, J.; Townsend, L.; *J. Med. Chem.,* 1990, 33, 1984.

EXAMPLE 37

Preparation of 4-Chloro-5-methyl-7H-pyrrolo[2,3-d]pyrimidine

The above-identified compounds was prepared as described: Pudlo, J.; Nassir, M.; Kern, E.; Wotring, L.; Drach, J.; Townsend, L.; *J. Med. Chem.,* 1990, 33, 1984.

EXAMPLE 38

Preparation of 4-Chloro-2-methylthio-7H-pyrrolo[2,3-d]pyrimidine

The above-identified compound was prepared as described: Noel, C., Robins, R.; *J. Heterocyclic Chem.,* 1964, 1, 34.

EXAMPLE 39

Preparation of 2-Amino-4-chloro-7H-pyrrolo[2,3-d]pyrimidine

The above-identified compound was prepared as described: Pudlo, J.; Nassiri, M.; Kern, E.; Wotrlng, L.; Drach, J.; Townsend, L.; *J. Med. Chem.,* 1990, 33, 1984.

EXAMPLE 40

Preparation of 2-Amino-4-chloro-7H-pyrrolo[2,3-d]pyrimidine

The above-identified compound was prepared as described. Seela, F.; Stiker, H.; Driller, H.; Binding, N.; *Liebigs Ann. Chem.,* 1987, 15.

EXAMPLE 41

Preparation of 4-Chloro-5-methylthio-7H-pyrrolo[2,3-d]pyrimidine

A solution of 5-bromo-4-chloro-7H-pyrrolo[2,3-d]pyrimidine (Example 35) (2.53 g, 10 mmol) in anhydrous THF (30 mL) was cooled to −78° C. under argon and a solution of n-butyl lithium (12 mL of 2.3M solution, 25 mmol) was added at such a rate that the reaction temperature remained below −72° C. After the addition, the reaction mixture was stirred at −78° C. for 45 min, a solution of methyl disulfide (0.95 ml, 10 mmol) in tetrahydrofuran (10 mL) was added over a period of 30 minutes maintaining the temperature below −72° C. The reaction mixture was stirred at −78° C. for 2.5 hours then allowed to warm to room temperature. A saturated solution of ammonium chloride (40 mL) was added to the reaction with stirring. The organic layer was separated, the aqueous layer extracted with ethyl acetate (2×40 mL) and the combined organic extracts were dried ($MgSO_4$), filtered and evaporated to obtain a pale yellow solid which was crystallized from EtOH: yield 1.65 g; (70%) m.p. 166°–167° C.

EXAMPLE 42

Preparation of 4-Chloro-5-cyano-7H-pyrrolo[2,3-d]pyrimidine

A 2.31M solution of n-butyllithium in hexane (6.1 mL, 14.0 mmol) was added dropwise to a solution of 4-chloro-5-bromopyrrolopyrimidine (Example 35) (1.481 g, 6.37 mmol) in 65 mL THF at −78° C. and the resulting light yellow suspension stirred at this temperature for 1 hour. A cold (−78° C.) solution of p-tolylsulfonylcyanide (2.08 g, 11.5 mmol) in 35 mL THF was added dropwise via cannula and the resulting mixture stirred at this temperature for 1 hour. Aqueous $NH_4Cl$ was added and the resulting solution was diluted with 100 mL $CH_2Cl_2$. The organic layer was separated, washed with water, brine, dried ($MgSO_4$) and evaporated to provide a tan solid (1.3 g) which appeared to be a 1:1 mixture of the title nitrile and 4-chloropyrrolopyrimidine by $^1$NMR. This material was recrystallized from 25 mL ethanol to provide 435 mg (38%) of the title nitrile as a tan solid: m.p. 300° C.

This compound may also be prepared as described: Tollman et al., *J. Amer. Chem. Soc.*, 1969, 91:2102.

EXAMPLE 43

Preparation of 4-Chloro-5-ethoxycarbonyl-7H-pyrrolo[2,3-d]pyrimidine

A solution of 5-bromo-4-chloropyrrolo[2,3-d]pyrimidine (Example 35) (232 mg; 1 mmol) in anhydrous THF (5 mL) was cooled to −78° C. under argon and a solution of n-butyl lithium (1.3 mL of 2.31M) was added at such a rate that the temperature of the reaction mixture remained below −72° C. After stirring the reaction mixture at −78° C. for 45 minutes, a solution of ethyl chloroformate (0.15 mL) in THF (2 ml) was added slowly, maintaining the reaction temperature below −72° C. The reaction mixture was stirred at −78° C. for 2 hours then allowed to warn to room temperature. A saturated solution of $NH_4Cl$ (20 mL) was added to the reaction mixture. The organic layer was separated and the aqueous layer was extracted with ethyl acetate (2×25 mL). The combined organic extracts were dried and evaporated to a white solid, yield 210 mg (92%): m.p. 140°–141° C.

EXAMPLE 44

Preparation of 5-O-[(1,1-Dimethylethyl)dimethylsilyl]-2,3-O-(1-methylethylidene)-D-ribofuranose The above-identified compound was prepared as described: H. Rosemeyer, H.; Seela, *Helv. Chim. Acta.*, 1988, 71, 1573.

EXAMPLE 45

Preparation of 5-Deoxy-D-ribofuranose

The above-identified compound was prepared as described; Snyder J.; Serianni, A.; *Carbohydrate Research*, 1987, 163, 169.

EXAMPLE 46

Preparation of 5-O-Methyl-D-ribofuranose

The above-identified compound was prepared as described: Snyder, J.; Serianni, A.; *Carbohydrate Research*, 1987, 163, 169.

EXAMPLE 47

Preparation of 1-O-Methyl-2,3-O-(1-methylethylidene)-5-O-(4-methylbenzenesulfonyl)-D-ribofuranoside The above-identified compound was prepared as described: Snyder, J.; Serianni, A.; *Carbohydrate Research*, 1987, 163, 169.

EXAMPLE 48

Preparation of 5-Deoxy-2,3-(1-methylethylidene)-D-ribofuranose

5-Deoxy-D-ribofuranose (8.g, 60 mmole) was dissolved in DMF (25 ml) and to the solution was added dimethoxypropane (10 ml) and p-toluenesulfonic acid (150 mg). The reaction was stirred overnight then neutralized with Amberlite 400 (OH resin. The mixture was filtered, concentrated and the residue chromatographed on $SiO_2$ gel using 15:1 $CH_2Cl_2$-MeOH. The appropriate fractions were collected and evaporated to yield 4.1 g (39% yield) of viscous liquid.

EXAMPLE 49

Preparation of 5-O-Methyl-2,3-O-(1-methylethylidene)-D-ribofuranose

To a solution of 5-O-methyl-D-ribofuranose (6.0 g, 36 mmole) in dry DMF (25 mL), 2,2-dimethoxypropane (25 mL) and p-toluenesulfonic acid (250 mg) were added and the solution was stirred at room temperature for 20 hours. Volatile materials were evaporated under reduced pressure and the residue was chromatographed over $SiO_2$ gel using 3:1 hexane:ethyl acetate. Appropriate fractions were pooled and evaporated to give the title compound as an oily product, yield: 5.0 g (68%).

EXAMPLE 50

5-Azido-5-deoxy-1-O-methyl-2,3-O-(1-methylethylidene)-D-ribofuranoside

A mixture of 1-O-methyl-2,3-O-(1-methylethylidene)-5-O-(4-methylbenzenesulfonyl)-D-ribofuranoside (8.0 g, 22 mmol), dry DMF (40 mL) and $NaN_3$ (4.0 g, 62 mmol) was heated at 80° C. under anhydrous conditions for 12 hours. The solvent was evaporated under high vacuum and the residue was chromatographed over silica gel using $CH_2Cl_2$. The fractions containing the faster moving product were pooled and evaporated to obtain 4.8 g (94% yield) of a syrupy product.

EXAMPLE 51

Preparation of 5-Azido-5-deoxy-D-ribofuranose

A solution of 5-azido-5-deoxy-1-O-methyl-2,3-O-(1-methylethylidene)-D-ribofuranoside (4.6 g, 20 mmol) in 0.1% $H_2SO_4$ (300 mL) was gently refluxed for 3 hours. The acid was neutralized (pH ~5) with Amberlite 400 ($OH^-$ form) and the resin filtered and washed with ethanol (2×20 mL). The filtrate was evaporated to dryness under high vacuum to give the title compound as a syrupy residue; $^1H$ and $^{13}C$ NMR confirmed the identity of the product as a mixture of α and β anomers.

EXAMPLE 52

Preparation of 5-Azido-5-deoxy-2,3-O-(1-methylethylidene)-β-D-ribofuranose

The crude 5-azido-5-deoxyribose (Example 51) was dissolved in dry DMF (10 mL) and treated with 2,2- dimethoxypropane (10 mL) and p-toluenesulfonic acid (100 mg). The solution was stirred at room temperature for 20 hours then evaporated under high vacuum. The residue was chromatographed over $SiO_2$ gel using 3:1 hexane:ethyl acetate. The appropriate fractions were pooled and evaporated to obtain the title compound, yield 2.4 g (56% yield).

EXAMPLE 53

Preparation of 1-O-Methyl-2,3-O-(1-methylethylidene) D-pentodialdo-1,4-furanoside The above-identified compound was prepared as described: Moorman, A.,; Borchardt, R.; *Nucleic Acid Chemistry-Part III*, Ed. Towsend, L., Tipson, R.; John Wiley and Sons, N.Y.; 1986, pages 38–41.

EXAMPLE 54

Preparation of 5-Benzoyl-D-allofuranose

The sugar aldehyde from Example 53 (100 mmole) was dissolved in anhydrous THF and treated with a commercially available solution of methyl magnesium bromide (100 mmol) under anhydrous conditions. After 2 hours of stirring at room temperature, a saturated solution of ammonium chloride in water (180 mL) was added. The organic layer was separated and the aqueous layer was extracted with ether (2×100 mL). The combined organic layers were dried and evaporated to obtain an oily product whose NMR was consistent with methyl-6-deoxy-2,3-isopropylidene-D-allofuranoside. The crude product was dissolved in pyridine (50 ml) and treated with benzoic anhydride (120 mmole). After stirring for 18 hours, methanol (2 ml) was added and the reaction mixture was evaporated under high vacuum. The residue was dissolved in ethyl acetate (300 ml) and washed successively with water, saturated bicarbonate solution, and brine. The organic layer was dried and evaporated to obtain a glassy product which was purified by column chromatography. Identity of the product was confirmed by IR and NMR spectroscopy. The intermediate protected sugar was then heated with aqueous sulfuric acid solution (0.01N in water, 300 ml) to @ 80° C. for 2 hours and neutralized with strongly basic ion exchange resin. The aqueous layer was separated and evaporated under high vacuum to obtain the title compound as a sticky mass. The product was confirmed by NMR and used in the next step without further purification.

EXAMPLE 55

Preparation of 5-Benzoyl-6-deoxy-2,3-O-(1-methylethylidene)-D-allofuranose

The benzoylated sugar (Example 54) was dissolved in a mixture of dry DMF (20 ml), 2,2-dimethoxypropane (20 ml) and p-toluenesulfonic acid (200 mg) and stirred at room temperature with the exclusion of moisture. The reaction was complete within two hours as evidenced by the absence of the starting material (TLC). The acid was neutralized by strongly basic ion exchange resin and the resin removed by filtration and washed. The combined washings and filtrate were evaporated under high vacuum and the residue was purified by chromatography. The pure product obtained was a glassy solid. IR and NMR were consistent with the title compound.

EXAMPLE 56

Preparation of 5,6-Dideoxy-5,6-didehydro-1-O-methyl-2,3-O-(1-methylethyldene)-D-allofuranoside To a suspension of potassium-tert-butoxide (9.36 g) in anhydrous ether (300 ml), methyltriphenylphosphonium bromide (29.6 g) was added in small portions over 5 minute period with stirring under anhydrous conditions. The bright yellow colored solution (with some solid separated). was stirred for 1½ hours then a solution of methyl-2,3-isopropylidene-D-pentodialdo-1,4-furanoside (8.0 g), Example 53, in anhydrous ether (75 ml) was added over 5 minute period. The reaction mixture was stirred overnight at room temperature. The solid material that formed in the reaction mixture was removed by filtration and washed repeatedly with ether. The combined washings and filtrate were evaporated and the residue purified by chromatography to obtain 6.5 g of product as an oil; TLC $R_f$+0.5 (Silica gel, 97:3 hexane: EtoAc).

EXAMPLE 57

Preparation of 5,6-Dideoxy-5,6-didehydro-2,3-O-(1-methylethylidene)-D-allofuranose A mixture of 5,6-dideoxy-5,6 didehydro-1-O-methyl-2,3-O-(1-methylethylidene)-D-allofuranose (Example 56) (2.0 g), and aqueous $H_2SO_4$ (0.1%, 50 ml) was heated to 90° for 3 hours at which time the indicated the starting material was consumed. The pH of the solution was adjusted to 7.5 with 1N NaOH solution, and evaporated to dryness. The residue was evaporated with DMF (2×20 ml) and the resulting semi solid product was slurried in methanol (25 ml). The undissolved solid was removed by filtration and washed with methanol (2×20 ml). The combined washings and the filtrate were evaporated to dryness and the resulting residue was dissolved in a mixture of dry DMF (10 ml), 2,2-dimethoxypropane (6 ml) and p-toluenesulfonic acid (50 mg). After stirring for 2 hours at room temperature the acid was neutralized with ion exchange resin (strongly basic type) and the resin was removed by filtration. Evaporation of the filtrate gave a product which was purified by chromatography over silica gel using 97:3 hexane:EtOAc as the a mobile phase; $R_f$ of the product 0.8 (silica gel, 9:1 hexane;EtOAc).

EXAMPLE 58

Preparation of 5,6-Dideoxy-1-O-methyl-2,3-(1-methylethylidene)-D-allofuranoside

A solution of the vinylic sugar (6.2 g), Example 56, in methanol (55 ml) was purged with argon and hydrogenated using 10% platinum on carbon as catalyst at 80 psi for 100 hours. The catalyst was removed by filtration and washed with methanol. The combined washings and filtrate were evaporated to obtain a colorless oil used directly for the next step. Yield: quantitative. TLC $R_f$=0.48 (Silica gel, 97:3 Hexane:EtOAc)

EXAMPLE 59

Preparation of 5.6-Dideoxy-2,3-O-(1-methylethylidene)-D-allofuranose

A mixture of 5,6-dideoxy-1-methyl-2,3-O-(1-methylethylidene)-D-allofuranoside (5.8 g), (Example 58), and water (160 ml) containing 0.16 ml of conc $H_2SO_4$ was heated to 90° C. for 3 hours. The pH of the reaction mixture was adjusted to 7.5 with 1N NaOH solution and evaporated to dryness under high vacuum. The residue was coevaporated with DMF (2×50 ml) then dissolved in methanol (25 ml) and filtered. The filtrate was evaporated, dissolved in a mixture of dry DMF (10 ml), 2,2-dimethoxypropane (10 ml) and p-toluenesulfonic acid (200 mg) and stirred for 2 hours. The acid was neutralized with strongly basic ion exchange resin and the resin removed by filtration. The filtrate was evaporated and the residue chromatographed to obtain the title product; yield: 4.3 g.; TLC, $R_f$=0.6 (Silica gel, 2:1 hexane: EtOAc).

EXAMPLE 60

Preparation of 5-deoxy-1-O-methyl-2,3-O-(1-methylethylidene)-D-allofuranoside

To a solution of the vinylic sugar Example 56 (4.1 g) in THF (20 ml), borane:THF solution (10.65 ml of 1M solution in THF) was added over 10 minutes. After stirring 2 hours at room temperature the reaction vessel was immersed in a cooling bath (ice-water) and an aqueous solution of NaOH (8 ml of 3M solution) was added with stirring. After 15 minutes a solution of $H_2O_2$ (30% aq. 4 ml) was added dropwise, and stirring was continued for an additional 15 minutes. Then the flask was immersed for 30 minutes in a water bath maintained at 55° C. and cooled. The contents were extracted with methylene chloride (3×150 ml) and the organic layer was dried over anhydrous $MgSO_4$. The solvent was evaporated and the residue was chromatographed over silica gel using a hexane:ethyl acetate gradient as solvent. The fast moving minor product, $R_f$=0.7, (10%) was identified as 6-deoxy-1-methyl-2,3-O-(1-methylethylidene)-D-allofuranoside. The slower moving major product (90%), $R_f$=0.3 was identified by proton NMR to be the title compound; yield 3.7 g; $R_f$=0.3 (silica gel, 2:1 hexane:EtOAc).

EXAMPLE 61

Preparation of 6-O-(t-Butyldimethylsilyl)-2,3-O-(1-methylethylidene)-D-allofuranose This compound may be prepared by t-butyldimethylsilylation of the corresponding 6-hydroxy sugar, using t-butyldimethylsilyl. chloride and imidazole in DMF.

EXAMPLE 62

Preparation of 5-deoxy-1-methyl-2 3-O-(1-methylethylidene)-6-p-toluenesulfonyl-D-allofuranoside To an ice-cold solution of the hydroxy sugar Example 60, (3.69 g) in anhydrous pyridine (25 ml), p-toluenesulfonyl chloride (3.7 g) was added in small portions. The reaction mixture was stirred and allowed to warm to room temperature over 2 hours, at which time the reaction was complete (TLC). Unreacted p-toluenesulfonyl-chloride was quenched by adding 1 ml of methanol and the volatile components were evaporated under high vacuum. The residue was evaporated with DMF (2×20 ml), then dissolved in ethyl acetate (350 ml). The solution was washed successively with water and bicarbonate solution and the organic layer was dried over anhydrous $MgSO_4$. Evaporation of the solvent gave a residue which was purified by silica gel column chromatography; yield 4.1 g; $R_f$=0.8 (silica gel 2:1 hexane:EtOAc). Proton NMR indicated the product to be a mixture of α and β anomers.

EXAMPLE 63

Preparation of 6-azido-5,6-dideoxy-1-O-methyl-2,3-O-(1-methylethylidene)-D-allofuranoside A mixture of the tosyl sugar, Example 62, (4.0 g), dry DMF (20 ml) and sodium azide (1.5 g) was heated to 100° C. in an oil bath under anhydrous conditions for 24 hours. The solvents were evaporated under high vacuum and the residue was dissolved in ethyl acetate (200 ml) and washed with water. The organic layer was dried ($MgSO_4$) and evaporated to obtain a colorless oil which was sufficiently pure by TLC and NMR for use in the next reaction; yield 2.09 g; $R_f$=0.35 (silica gel, 93:7 hexane:EtOAc).

EXAMPLE 64

Preparation of 6-azido-5,6-dideoxy-2,3-O-(1-methylethylidene)-D-allofuranose

A mixture of the azido sugar Example 63 (2.8 g), and aqueous sulfuric acid solution (100 ml of 0.1% by volume) was heated to 90° C. for 3½ hours at which time the starting material was found (TLC) to be consumed. The pH of the reaction mixture was adjusted to at 7.5 with 1N NaOH and evaporated to dryness under high vacuum. The residue was coevaporated with DMF (2×20 ml) and treated with methanol (25 ml). The insoluble solids were removed by filtration and washed with methanol (2×20 ml). The combined filtrates were evaporated to dryness. The oily product thus obtained was dissolved in a mixture of dry DMF (10 ml), 2,2-dimethoxy propane (6 ml) and p-toluene sulfonic acid (50 mg) and stirred for 2 hours at room temperature. The solvents were evaporated under high vacuum and the residue was chromatographed over a silica gel column using a 4:1 hexane:EtOAc mixture as the mobile phase. After a fast moving spot, fractions containing the main product were combined and evaporated to obtain the title compound as a colorless oil; Yield 1.89 g; $R_f$=0.5 (silica gel, 2:1 hexane:EtOAc).

EXAMPLES 65–81

General Procedure for the preparation of 5'-substituted-4-chloropyrrolo[2,3-d]pyrimidine-7-(1-β-D-ribosides)

A solution of the 5-substituted (H, $OCH_3$, $N_3$ or TBDMS-O-) 5-deoxy-isopropylideneribose (1 eq) in $CCl_4$ (1.4 eq) and THF was cooled to −78° C. Hexamethylphosphorous triamide (1.2 eq) was added dropwise and the reaction mixture stirred for 2 hours at −78° C. This solution of 1-α-chloro sugar was used directly in the next step.

To a slurry or solution of the substituted 4-chloropyrrolo[2,3-d]pyrimidine (1.4 eq corresponding to the sugar) in DMF, was added in four portions, NaH (1.4 eq) over 10 minutes. The solution was stirred 30 minutes then the above solution of chloro sugar (−25° C.) was added and the reaction was stirred for 24 hours. The mixture was concentrated, diluted with EtOAc, filtered and the filtrate concentrated under vacuum. The residue was chromatographed on SiO$_2$ gel using 2:1 hexane-EtOAc. The appropriate fractions were collected and evaporated to yield the protected nucleoside.

The protected nucleoside was deblocked by dissolving in 90% trifluoroacetic acid and stirring for 2 hours. The solvent was evaporated and chased with methanol (3x). The product was crystrallized from EtOH or EtOAc.

The compounds in Table IV (Examples 65–81) were prepared by this procedure:

TABLE IV

| GPl-# | EXAMPLE | B' | D | G | m.p (°C.) |
|---|---|---|---|---|---|
| 475 | 65 | CH$_2$OH | I | H | 183–181° |
|  | 66 | CH$_2$N$_3$ | I | NH$_2$ | 203–205° |
| 406 | 67 | CH$_2$OH | Br | H | >230° |
| 448 | 68 | CH$_3$ | I | H | 180–181° |
| 449 | 69 | CH$_3$ | CH$_3$ | H | 155–157° |
| 462 | 70 | CH$_2$OCH$_3$ | CH$_3$ | H | 142–144° |
| 460 | 71 | CH$_2$OCH$_3$ | I | H | 179–180° |
| 464 | 72 | CH$_2$OCH$_3$ | H | H | 122–124° |
| 692 | 73 | —CH$_2$CH$_3$ | Br | H | 163–165° |
| 690 | 74 | —CH$_2$CH$_3$ | I | H | 181–183° |
| 529 | 75 | CH$_2$N$_3$ | I | H | 203–205° |
| 554 | 76 | CH$_3$ | Br | H | 174–175° |
| 555 | 77 | CH$_3$ | H | CH$_3$S | 140–142° |
| 569 | 78 | CH$_3$ | SCH$_3$ | H | 147–148° |
| 605 | 79 | CH$_2$N$_3$ | Br | H | 156–158° |
| — | 80 | CH$_2$CH$_2$N$_3$ | I | H | foam |
| 713 | 81 | CH=CH$_2$ | I | H | 183–185° |

EXAMPLES 82–83

Preparation of 4-Amino-7-(5-amino-5-deoxy-1-β-D-ribofuranosy)-5-halopyrrolo[2,3-d]pyrimidines A mixture of 4-chloro-5-iodo-7-[5-azido-5-deoxy-1-β-D-ribofuranosyl]pyrrolo[2,3-d]pyrimidine (Example 75 or 79) (500 mg), triphenylphosphine (550 mg) and pyridine (6 ml) was stirred under an argon atmosphere at room temperature for 24 hours. Pyridine was evaporated under high vacuum and the residue was triturated with ether. The residual semi-solid was treated with ammonium hydroxide (5 ml). A small amount of ethanol was added to cause complete dissolution of the compound. After stirring for 5 hours at room temperature the mixture was evaporated under vacuum and the residue was triturated with water (10 ml). The insoluble material was removed by filtration and the pH of the filtrate was adjusted to 5.5 with dilute HCl. The solution was refiltered and lyophilized to obtain a hygroscopic solid, whose NMR was compatible with the structure.

The above hygroscopic solid was dissolved in methanol, saturated with dry ammonia at at −15° C., then heated in a steel bomb at 80° C. for 24 hours. The bomb was cooled and opened. Ammonia and methanol were evaporated and the residue was dissolved in water, charcoaled and filtered. The filtrate was lyophilized to obtain the title compound as a hygroscopic solids. The compounds listed in Table V were obtained by this procedure.

TABLE V

| GP 1-# | EXAMPLE | D | F | m.p (°C.) |
|---|---|---|---|---|
| 550 | 82 | I | H | 166–206° |
| 649 | 83 | Br | H | 217–219° |

EXAMPLE 84

Preparation of 4-Amino-5-iodo-7-(5-acetylamino-5-deoxy-1-β-D-ribofuranosyl)pyrrolo[2,3-d] pyrimidine To an ice cold solution of the 5'-amino compound from Example 54 (50 mg), in dry pyridine (5 ml), acetic anhydride (0.5 ml) was added with stirring. The reaction mixture was allowed to warm to room temperature over a period of 1 hour at which time the reaction was complete. The flask was reimmersed into the cooling bath and 15 ml of methanol was added to the reaction mixture to neutralize unreacted acetic anhydride. The solvent was evaporated under reduced pressure and the residue was purified by a short column chromatography to give the above-identified product, m.p. 160°–163° C.

EXAMPLES 85 TO 113B

General Procedure for the Preparation of N$^4$-Substituted-4-aminopyrrolo[2,3-d]pyrimidine Nucleosides A suspension of the substituted 4-Cl-pyrrolo[2,3-d] pyrimidine nucleoside (1 eq) in EtOH containing the amine (3 eq) and triethylamine (5 eq) was added to a small stainless steel bomb (in the case of diamines a 25% excess of chloride was used). The bomb was heated overnight (bath temperature 70°–120° C.), cooled, opened and the reaction mixture evaporated.

The product was crystallized from ethanol or ethyl acetate compounds in Table VI (Examples 85 to 113B) were prepared by procedure:

TABLE VI

| GPl-# | Example | B' | D | F | G | m.p. (°C.) |
|---|---|---|---|---|---|---|
| 334 | 85 | CH$_2$OH | H | NH$_2$ | H | 249–250° |
| 394 | 86 | CH$_2$OH | H | N-indolinyl | H | Foam |
| 393 | 87 | CH$_2$OH | H | N-prolinyl | H | Foam |
| 296 | 88 | CH$_2$OH | H | cyclopentyl-NH | H | Foam |
| 376 | 89 | CH$_2$OH | Br | NH$_2$ | H | Foam |
| 321 | 90 | CH$_2$OH | H | NHØ | H | Foam |
| 476 | 91 | CH$_2$OH | I | N-Indolinyl | H | 185–188° |
| 456 | 92 | CH$_3$ | I | NH$_2$ | H | 245–246° |
| 470 | 93 | CH$_3$ | I | N-indolinyl | H | 188–190° |
| 457 | 94 | CH$_3$ | I | CH$_3$NH | H | 226–228° |
| 485 | 95 | CH$_3$ | I | N$_3$ | H | 213–214° |
| 498 | 96 | CH$_3$ | CH$_3$ | NH$_2$ | H | 212–214° |
| 461 | 97 | CH$_3$ | CH$_3$ | N-indolinyl | H | 171–173° |

TABLE VI-continued

| GPl-# | Example | B' | D | F | G | m.p. (°C.) |
|---|---|---|---|---|---|---|
| 463 | 98 | $CH_2OCH_3$ | I | $NH_2$ | H | 216–218° |
| 465 | 99 | $CH_2OCH_3$ | I | $CH_3NH$ | H | 188–189° |
| 474 | 100 | $CH_2OCH_3$ | H | N-indolinyl | H | 205–208° |
| 480 | 101 | $CH_2OCH_3$ | H | $CH_3NH$ | H | 163–164° |
| 513 | 102 | $CH_3$ | H | N-piperazinyl | H | 216–219° |
| 499 | 103 | $CH_3$ | I | N,N'-piperazinyl[1] | H | 220–223° |
| 500 | 104 | $CH_3$ | I | $-NH(CH_2)_6NH-$[1] | H | 227–229° |
| 512 | 105 | $CH_3$ | I | $-NH(CH_2)_2NH-$[1] | H | >230° |
| 559 | 106 | $CH_3$ | I | $NH_2$ | $CH_3S$ | 200–202° |
| 561 | 107 | $CH_3$ | H | 1,4-piperazinyl[2] | H | foam |
| 606 | 108 | $CH_2N_3$ | Br | $NH_2$ | H | 182–184° |
| 639 | 109 | $CH_3$ | I | NHØ | H | >230° |
| 581 | 110 | $CH_3$ | $CO_2C_2H_5$ | $NH_2$ | H | 162–168° |
| 681 | 111 | $CH_2OH$ | I | NHØ | H | 224–225° |
| 680 | 112 | $CH_2OH$ | I | NH(4-ClØ) | H | 234–235° |
| 689 | 113 | $CH_2OH$ | I | NH(4-$CH_3$O-Ø) | H | 212–214° |
| 711 | 113A | $CH_2CH_2N_3$ | I | $NH_2$ | H | 151–153° |
| 714 | 113B | $CH=CH_2$ | I | $NH_2$ | H | 224–226° |

[1]Dimers having two pyrrolo[2,3-d]pyrimidine riboside moieties linked by the listed diamine.
[2]Dimer with purine riboside.

EXAMPLE 114

Preparation of 5-Iodo-7-(5-deoxy-1-β-D-ribofuranosyl)pyrrolo[2,3-d]pyrimidin-4(3H)-thione A solution of 4-chloro-5-iodo-7-[5-deoxy-1-β-D-ribofuranosyl]pyrrolo[2,3-d]pyrimidine (Example 68) (250 mg, 0.60 mmol) and thiourea (250 mg) in absolute EtOH was refluxed gently under an argon atmosphere for 16 hours. The solvent was evaporated under reduced pressure and the residue was triturated with water (10 ml). The solid was collected by filtration, washed with water and dried in air: Yield 200 mg (81%); m.p. 161°–163° C.

EXAMPLES 115 TO 120

General Procedure for S-Alkylation of 5-Iodo-7-(5-deoxy-1-β-D-ribofuranosyl)pyrrolo[2,3-d]pyrimidin-4(3H)-thione To a solution of 5-iodo-7-(5-deoxy-1-β-D-ribofuranosyl)pyrrolo[2,3-d]pyrimidine-4-thione (Example 114) (50 mg) in concentrated $NH_4OH$ (10 ml), the appropriate alkylating agent (e.g. methyl iodide, alkyl or substituted benzyl bromide) was added and the mixture stirred at room temperature for 20 hours. Volatile material was evaporated under reduced pressure and the residue triturated with ether. To the residue, water (5 ml) was added and the solid was collected by filtration and washed with water.

The products obtained by this procedure (Examples 115 to 120) are listed in Table VII:

TABLE VII

| GPl-# | Example | B' | D | F | m.p. |
|---|---|---|---|---|---|
| 482 | 115 | $CH_3$ | I | $SCH_3$ | 212–233° |
| 493 | 116 | $CH_3$ | I | $SCH_2CH=CH2$ | 192–193° |
| 494 | 117 | $CH_3$ | I | $SCH_2ØNO_2(4)$ | 224–226° |
| 502 | 118 | $CH_3$ | I | $SC_4H_9$ | 186–187° |
| 503 | 119 | $CH_3$ | I | $SCH_2Ø$ | 212–213° |
| 511 | 120 | $CH_2OH$ | I | $SCH_3$ | 214–150° |

EXAMPLE 121

Preparation of 4-Phenyl-7-(1-β-D-ribofuranosyl)pyrrolo[2,3-d]pyrimidine

To a solution of 4-chloro-7-[2,3-O-(1-methylethylidene)-1-β-D-ribofuranosyl]pyrrolo[2,3-d]pyrimidine (200 mg) and phenylboronic acid (250 mg) in dry diglyme (10 ml) was added palladium-tetrakis-triphenylphosphine (30 mg), followed by aqueous $Na_2CO_3$ solution (0.2 ml of 2M solution). The reaction mixture was heated to 90° C. under anhydrous conditions for 6 hours. The solvent was evaporated under high vacuum and the residue was purified by HPLC on a reverse phase C-18 column. The purified intermediate was treated with 2 ml of trifluoracetic acid (80%) and stirred for 15 minutes then evaporated under high vacuum and the residue crystallized from ethanol; yield 20 mg, m.p. 163°–164° C.

EXAMPLES 122 TO 124

General Procedure for the Preparation of 4-Amino- and 4-Arylamino-5-aryl-7-(1-β-D-ribofuranosyl)pyrrolo-[2,3-d]pyrimidines To stirred mixture of the 4-amino- or 4-arylamino-5-iodopyrrolo[2,3-d]pyrimidine riboside (or corresponding hydroxyl protected compound) (0.1 m mole), $Pd(PPh_3)_4$ (10 mg, 0.01 mole) in diglyme was added a solution of the arylboronic acid (0.4 mmol) in EtOH and 0.4 ml of aqueous 2M $Na_2CO_3$. The mixture was heated to 100° C. and the reaction monitored by TLC. After the reaction was complete, the cooled mixture was filtered and concentrated under vacuum. The residue was chromatographed over $SiO_2$, eluting with $CH_2Cl_2$-MeOH mixtures or by HPLC on a Bondapak C-18 column with a MeOH-$H_2O$ gradient.

The compounds in Table VIII may be prepared by this procedure:

TABLE VIII

| GPl # | Example | D | F | M.P. (°C.) |
|---|---|---|---|---|
| — | 122 | Ø | ØNH | |
| — | 123 | Ø | $NH_2$ | |
| 718 | 124 | 2-furanyl | ØNH | foam |

EXAMPLES 125–126

General Procedure for the Preparation of 4-Amino- and 4-Arylamino-5-aryl-7-(5-deoxy-1-β-d-ribofuranosyl)pyrrolo[2,3-d]pyrimidines The above-identified compounds were prepared as described in Example 122–124 from the 4-amino- or 4-arylamino-5-iodo-7-(5-deoxy-1-β-D-ribofuranosyl)pyrrolo[2,3-d]pyrimidine and an arylboronic acid.

The compounds in Table IX were prepared by this procedure:

TABLE IX

| GPl # | Example | B' | D | F | G | M.P. (°C.) |
|---|---|---|---|---|---|---|
| 684 | 125 | $CH_3$ | Phenyl | $NH_2$ | H | 106–109 |
| 683 | 126 | $CH_3$ | Phenyl | NH-Ø | H | 207–208 |

EXAMPLE 127

Preparation of 4-Chloro-5-iodo-7-(6-deoxy-1-β-D-allofuranosyl)pyrrolo[2,3-d]pyrimidine The above-identified compound was prepared according to the general procedure used for Examples 65–81; m.p. 211°–213° C.

EXAMPLE 128

Preparation of 4-Amino-5-iodo-7-(6-deoxy-1-β-D-allofuranosyl)pyrrolo[2,3-d]pyrimidine The 4-chloro compound, Example 127, was heated in a steel bomb with methanolic ammonia at 120° C. for 12 hours followed by the usual work up (see Example 85). The product was obtained as a white crystalline solid; m.p. 206°–208° C.

EXAMPLES 129–130

General Procedure for the Preparation of 4-Amino-5-halo-6-(5,6-dideoxy-1-β-D-allofuranosyl)pyrrolo[2,3-d]pyrimidine The above-described compounds were prepared by the general procedures for Examples 65 to 81.

The compounds obtained by this procedure are listed in Table X.

TABLE X

| GPl # | Example | B' | D | F | G | M.P. (°C.) |
|---|---|---|---|---|---|---|
| 693 | 129 | $CH_2CH_3$ | Br | $NH_2$ | H | 229–230 |
| 691 | 130 | $CH_2CH_3$ | I | $NH_2$ | H | 233–234 |

EXAMPLE 131

Preparation of 4-Amino-3-bromopyrazolo[3,4-d]pyrimidine

The above-identified compound was prepared as described: Leonova, T.; Yashunskii, V.; *Khim. Get. Soed.*, 1982, 982.

EXAMPLE 132

Preparation of 4-Amino-3-(cyanomethyl)pyrazolo[3,4-d]pyrimidine

The above-identified compound was prepared as described: Carboni, R.,; Coffman, D.,; Howard, E.; *J. Am. Chem. Soc.*, 1958 80:2838.

EXAMPLE 133

Preparation of 4-Amino-3-cyanopyrazolo[3,4-d]pyrimidine

The above-identified compound was prepared as described: Taylor, E.; Abul-Hsan, A.; *J. Org. Chem.*, 1966, 31:342.

EXAMPLE 134

Preparation of 4-Amino-3-phenylpyrazolo[3,4-d]pyrimidine

The above-identified compound was prepared from trimethyl orthobenzoate as described: Kobayashi, S.; *Chem. Pharm. Bull.* (Jap.) 1973, 21:941.

EXAMPLES 135–139

General Procedure for the Preparation of Aryl Thiomorpholides

A mixture of the aromatic carboxaldehyde (0.1 mole), sulfur (4.8 g, 0.15 mole) and morpholine (18 mL, 0.15 mole) was heated at 180° C. for 3"5 hours then cooled and diluted with $H_2O$. The solid was collected by filtration or, if oily, extracted with $CH_2Cl_2$, dried ($Na_2SO_4$) and concentrated. The crude product was from alcohol, alcohol-$H_2O$ mixtures or chromatographed over $SiO_2$.

The compounds in Table XI were prepared by this procedure:

TABLE XI

| Example | Aryl | M.P. (°C.) |
|---|---|---|
| 135 | 4-$CH_3$Oφ | 95–98° |
| 136 | 4-Clφ | 137–140° |
| 137 | 2-Brφ | — |
| 138 | 2-thienyl | 75–77° |
|  | 3-thienyl | 84–87° |
| 139 | 3-$CH_3$Oφ | 134–139° |

EXAMPLES 140–144

General Procedure for the Preparation of 5-Amino-3-aryl-4-cyanopyrazoles

The above-identified compounds were prepared from the corresponding aryl thiomorpholides (Examples 135–139) following the general procedure described: Tominaga, Y.,; et al.; *J. Heterocyclic Chem.*, 1990, 27:647.

The compounds listed in Table XII were prepared by this procedure:

TABLE XII

| Example | Aryl | M.P. (°C.) |
|---|---|---|
| 140 | 4-$CH_3$Oφ | 155–160° |
| 141 | 4-Clφ | 218–222° |
| 142 | 2-Brφ | — |
| 143 | 2-thienyl | 260–265° |
| 144 | 3-thienyl | 229–231° |

EXAMPLES 145–148

General Procedure for the Preparation of 5-Amino-3-aryl-4-carboxamidopyrazoles

The above-identified compounds were obtained from the corresponding cyano compounds (Example 140–144) following the general procedure described: Kobayashi, S.; *Chem. Pharm. Bull.* (Jap.), 1973, 21:941.

The compounds listed in Table XIII were prepared by this procedure:

TABLE XIII

| Example | Aryl | M.P. (°C.) |
|---|---|---|
| 145 | φ | 203–205° |
| 146 | 4-CH₃Oφ | — |
| 147 | 4-Clφ | 210–215° |
| 148 | 2-Brφ | — |

EXAMPLE 149–154

General Procedure for the Preparation of 4-Amino-3-arylpyrazolo[3,4-d]pyrimidines A mixture of the 5-amino-3-aryl-4-cyanopyrazole and formamide (5 ml/g) under $N_2$, was refluxed (190°–200° C.) with stirring for 4 hours. The cooled mixture was diluted with $H_2O$ and the solid collected by filtration. The crude products were used directly for subsequent steps or purified by recrystallization. The compounds listed in Table XIV were prepared by this procedure.

TABLE XIV

| Example | Aryl | M.P. (°C.) |
|---|---|---|
| 149 | φ | >220 |
| 150 | 4-CH₃Oφ | >220 |
| 151 | 4-Clφ | >220 |
| 152 | 2-Brφ | >220 |
| 153 | 2-Thienyl | >220 |
| 154 | 3-Thienyl | >283 (dec.) |

EXAMPLES 155–158

General Procedure for the Preparation of 3-Arylpyrazolo-[3,4-d]pyrimidin-4-ones from 5-Amino-3-aryl-4-carboxamidopyrazoles A mixture of the 5-amino-3-aryl-4-carboxamidopyrazole and formamide (5 ml/g) was refluxed at 190°–200° C. for 2 hours, cooled and diluted with $H_2O$. The solid was collected by filtration and dried under vacuum. Further purification was effected by dissolving the compound in dilute sodium hydroxide, followed by charcoal treatment and precipitation with acetic acid.

The compounds listed in Table XV were prepared by this procedure:

TABLE XV

| Example | Aryl | M.P. (°C.) |
|---|---|---|
| 155 | φ | >200° |
| 156 | 4-CH₃Oφ | >220° |
| 157 | 4-Clφ | >220° |
| 158 | 2-Thienyl | >220° |

EXAMPLES 159–160

General Procedure for Preparation of 3-Arylpyrazolo [3,4-d]pyrimidin-4-ones from 4-Amino-3-aryl pyrazolo[3,4-d]pyrimidines To a well stirred slurry of the 3-aryl-4-aminopyrazolo[3,4-d]primidine (25 mmoles) in 175 ml of 9% HCl at 0 to 5° C., was added dropwise, over 45 minutes, an aqueous solution of sodium nitrite (15.0 g in 30 ml). The mixture was allowed to warm to room temperature and solid sodium nitrite (5.0 g) was added. After 15 minutes the mixture was cautiously heated to boiling (foaming!), then cooled. The product was collected by filtration, rinsed with $H_2O$ and dried at 50° C. under vacuum.

The compounds listed in Table XVI were prepared by this procedure:

TABLE XVI

| Example | Aryl | M.P. (°C.) |
|---|---|---|
| 159 | φ | >220° |
| 160 | 2-thienyl | >220° |

EXAMPLES 161–163

General Procedure for the Preparation of N -Aryl and $N^4$-Alkyl substituted 4-amino-3-aryl-pyrazolo [3,4-d]pyrimidines A mixture of the 3-arylpyrazolo[3,4-d]pyrimidin-4-one (15 mmoles), $POCl_3$ (18 ml, 195 mmoles) and diethylaniline (5 ml, 31 mmoles) was refluxed under $N_2$ for 4 hours then concentrated under vacuum. The residue was decomposed by addition of ice and extracted (4x) with 3:1 ether-ethyl acetate. The combined organic extracts were washed with water and dried ($Na_2SO_4$). The solution was concentrated under vacuum and the crude 4-chloro-3-arylpyrazolo[3,4-d]pyrimidine (50–70% yield) was added to a solution of amine (2.2 equivalents) in EtOH (25 ml/mmole chloro compound). The mixture was heated to reflux for 30 minutes then cooled and the product collected by filtration and rinsed with EtOH. Recrystallization from alcohol-ethyl acetate mixtures gave the title compounds.

The compounds listed in Table XVII were prepared by this procedure.

TABLE XVII

| Example | 3-Aryl | 4-Arylamino | M.P. (°C.) |
|---|---|---|---|
| 161 | φ | φ | 229–232° |
| 162 | φ | 4-ClφNH | 232–233° |
| 163 | φ | 4-CH₃OφNH | 218–220° |

EXAMPLE 164

Preparation of 3-Bromopyrazolo[3,4-d]pyrimidin-4-one

The above-identified compound was prepared as described: Chu, I.; Lynch, B.; *J. Med. Chem.*, 1975, 18:161.

EXAMPLE 165

Preparation of 3-Bromo-1-(2.3,5-O-tribenzoyl-1-β-D-ribofuranosyl)pyrazolo[3,4-d]pyrimidin-4-one The above-identified compound was prepared as described: Cottam, H.; Petrie, C.; McKernan, P.; Goebel, R.; Dailey, N.; Davidson, R.; Robins, R.; Revankar, G.; *J. Med. Chem.*, 1984, 27:1120.

EXAMPLE 166

Preparation of 3-Substituted-4-chloro-1-(2,3,5,-O-tribenzoyl-1-β-D-ribofuranosyl)pyrazolo[3,4-d] pyrimidin-4-ones The above-identified compounds may be prepared from the corresponding pyrazolo[3,4-d]-pyrimidones analogously to the procedure described in Example 2.

EXAMPLES 167 TO 169

General Procedure for Preparation of 3-Substituted 4-amino- and 4-(arylamino)-1-(1-β-D-ribofuranosyl) pyrazolo[3,4-d]pyrimidines To a slurry of the 3-substituted-4-chloropyrazolo[3,4-d] pyrimidine nucleoside tribenzoate (1.0 eq) (Example 166) in a mixture of EtOH and THF, was added ethanolic ammonia or the amine (1.5 eq) and $Et_3N$ (3.5 eq). The reaction rapidly became homogenous and after 0.5–12 hours, was evaporated. The residue was dissolved in $CH_2Cl_2$, washed with aqueous $K_2CO_3$ then $H_2O$ and the solution dried ($Na_2SO_4$). After evaporation, the residue was recrystallized or chromatographed on $SiO_2$ gel using $CH_2Cl_2$-MeOH mixtures. The resulting tribenzoate of the title compound was deblocked by stirring in methanolic NaOMe. The mixture was neutralized with amberlite IR-120(+) resin, filtered and evaporated. The residue was recrystallized to give the title compounds.

Examples 167 to 169 listed in Table XVIII were prepared by procedure:

TABLE XVIII

| GP1-# | Example | 3-  | 4-           | m.p. (°C.) |
|-------|---------|-----|--------------|------------|
| 596   | 167     | I   | $NH_2$       | 180–185°   |
| 469   | 168     | Br  | N-in-dolinyl | 195–196°   |
| 536   | 169     | $CH_3$ | $NH_2$    | 241–242°   |

EXAMPLE 170

Preparation of 4-(N-Indolinyl)-1-(1-β-D-ribofuranosyl)pyrazolo[3,4-d]pyrimidine

A solution of the bromide (Example 168) (351 mg, 0.78 mmol) ethanol containing 300 mg 10% Pd-C and Raney Ni was hydrogenated at 40 psi until the reaction was complete as judged by TLC. The mixture was filtered, the filtrate concentrated and the product collected by filtration to give the title compound: 120 mg (42%); m.p. 215°–219°.

EXAMPLE 171

Preparation of 3-Bromo-1-[2,3-O-(1-methylethylidene)-1-β-D-ribofuranosyl]pyrazolo[3,4-d]pyrimidin-4-one Crude 3-bromoallopurinol riboside (prepared from 33.0 g of tribenzoate and NaOMe/MeOH (Example 83) was added to a cold (5° C.), stirred solution of 1M ethanolic HCl (6.5 ml) and dimethoxypropane (20 ml) in 1.1 L of $Me_2CO$. The mixture rapidly became homogenous and was stirred 45 minutes until complete (TLC). To the solution was added $Na_2CO_3$ (5.0 g), concentrated $NH_4OH$ (5 ml) and the mixture was stirred until the pH reached 6–7. The reaction was filtered and evaporated to a solid. The residual solid was dissolved in 300 ml of boiling EtOH and the solution concentrated by distilling EtOH to a final volume of 150 ml. The solution was chilled overnight and the solid collected by filtration and rinsed with cold EtOH. After drying (50° C.), 16.7 g (86%) of the title compound were obtained; m.p. 221°–224° C.

EXAMPLE 172

Preparation of 3-Bromo-1-[2,3-O-(1-methylethylidene)-5-O-(4-methylbenzenesulfonyl)-1-β-D-ribofuranosyl]pyrazolo-[3,4-d]pyrimidin-4-one To a solution of the isopropylidene alcohol (Example 171) (3.0 g, 7.74 mmol) in pyridine (18 ml) at 0° C. was added p-toluenesulfonyl chloride (1.77 g, 9.30 mmol). The reaction was held at 0° C. for 3 hours then poured into 160 ml of cold $H_2O$ with stirring. The mixture was allowed to settle, the $H_2O$ decanted and the residue dissolved in $CH_2Cl_2$. The $Cl_2Cl_2$ solution was washed with 0.5N $H_2SO_4$, 5% aqueous $K_2CO_3$ and dried ($Na_2SO_4$). After evaporation under vacuum, 4.03 g (96% yield) of the title compound were obtained as a foam.

EXAMPLE 173

Preparation of 1-[5-Azido-5-deoxy-2,3-O-(1-methylethylidene)-1-β-D-ribofuranosyl]-3-bromopyrazolo-[3,4-d]pyrimidin-4-one To a warm stirred solution of $NaN_3$ (7.69 g, 0.12 moles) in DMSO (70 ml) was added the tosylate (Example 172) (16.0 g, 0.03 mol). The solution was rapidly heated to 80° C. and maintained at this temperature for 45 minutes. After cooling, the reaction mixture was added with stirring to $H_2O$ (600 ml). The mixture was extracted 4x with $CHCl_3$ (75 ml) and the combined $CHCl_3$ extracts were washed with $H_2O$, dilute brine, dried ($Na_2SO_4$) and concentrated to give 11.0 g of a white foam. TLC (9:1 $CH_2Cl_2$-MeOH on $SiO_2$) indicated a mixture of three products in the approximate ratio of 1:2:1. The middle spot was subsequently determined to be the desired azide.

The mixture was purified by chromatography on a 10×15 cm column of $SiO_2$ eluting with 1% $Me_2CO$ in $CH_2Cl_2$ then increasing concentrations of $Me_2CO$. The first product eluted with 4% acetone. $^{13}$C-NMR indicated a lack of tosyl and azide functions at C-5'. Chemical shifts of the ribose C5' suggested a cyclonucleoside. The desired azide eluted with 6% $Me_2CO$. Its identity was confirmed by $^1$H and $^{13}$C NMR. Further elution afforded the third product which appeared by $^{13}$C-NMR to also be a cyclonucleoside.

The fractions containing the desired product (middle TLC spot) were combined and evaporated to give the title compound; 5.90 g (48% yield), m.p. 168° C. (d).

EXAMPLE 174

Preparation of 3-Amino-1-[2,3-O-(1-methylethylidene)-1-β-D-ribofuranosyl]pyazolo[3,4-d]pyrimidin-4-one A mixture of bromide (Example 171) (2.35 g, 6.1 mmol) CuCl (88 mg) and Cu (101 mg) in MeOH (45 ml) was placed in a bomb and saturated with gaseous $NH_3$. The bomb was sealed and heated to 110° C. for 10 hours. After cooling, the bomb was opened, the contents filtered and the filtrate evaporated. The residue was chromatographed on $SiO_2$ gel using 9:1 $CH_2Cl_2$-MeOH. The appropriate fractions were combined and evaporated to yield the title compound as a solid; 2.1 g (98% yield); m.p. 142°–144° C.

EXAMPLE 175

Preparation of 3-Iodo-1-[2,3-O-(1-methylethylidene)-1-β-D-ribofuranosyl]pyrazolo[3,4-d]pyrimidin-4-one A mixture of the amine (Example 174) (2.58 g, 8.0 mmole), isoamyl nitrite (30 ml), methylene iodide (20 ml) and $CH_3CN$ was refluxed under argon for 10 minutes. The cooled mixture was evaporated and chromatographed on $SiO_2$ gel using 2% methanol in methylene chloride. Appropriate fractions were combined and evaporated to give the title compound: 1.08 g (66% yield); m.p. >220° C.

EXAMPLE 176

Preparation of 3-Iodo-1-[2,3-O-(1-methylethylidene)-5-O-(4-methylbenzenesulfonyl)-1-β-D-ribofuranosyl]pyrazolo-[3,4-d]pyrimidin-4-one The above identified compound was prepared analogously to the procedure described for Example 172.

EXAMPLE 177

Preparation of 3-Iodo-1-[5-azido-5-deoxy-2,3-O-(1-methylethylidene)-1-β-D-ribofuranosyl]pyrazolo-[3,4-d]pyrimidin-4-one The above identified compound was prepared analogously to the procedure described for Example 173 in 45% yield; m.p. 203° C. (d).

EXAMPLE 178

Preparation of 3-Halo-4-chloro-1-[5-azido-5-deoxy-2,3-O-(1-methylethylidene) -1-β-D-ribofuranosyl)]pyrazolo[3,4-d]pyrimidine The above-identified compounds were prepared analogously to the procedure described for Example 2 from the pyrimidin-4-one (Example 173 or 177). The title compounds were obtained as unstable yellow oils and used immediately in the next step.

EXAMPLES 179 TO 181

General Procedure for the Preparation of 4-Amino and 4-hydrocarbyl-amino-1-(5-azido-5-deoxy-1-β-D-ribofuranosyl)pyrazolo[3,4-d]pyrimidines To a solution of the chloro azide (Example 178) (1 eq) in 1:1 THF-EtOH (10% w/v) was added to the amine (1.2–2.0 eq) and excess Et$_3$N (for the 4-amino compounds the solution was saturated with NH$_3$ gas). The resulting solution was stirred for 2–24 hours and checked for complete reaction by TLC (SiO$_2$; 9:1 CH$_2$Cl$_2$:Me$_2$CO).

The reactions using amines were worked up in the following manner. The reaction mixture was evaporated, the residue dissolved in CH$_2$Cl$_2$ and the solution washed with aqueous NaHCO$_3$, then H$_2$O and dried (Na$_2$SO$_4$). Concentration of the CH$_2$Cl$_2$ solution and chromatography of the residue over SiO$_2$ gel using CH$_2$Cl$_2$ Me$_2$CO mixtures gave the purified isopropylidene N$^4$-substituted compounds. The isopropylidene 4-amino compounds were isolated by evaporating the reaction mixture and recrystallizing the residue from EtOH.

The isopropylidene compounds were deblocked using the procedure described under Example 3.

The compounds in Table XIX (Examples 179 to 181) were prepared by this procedure:

TABLE XIX

| GP1-# | Example | D | F | m.p. (°C.) |
|---|---|---|---|---|
| 507 | 179 | Br | NH$_2$ | 169–170° |
| 501 | 180 | Br | N-indolinyl | 133–138° |
| — | 181 | I | NH$_2$ | 193–195° |

EXAMPLES 182 TO 185

General Procedure for the Preparation of 4-Amino- and 4-Substituted-amino-1-(5-amino-5-deoxy-1-β-D-ribofuranosyl)-3-halo-pyrazolo[3,4-d]pyrimidines and Their Hydrochloride Salts A solution of the azide (Examples 179 to 181) (1.0 equivalent) and triphenylphosphine (1.5 equivalents) in pyridine (5 ml/g of azide) was stirred for 2 hours and checked by TLC (9:1 CH$_2$Cl$_2$-MeOH) for completion. To the reaction mixture was added concentrated NH$_4$OH (1.25 ml/g of azide) and the solution stirred overnight. The solution was evaporated to dryness, slurried in Et$_2$O, filtered (3x) and the insoluble residue dried under vacuum. The resulting solid was recrystallized or converted to its HCl salt (0.1N HCl, EtOH) and crystallized to give the title compounds.

The compounds in Table XI (Examples 182–185) may be prepared by this procedure:

TABLE XX

| GP1-# | Example # | D | F | m.p. (°C. (HCl salt)) |
|---|---|---|---|---|
| 515 | 182 | Br | NH$_2$ | >230° |
| 516 | 183 | Br | N-indolinyl | 170° (broad) |
| 547 | 184 | I | NH$_2$ | 188° |
| 558 | 185 | Br | 1,4-piperazinyl[1] | 195° (broad) |

[1] a dimer

EXAMPLE 186

Preparation of 1,2,3-O-Triacetyl-5-deoxy-D-ribofuranoside

The above-identified compound was prepared as described: Snyder, J.; Serianni, A.; *Carbohydrate Research*, 1987, 163:169.

EXAMPLE 187

Preparation of 1,2,3-O-Triacetyl-5-azido-5-deoxy-D-ribofuranoside

To a cooled solution of 5-azido-5-deoxyribose (6.2 g, 0.035 mole) (Example 51) in 10 ml of pyridine was added acetic anhydride (18 ml) and the mixture stirred for 24 hours at room temperature. The mixture was concentrated under vacuum, the residue dissolved in CH2Cl$_2$ and the solution washed with 5% NaHCO$_3$. The organic layer was then washed with 0.5N H$_2$SO$_4$, dried (Na$_2$SO$_4$) and evaporated. The residue was filtered through a plug of SiO$_2$ gel (CH$_2$Cl$_2$) and the filtrate concentrated to afford the title compound, 9.0 g (98% yield) as a semisolid mixture of α and β isomers.

EXAMPLES 188–203

General Procedure for the Preparation of 5'-Substituted-3,4-disubstituted-pyrazolo[3,4-d]pyrimidine Nucleosides To a slurry of the 3,4-disubstituted pyrazolo[3,4-d]pyrimidine (5.0 mmol) in nitromethane, nitroethane or benzonitrile under N$_2$, was added the acyl-protected ribose (5.0–7.0 mmoles). To the stirred mixture, was added BF$_3$.Et$_2$O (7.0 mmoles) and the mixture was refluxed for 90 minutes, then cooled and evaporated under vacuum. If a 5'-deoxy derivative was used, Et$_3$N was added prior to the evaporation of the solvent (to complex BF$_3$. Et$_2$O).

The residue was taken up in CH$_2$Cl$_2$, filtered and chromatographed over SiO2 gel using CH$_2$Cl$_2$-MeOH gradients. Later fractions contained the N-2 isomer. Fractions containing the desired N-1 isomer were combined and evaporated to yield the title compounds as foams.

The compounds in Table XXI (Examples 188–203) were prepared by this procedure:

TABLE XXI

| Example # | B' | D | F | M.P. (°C.) |
|---|---|---|---|---|
| 188 | φCO$_2$CH$_2$ | CN | NH$_2$ | foam |
| 189 | φCO$_2$CH$_2$ | CH$_2$CN | NH$_2$ | foam |
| 190 | φCO$_2$CH$_2$ | φ | NHφ | foam |
| 191 | CH$_2$N$_3$ | Br | NH$_2$ | foam |
| 192 | CH$_2$N$_3$ | CN | NH$_2$ | foam |
| 193 | CH$_2$N$_3$ | CH$_2$CN | NH$_2$ | foam |
| 194 | CH$_2$N$_3$ | φ | NH$_2$ | foam |
| 195 | CH$_2$N$_3$ | 4-Clφ | NH$_2$ | foam |
| 196 | CH$_2$N$_3$ | 4-CH$_3$Oφ | NH$_2$ | foam |
| 197 | CH$_2$N$_3$ | 2-thienyl | NH$_2$ | foam |
| 198 | CH$_3$ | φ | NH$_2$ | foam |
| 199 | CH$_3$ | 4-CH$_3$Oφ | NH$_2$ | foam |
| 200 | CH$_3$ | 4-Clφ | NH$_2$ | foam |
| 201 | CH$_3$ | 2-thienyl | NH$_2$ | foam |
| 202 | CH$_3$ | 3-thienyl | NH$_2$ | foam |
| 203 | CH$_3$ | φ | NHφ | foam |

EXAMPLE 204

General Procedure for the Preparation of 3-Substituted 1-(5-azido-5-deoxy-2,3-O-diacetyl-1-β-D-ribo-furanosyl)-4-chloropyrazolo[3,4-d]pyrimidines, 5'-Deoxy Analogs and Protected 5'-Hydroxy Analogs The above identified compounds were prepared from the pyrazolo[3,4-d]pyrimidone esters analogously to the procedure described in Example 2 and were used immediately in the next step.

EXAMPLES 205–221

General Procedure for the Preparation of 3,4-Disubstituted-1-(5-azido-5-deoxy-1-β-D-ribofuranosyl))pyrazolo-[3,4-d]pyrimidines, 5'-Deoxy Analogs and 5'-Hydroxy Analogs The above identified compounds were prepared from the diesters analogously to the procedure described in Example 167–169. Methanolic NH$_3$ (method A) or NaOMe (method B) was used to deblock the acyl-protected nucleosides (Examples 188–204). In the case of the cyano-substituted compounds, these methods led to different products by further reaction of the cyano group. The title compounds were isolated by conventional techniques.

The compounds listed in Table XXII (Examples 205–221) were prepared by this procedure.

TABLE XXII

| Example | GP1-# | B' | D | F | Method | M.P. (°C.) |
|---|---|---|---|---|---|---|
| 205 | 612 | CH$_2$OH | CH$_2$CN | NH$_2$ | A | 220° (dec) |
| 206 | 613 | CH$_2$OH | CH$_2$C(=NH)OCH$_3$ | NH$_2$ | B | 75° (dec) |
| 207 | 695 | CH$_2$OH | Ø | NHØ | B | 220–224° |
| 208 | 507 | CH$_2$N$_3$ | Br | NH$_2$ | B | 172° (d) |
| 209 | 623 | CH$_2$N$_3$ | C(=NH)NH$_2$ | NH$_2$ | A | 203–206° |
| 210 | 624 | CH$_2$N$_3$ | CH$_2$CN | NH$_2$ | A | 153–156° |
| 211 | 641 | CH$_2$N$_3$ | Ø | NH$_2$ | B | 203–205° |
| 212 | 662 | CH$_2$N$_3$ | 4-Clφ | NH$_2$ | B | 175–177° |
| 213 | 666 | CH$_2$N$_3$ | 4-CH$_3$Oφ | NH$_2$ | B | 153–155° |
| 214 | 654 | CH$_2$N$_3$ | 2-Thienyl | NH$_2$ | B | 180–181° |
| 215 | 667 | CH$_2$N$_3$ | Ø | NHØ | B | 120–125° |
| 216 | 663 | CH$_3$ | Ø | NH$_2$ | B | 223–224° |
| 217 | 678 | CH$_3$ | 4-Clφ | NH$_2$ | B | 130–133° |
| 218 | 679 | CH$_3$ | 4-CH$_3$Oφ | NH$_2$ | B | 175–176° |
| 219 | 664 | CH$_3$ | 2-Thienyl | NH$_2$ | B | 174–175° |
| 220 | 685 | CH$_3$ | 3-Thienyl | NH$_2$ | B | 153–154° |
| 221 | 683 | CH$_3$ | Ø | NHØ | B | 207–208° |

EXAMPLES 222–229

General Procedure for the Preparation of 4-Amino- and 4-Arylamino-3-substituted-1-(5-amino-5-deoxy-1-β-D-ribofuranosyl)pyrazolo[3,4-d]pyrimidines and Their Salts The above-identified compounds were prepared from the 5'-azides (Examples 205–221) by catalytic hydrogenation as described in Examples 15–20 (method A) or triphenylphosphine followed by ammonium hydroxide as described in Examples 82-83 (method B). The salts were prepared by standard methods.

The compounds listed in Table XXIII were be prepared by these methods:

TABLE XXIII

| GP1-# | Example | 3- | 4- | Method | Salt | M.P. (°C.) |
|---|---|---|---|---|---|---|
| 515 | 222 | Br | NH$_2$ | B | HCl | >230° |
| 614 | 223 | H | NH$_2$ | A | HBr | 260–165° |
| 625 | 224 | CH$_2$CN | NH$_2$ | B | —[1] | 175° (d) |
| 642 | 225 | φ | NH$_2$ | A | HCl | 218–219 |
| 682 | 226 | 2-thienyl | NH$_2$ | B | HCl | >220° |
| 694 | 227 | 4-CH$_3$Oφ | NH$_2$ | A | —[1] | 222–225° |
| 701 | 228 | 4-Clφ | NH$_2$ | B | HCl | 189–194° |
| 704 | 229 | φ | NH$_4$ | A | CF$_3$CO$_2$H | 185–190° |

[1]Not a salt.

EXAMPLES 230–231

General Procedure for the Preparation of 4-Amino- and 4-Arylamino-1-(5-amino-2,3-O-diacetyl-5-deoxy-1-β-D-ribofuranosyl)-3-substitutedpyrazolo [3,4-d]pyrimidines A slurry of 10% Pd-C in a solution (MeOH or EtOH with THF, dioxane or EtOAc) of the 5'-azido-2',3'-diacetate nucleoside (Examples 191–198) is hydrogenated in a Parr shaker at 40 psi. After disappearance of the starting material (TLC), the mixture is filtered and concentrated under vacuum at a temperature of less than 40° C. The residual product is purified by recrystallization or HPLC.

The compounds listed in Table XXIV may be prepared by this method:

TABLE XXIV

| GP1-# | Example | D | F | C$_1$, C$_2$ | M.P. (°C.) |
|---|---|---|---|---|---|
| — | 230 | Br | NH$_2$ | OAc | — |
| — | 231 | φ | NHφ | OAc | — |

EXAMPLES 232–233

General Procedure for the Preparation of 3-Substituted-4-(1,1-dicarboethoxyalkyl)-1-(2,3,5-O-tribenzoyl-1-β-D-ribofuranosyl)pyrazolo [3,4-d] pyrimidines To a stirred solution of the diethyl(alkyl)malonate (0.10 mol) in dry DMF (100 ml) under N$_2$ was added 80% NaH in mineral oil (0.125 mol). After stirring (cooling) for 10 minutes, a solution of the 3-substituted-4-chloro-1-(2,3,5-tribenzoyl-1-β-D-ribofuranosyl)pyrazolo[3,4-d]pyrimidine (0.09 mol) (Example 178) in DMF (75 ml) was added dropwise. The solution was cooled and anhydrous trimethylamine was bubbled into the solution for 4 minutes. The solution was stirred for 3 hours at room temperature (heating may be required in some cases) then quenched with dilute acetic acid. The mixture was extracted with ether-ethyl acetate (9:1) and the organic extract dried ($Na_2SO_4$), concentrated and pumped under vacuum. The residue was chromatographed on $SiO_2$ gel with $CH_2Cl_2$-acetone mixtures and the appropriate fractions combined and evaporated to yield the title compounds. The identity of the compounds were confirmed by $^1H$ and $^{13}C$ NMR.

The compounds listed in Table XXV were prepared by this procedure:

TABLE XXV

| Example | D | F | M.P. (°C.) |
|---|---|---|---|
| 232 | Br | $CH(CO_2C_2H_5)_2$ | foam |
| 233 | Br | $C\phi(CO_2C_2H_5)_2$ | foam |

EXAMPLES 234–235

General Procedure for Preparation of 4-Alkyl, 4-Arylalkyl- and 3,4-disubstituted-1-(1-β-D-ribofuranosyl)pyrazolo[3,4-d]pyrimidines The diester (Examples 232–233) was dissolved in aqueous ethanolic sodium hydroxide and heated. The solution was neutralized with acetic acid, evaporated, extracted with hot ethanol and the extract then evaporated and recrystallized or evaporated on $SiO_2$ gel. The $SiO_2$ gel was loaded on a column of $SiO_2$ gel and the product eluted with $CH_2Cl_2$-MeOH mixtures. The appropriate fractions more combined and evaporated to yield the title compounds.

The compounds described in Table XXVI were prepared by the procedure:

TABLE XXVI

| GP-1-# | Example | D | F | M.P. (°C.) |
|---|---|---|---|---|
| 719 | 234 | Br | $CH_3$ | 204–205° |
|  | 235 | Br | $CH_2\phi$ | — |

EXAMPLES 236–237

General Procedure for Preparation of 3-Substituted-4-(1,1-dicarboethoxyalkyl)-1-(5-azido-5-deoxy-2,3-O-diacetyl-1-β-D-ribofuranosyl)pyrazolo[3,4-d] pyrimidines The above-identified compounds are prepared analogously by the procedure described in Examples 232–233 using the 3-substituted-(5-azido-5-deoxy-2,3-O-diacetyl-1-β-D-ribofuranosyl)-4-chloropyrazolo[3, 4-d]pyrimidine.

The compounds listed in Table XXVII may be prepared by this procedure:

TABLE XXVII

| Example | D | F | M.P. (°C.) |
|---|---|---|---|
| 236 | Br | $C\phi(CO_2C_2H_5)_2$ | — |
| 237 | Br | $CH(CO_2C_2H_5)_2$ | — |

EXAMPLES 238–239

General Procedure for Preparation of 4-Alkyl-, 4-Phenylalkyl-and 4-Substituted-3-Substituted-1-(5-azido-5-deoxy-1-β-D-ribofuranosyl)pyrazolo[3,4-d]-pyrimidines The above identified compounds are prepared analogously by the procedure described in Examples 234–235 from the 5'-azide esters described in Examples 236–237.

The following compounds listed in Table XXVIII may be prepared by this procedure:

TABLE XXVIII

| GP1-# | Example | D | F | M.P. (°C.) |
|---|---|---|---|---|
| — | 238 | Br | $CH_3$ | — |
| — | 239 | Br | $CH_2\phi$ | — |

EXAMPLES 240–241

General Procedure for the Preparation of 4-Alkyl-, 4-Phenylalkyl- and 3,4-Disubstituted-1-(5-amino-5-deoxy-1-β-D-ribofuranosyl) pyrazolo[3,4-d] pyrimidines The above-identified compounds may be prepared by reduction of the 5-azido ribosides listed in Examples 238–239 by catalytic hydrogenation as described in Examples 15–20 or by treatment with triphenylphosphine and ammonium hydroxide as described in Examples 182–185.

The compounds listed in Table XXIX are prepared by this procedure:

TABLE XXIX

| GP1-# | Example | D | F | M.P. (°C.) |
|---|---|---|---|---|
| — | 240 | Br | $CH_3$ | — |
| — | 241 | Br | $CH_2\phi$ | — |

EXAMPLES 242–243

General Procedures for the Preparation of 3-Substituted-1-(5-deoxy-2,3-O-diacetyl-1-β-D-ribofuranosyl) -4-(1,1-dicarboethoxyalkyl)pyrazolo [3,4-d]pyrimidines The above-identified compounds are prepared analogously to the procedure described in Examples 232–233 using 3-substituted-4-chloro-1-(5-deoxy-2,3-O-diacetyl-1-β-D-ribofuranosyl)pyrazolo[3,4-d]pyrimidines (Examples 198–203).

The compounds listed in Table XXX may be prepared by this procedure:

TABLE XXX

| GP1-# | Example | D | F | M.P. (°C.) |
|---|---|---|---|---|
| — | 242 | Br | CH(CO$_2$C$_2$H$_5$)$_2$ | — |
| — | 243 | Br | C(CO$_2$C$_2$H$_5$)$_2$CHφ | — |

EXAMPLES 244–245

General Procedure for Preparation of 4-Alkyl-, 4-Phenylalkyl-, or 4-Substituted-3-substituted-1-(5-deoxy-1-β-D-ribofuranosyl)pyrazolo[3,4-d] pyrimidines The above-identified compounds may be prepared from the esters (Examples 242–243) using the procedure described in Examples 234–235.

The compounds listed in Table XXXI may be prepared by this method:

TABLE XXXI

| GP1-# | Example | D | F | M.P. (°C.) |
|---|---|---|---|---|
| — | 244 | Br | CH$_2$CH$_2$φ | — |
| — | 245 | Br | CH$_2$φ | — |

By following the procedures described in the Detailed Description of the Invention and Examples 1 to 245 and using the appropriate starting materials and reagents, the following compounds are made:

4-Amino-7-(5-deoxy-1-β-D-ribofuranosyl)-5-vinylylpyrrolo[2,3-d]pyrimidine;

4-Amino-5-ethynyl-7-(5-deoxy-1-β-D-ribofuranosyl) pyrrolo[2,3-d]pyrimidine;

5-(2-Chlorophenyl)-7-(5-deoxy-1-β-D-ribofuranosyl)-4-phenylaminopyrrolo[2,3-d]pyrimidine;

5-(3-Chlorophenyl)-7-(5-deoxy-1-β-D-ribofuranosyl)-4-phenylaminopyrrolo[2,3-d]pyrimidine;

5-(4-Chlorophenyl)-7-(5-deoxy-1-β-D-ribofuranosyl)-4-phenylaminopyrrolo[2,3-d]pyrimidine;

5-(2-Methoxyphenyl)-7-(5-deoxy-1-β-D-ribofuranosyl)-4-phenylaminopyrrolo[2,3-d]pyrimidine;

5-(4-Methoxyphenyl)-7-(5-deoxy-1-β-D-ribofuranosyl)-4-phenylaminopyrrolo[2,3-d]pyrimdine;

5-(2-Furanyl)-7-(5-deoxy-1-β-D-ribofuranosyl)-4-phenylaminopyrrolo[2,3-d]pyrimidine;

7-(5-Deoxy-1-β-D-ribofuranosyl)-4-phenyamino-5-(2-pyridyl)pyrrolo[2,3-d]pyrimidine;

7-(5-Deoxy-1-β-D-ribofuranosyl)-4-phenylamino-5-(4-pyridyl)pyrrolo[2,3-d]pyrimidine.

7-(5-Deoxy-1-β-D-ribofuranosyl)-5-phenyl-4-(4-pyridylamino)pyrrolo[2,3-d]pyrimidine;

7-(5-Deoxy-1-β-D-ribofuranosyl)-5-phenyl-4-(2-pyridylamino)-pyrrolo[2,3-d]pyrimidine;

7-(5-Deoxy-1-β-D-ribofuranosyl)-5-phenyl-4-(1-piperazinyl)-pyrrolo[2,3-d]pyrimidine;

4-(2-Chlorophenyl)-7-(5-deoxy-1-β-D-ribofuranosyl)-5-phenylpyrrolo[2,3-d]pyrimidine;

4-(3-Chlorophenyl)-7-(5-deoxy-1-β-D-ribofuranosyl)-5-phenylpyrrolo[2,3-d]pyrimidine;

7-(5-Deoxy-1-β-D-ribofuranosyl)-5-phenyl-4-(2-thiazolyl-amino)pyrrolo[2,3-d]pyrimidine;

4-Cyclohexylamino-7-(5-deoxy-1-β-D-ribofuranosyl)-5-phenylpyrrolo[2,3-d]pyrimidine;

7-(5-Deoxy-1-β-D-ribofuranosyl)-5-phenyl-4-phenylthio-pyrrolo[2,3-d]pyrimidine;

4-Benzyl-7-(5-deoxy-1-β-D-ribofuranosyl)-5-phenyl-pyrrolo[2,3-d]pyrimidine;

7-(5-Deoxy-1-β-D-ribofuranosyl)-4-ethynyl-5-phenyl-pyrrolo[2,3-d]pyrimidine;

7-(5-Deoxy-1-β-D-ribofuranosyl)-4-methyl-5-phenyl-pyrrolo[2,3-d]pyrimidine;

4-Benzyl-7-(5-deoxy-1-β-D-ribofuranosyl)-5-iodopyrrolo[2,3-d]pyrimidine;

7-(5-Deoxy-1-β-D-ribofuranosyl)-5-iodo-4-methyl-pyrrolo[2,3-d]pyrimidine;

7-(5-Deoxy-1-β-D-ribofuranosyl)-5-phenyl-4-phenylamino-pyrrolo[2,3-d]pyrimidine;

4-Amino-5-phenyl-7-(1-β-D-ribofuranosyl)pyrrolo[2,3-d]pyrimidine;

4-Amino-7-(5-deoxy-5-mercapto-1-β-D-ribofuranosyl)-5-iodopyrrolo[2,3-d]pyrimidine;

7-(5-Deoxy-5-mercapto-1-β-D-ribofuranosyl)-5-iodo-4-phenylaminopyrrolo[2,3-d]pyrimidine;

7-(5-Deoxy-5-mercapto-1-β-D-ribofuranosyl)-5-phenyl-4-phenylaminopyrrolo[2,3-d]pyrimidine;

7-(5-Amino-5-deoxy-1-β-D-ribofuranosyl)-5-phenyl-4-phenylaminopyrrolo[2,3-d]pyrimidine;

7-(5,6-Dideoxy-1-β-D-allofuranosyl)-5-iodo-4-phenylaminopyrrolo[2,3-d]pyrimidine;

7-(5,6-Dideoxy-1-β-D-allofuranosyl)-5-phenyl-4-phenylaminopyrrolo[2,3-d]pyrimidine;

4-Amino-7-(5,6-dideoxy-1-β-D-allofuranosyl)-5-phenyl-pyrrolo[2,3-d]pyrimidine;

4-Amino-7-(5-deoxy-5-fluoro-1-β-D-ribofuranosyl)-5-iodopyrrolo[2,3-d]pyrimidine;

4-Amino-7-(5-deoxy-5-chloro-1-β-D-ribofuranosyl) pyrrolo[2,3-d]pyrimidine;

7-(5-Deoxy-5-fluoro-1-β-D-ribofuranosyl)-5-phenyl-4-phenylaminopyrrolo[2,3-d]pyrimidine;

4-Amino-7-(6-azido-5,6-dideoxy-1-β-D-allofuranosyl)-5-iodopyrrolo[2,3-d]pyrimidine;

7-(6-Azido-5,6-dideoxy-1-β-D-allofuranosyl)-5-phenyl-4-phenylaminopyrrolo[2,3-d]pyrimidine;

4-Amino-7-(6-amino-5,6-dideoxy-1-β-D-allofuranosyl)-5-iodopyrrolo[2,3-d]pyrimidine;

7-(6-Amino-5,6-dideoxy-1-β-D-allofuranosyl)-5-phenyl-4-phenylaminopyrrolo[2,3-d]pyrimidine;

5-(2-Methoxyphenyl)-7-[1-β-D-ribofuranosyl]-4-phenylaminopyrrolo[2,3-d]pyrimidine;

4-Amino-5-bromo-7-(5,6-didehydro-5,6-dideoxy-1-β-D-allofuranosyl)pyrrolo[2,3-d]pyrimidine;

7-(5,6-Didehydro-5,6-dideoxy-1-β-D-allofuranosyl)-5-phenyl-4-phenylaminopyrrolo[2,3-d]pyrimidine;

4-Amino-1-(5-amino-5-deoxy-1-β-D-ribofuranosyl)-3-methoxy-pyrazolo[3,4-d]pyrimidine;

4-Amino-1-(5-amino-5-deoxy-1-β-D-ribofuranosyl)-3-phenoxypyrazolo[3,4-d]pyrimidine;

4-Amino-1-(5-amino-5-deoxy-1-β-D-ribofuranosyl)-3-phenylthiopyrazolo[3,4-d]pyrimidine;

4-Amino-1-(5-amino-5-deoxy-1-β-D-ribofuranosyl)-3-methylthiorpyrazolo[3,4-d]pyrimidine;

4-Amino-1-(5-amino-5-deoxy-1-β-D-ribofuranosyl)-3-chloropyrazolo[3,4-d]pyrimidine;

4-Amino-1-(5-amino-5-deoxy-1-β-D-ribofuranosyl)-3-cyclopropylpyrazolo[3,4-d]pyrimidine;

4-Amino-1-(5-amino-5-deoxy-1-β-D-ribofuranosyl)-3-dimethylamino-pyrazolo[3,4-d]pyrimidine;

4-Amino-1-(5-amino-5-deoxy-1-β-D-ribofuranosyl)-3-fluoro-pyrazolo[3,4-d]pyrimidine;

4-Amino-1-(5-amino-5-deoxy-1-β-D-ribofuranosyl)-3-(3-pyridyl)pyrazolo[3,4-d]pyrimidine;

1-(5-Amino-5-deoxy-1-β-D-ribofuranosyl)-4-(3-chlorophenyl)-3-(4-methoxyphenyl)pyrazolo[3,4-d]pyrimidine;

1-(5-Amino-5-deoxy-1-β-D-ribofuranosyl)-4-(4-chlorophenyl)-3-(4-methoxyphenyl)pyrazolo[3,4-d]pyrimidine;

1-(5-Amino-5-deoxy-1-β-D-ribofuranosyl)-4-(4-ethoxyphenyl)-3-(4-methoxyphenyl)pyrazolo[3,4-d]pyrimidine;

1-(5-Amino-5-deoxy-1-β-D-ribofuranosyl)-4-(3-carboxamidophenyl-amino)-3-(4-methoxyphenyl)pyrazolo[3,4-d)pyrimidine;

1-(5-Amino-5-Deoxy-1-β-D-ribofuranosyl)-4-(2-furanyl)-3-(4-methoxyphenyl)pyrazolo[3,4-d]pyrimidine;

1-(5-Deoxy-1-β-D-ribofuranosyl)-3-(4-methoxyphenyl)-4-(phenylamino)pyrazolo[3,4-d]pyrimidine;

1-(5-Deoxy-1-β-D-ribofuranosyl)-3-(3-methoxyphenyl)-4-(phenylamino)pyrazolo[3,4-d]pyrimidine;

1-(5-Deoxy-1-β-D-ribofuranosyl)-3-(2-pyridyl)-4-(phenylamino)pyrazolo[3,4-d]pyrimidine;

1-(5-Deoxy-1-β-D-ribofuranosyl)-3-(4-methoxyphenyl)-4-(4-pyridylamino)pyrazolo[3,4-d]pyrimidine;

1-(5-Deoxy-1-β-D-ribofuranosyl)-3-(3-methoxyphenyl)-4-(4-pyridylamino)pyrazolo[3,4-d]pyrimidine;

1-(5-Deoxy-1-β-D-ribofuranosyl)-3-(2-pyridyl)-4-(4-pyridylamino)pyrazolo[3,4-d]pyrimidine;

1-(5-deoxy-1-β-D-ribofuranosyl)-3-(4-methoxyphenyl)-4-(2-methoxyphenylamino)pyrazolo[3,4-d]pyridimine;

1-(5-Deoxy-1-β-D-ribofuranosyl)-3-(3-methoxyphenyl)-4-(2-methoxyphenylamino)pyrazolo[3,4-d]pyridimine;

1-(5-Deoxy-1-β-D-ribofuranosyl)-3-(4-pyridyl)-4-(2-methoxyphenylamino)pyrazolo[3,4-d]pyridimine;

1-(5-Deoxy-1-β-D-ribofuranosyl)-3-(4-methoxyphenyl)-4-(2-imidazolylamino)pyrazolo[3,4-d]pyrimidine;

1-(5-Deoxy-1-β-D-ribofuranosyl)-3-(3-methoxyphenyl)-4-(2-imidazolylamino)pyrazolo[3,4-d]pyrimidine;

1-(5-Deoxy-1-β-D-ribofuranosyl)-3-(2-pyridyl)-4-(2-imidazolylamino)pyrazolo[3,4-d]pyrimidine;

1-(5-Deoxy-1-β-D-ribofuranosyl)-3-(2-pyrazinyl)-4-phenylaminopyrazolo[3,4-d]pyrimidine;

1-(5-Deoxy-1-β-D-ribofuranosyl)-3-(2-pyrazinyl)-4-(N-indolinyl)pyrazolo[3,4-d]pyrimidine;

1-(5,6-Dideoxy-1-β-D-allofuranosyl)-3-phenyl-4-phenylaminopyrazolo[3,4-d]pyrimidine;

4-Amino-1-(5,6-dideoxy-1-β-D-allofuranosyl)-3-iodopyrazolo[3,4-d]pyrimidine;

1-(5-Deoxy-1-β-D-ribofuranosyl)-3-phenyl-4-phenylthiopyrazolo[3,4-d]pyrimidine;

1-(5-Amino-5-deoxy-1-β-D-ribopuranosyl)-3-bromo-4-methylpyrazolo[3,4-d]pyrimidine;

1-(5-Amino-5-deoxy-1-β-D-ribofuranosyl)-4-methyl-3-iodopyrazolo[3,4-d]pyrimidine;

7-(5-Deoxy-β-D-ribofuranosyl)-5-iodo-4-methylpyrrolo[2,3-d]pyrimidine;

4-Methyl-3-phenyl-1-(1-β-D-ribofuranosyl)pyrazolo[3,4-d]pyrimidine;

1-(5-Deoxy-1-β-D-ribofuranosyl)-3-phenyl-4-(phenylmethyl)pyrazolo[3,4-d]pyrimidine; and 7-(5-Amino-5-deoxy-1-β-D-ribofuranosyl)-5-bromo-4-chloropyrrolo[2,3-d]pyrimidine(GP-1-608).

EXAMPLE A

INHIBITION OF ADENOSINE KINASE ACTIVITY

Inhibition of enzyme activity was determined using a 0.1 ml assay mixture containing 50 mM Tris-maleate, pH 7.0, 0.1% (w/v) BSA, 1 mM ATP, 1 mM $MgCl_2$, 0.5 µM [U-14C] adenosine (500 mCi/mmol) and 0.1 g of purified pig heart adenosine kinase. Different concentrations of the test compounds were incubated in the assay mixture for 20 min. at 37° C. From each reaction mixture, 20 µl portions were removed and spotted on 2 $cm^2$ pieces of Whatman DE81 filter paper. The papers were then washed to remove [$^{14}$C] adenosine in 1 mM ammonium formate followed by deionized water and finally 95% ethanol. The papers were dried, and [$^{14}$C]AMP measured by scintillation counting. Activities were determined from the amount of [$^{14}$C]AMP formed.

$A_1$ receptor binding affinity was determined using 0.5 ml mixture containing 50 mM Tris HCl, pH 7.4, 1 nM [$^3$H]CHA and 0.5 mg of neuronal membrane incubated with different concentrations of the test compound for 60 min at 37° C. The reaction was stopped and unbound [$^3$H]CHA removed by rapid filtration through Whatman GF/B filters. The filter papers were then solubilized and bound ($^3$H]CHA determined by scintillation counting.

Inhibition of adenosine deaminase activity was determined spectrophotometrically using a 1 ml assay mixture containing 50 mM potassium phosphate, pH 7.0, 1 mM ADP, 2.5 mM alpha-ketoglutarate, 15 units glutamic dehydrogenase, 0.125 mM NADH, 80 µM adenosine and 0.002 units of calf intestinal mucosa adenosine deaminase. Different concentrations of the test compounds were incubated in the assay mixture for 10 min at 37° C. The reaction was monitored continuously for oxidation of NADH from the change in absorbance at 340 nm.

Illustrative of the invention, the compounds designated GP-1-515, GP-1-608, GP-1-683, GP-1-695, GP-1-718, GP-1-704, GP-1-665, and GP-1-667, were found to have an $IC_{50}$ of less than 10 nM in the adenosine kinase inhibition assay. The compound GP-1-515 was found to be much less potent in the $A_1$ receptor assay and in the adenosine deaminase inhibition assay, having an $IC_{50}$ greater than 100 µM in the $A_1$ receptor assay and an $IC_{50}$ greater than 1000 µM in the adenosine deaminase inhibition assay.

EXAMPLE B

ADENOSINE KINASE INHIBITION IN INTACT CELLS

Inhibition of adenosine kinase in intact cells was determined from the amount of incorporation of radioisotope from adenosine into the adenylates (AMP, ADP and ATP) in the presence of adenosine deaminase inhibition. Capillary endothelial cells from bovine heart were incubated for 60 min. with 20 µM 2'-deoxycoformycin, a potent adenosine deaminase inhibitor. Different concentrations of the test compounds were then added to the cells and incubated for 15 min. after which 5 µM ($^3$H]adenosine was added and the cells incubated for a further 15 min. The media was then discarded and the cells were treated with 50 µl 0.4 M perchloric acid, centrifuged and the supernatants neutralized with 100 µl alanine: freon (1:4). Radioisotope-labelled adenylates were separated by TLC on PEI cellulose plates developed in methanol:water (1:1) and incorporation of $^3$H determined by scintillation counting.

Illustrative of the invention, the compounds designated GP-1-515, GP-1-683 and GP-1-665 were shown to have an $IC_{50}$ of 9 nM, 73 nM and 4.5 nM, respectively, in the adenosine kinase inhibition assay in intact cells. (GP-1-665 is 4-(N-phenylamino)-3-phenyl-1-(5'deoxyribofuranosyl) pyrazolo[3,4-d]pyrimidine.)

EXAMPLE C

IMPROVED FUNCTIONAL RECOVERY IN ISOLATED HEARTS

The ability of a number of adenosine kinase inhibitors to improve the recovery of post-ischemic function was examined in an isolated guinea pig heart model.

Isolated guinea pig hearts were cannulated via the ascending aorta and attached to a perfusion apparatus according to the method of Langendorff. The hearts were perfused at a constant pressure of 60 cm of $H_2O$ with a modified Krebs-Hanseleit buffer (pH 7.4) at 37° C. Left ventricular developed pressures (LVDP) were monitored continuously using a latex balloon attached to a pressure transducer. Coronary flows were measured gravimetrically by timed collection of pulmonary effluent. Following equilibration of the hearts for a period of 30 minutes, the hearts were subjected to 45 minutes of low flow ischemia, by reducing the perfusion pressure to 10 cm of $H_2O$, and then reperfused for 30 minutes by restoring the pressure to its original level (60 cm of $H_2O$). The adenosine kinase inhibitors BP-1-238, GP-1-515 and GP1-547 were added to the perfusion buffer at the final concentrations specified. The results of these experiments are shown in Table A and demonstrate that adenosine kinase inhibitors enhance recovery of post ischemic function without affecting basal coronary flow.

TABLE A

| GP-1-# | Conc. (M) | Functional Recovery (% preischemic LVDP) | Preischemic Flow (ml/min/g) |
|---|---|---|---|
| Control (n = 14) | — | 66.0 ± 2.1 | 5.9 ± 0.2 |
| 238 (n = 6) | 5 | 81.3 ± 3.3* | 5.8 ± 0.3 |
| 515 (n = 6) | 0.3 | 79.0 ± 3.4* | 6.5 ± 0.3 |
| 547 | 0.3 | 79.0 ± 3.1* | 6.2 ± 0.3 |

*p < 0.05 vs. Control
Conc. = Concentration of test compound added to perfusion medium.

EXAMPLE D

EFFECT OF ADENOSINE KINASE INHIBITION ON ACUTE I.V. HEMODYNAMICS IN THE RAT

The ability of the adenosine kinase inhibitor GP-1-238 to show effects on blood pressure, heart rate or body temperature was compared in anesthetized and conscious rats. Sprague Dawley rats were anesthetized with pentobarbital and catheterized in the jugular vein and carotid artery. GP-1-238 (0.1-5 mg/kg/min) was infused intravenously in stepwise increments (0.2 ml/min x 5 minutes). The experiments in conscious rats were conducted in the same manner after rats had been catheterized and allowed to recover for 2 days following surgery. In conscious rats, in contrast to anesthetized animals, no hemodynamic effects were seen at doses which completely inhibited adenosine kinase in vivo See FIGS. 1A–1F.

EXAMPLE E

FUNCTIONAL BENEFIT OF GP-1-515 IN A PRECLINICAL MODEL OF STABLE ANGINA

GP-1-515, was evaluated for its ability to prevent cumulative cardiac dysfunction associated with repeated episodes of pacing-induced ischemia.

Anesthetized male dogs were instrumented to measure regional myocardial wall thickening during right atrial pacing (Young & Mullane, Am. J. Physio., 1991, 261:1570–1577). Animals were subjected to six repeated episodes of pacing. A continuous IV infusion of 1 μg/kg/min of GP-1-515 or saline (control) was administered post pace #1. The results of these experiments are shown in Table B and reveal that the adenosine kinase inhibitor, GP-1-515, attenuates the decline in wall thickening associated with pacing induced ischemia.

TABLE B

| | % of Non-Ischemic Wall Thickening | |
|---|---|---|
| Pace # | Saline (n = 3) | GP-1-515 (n = 4) |
| 1 | 33.3 ± 9.3 | 39.8 ± 3.2 |
| 2 | 40.5 ± 11 | 43.6 ± 12.0 |
| 3 | 27.4 ± 16 | 34.0 ± 19.0 |
| 4 | 19.2 ± 23 | 50.5 ± 21.3 |
| 5 | 22.6 ± 16 | 75.6 ± 19.4 |
| 6 | 13.7 ± 19 | 62.6 ± 17.1 |

EXAMPLE F

EFFICACY OF GP-1-515 IN A PRECLINICAL MODEL OF UNSTABLE ANGINA

GP-1-515 was tested in a canine model of platelet-induced coronary thrombosis (Folts, J., Circulation, 1991, 83[Suppl. IV]:IV-3-IV-14). In this model, platelets cyclically aggregate and embolize causing cyclic flow reductions (CFRs) that are quantitated by the frequency and the change in coronary blood flow from low point to peak with each cycle. The results are shown in Table C. Administration of the adenosine kinase inhibitor, GP-1-515, abolished CFRs in 3 of 8 animals and reduced both the frequency and the change in flow in those animals where CFRs were not abolished.

TABLE C

| | Control | 0.03 | 0.1 | 0.3 |
|---|---|---|---|---|
| CFR (freq.) | 5.2 ± 0.2 (n = 8) | 3.0 ± 0.6 (n = 7) | 3.4 ± 0.8 (n = 5) | 4.2 ± 0.6 (n = 5) |
| CFR (D flow) | 17 ± 1.7 (n = 8) | 10.1 ± 2.6 (n = 7) | 11.0 ± 2.1 (n = 5) | 14.1 ± 1.9 (n = 5) |
| N abolished / N total | 0/8 | 1/8 | 3/8 | 3/8 |

EXAMPLE G

INHIBITION OF NEUTROPHIL ADHERENCE TO FIBROBLASTS OR ENDOTHELIAL CELLS

The ability of an adenosine kinase inhibitor to affect neutrophil adherence to fibroblasts and endothelial cells was evaluated in a cell culture model.

Cultures of human dermal fibroblasts or human umbillical vein endothelial cells were washed and then incubated for 2 hours at 37° C. in a 5% $CO_2$ atmosphere in fresh medium containing different concentrations of the adenosine kinase inhibitors GP-1-272 and GP-1-456. These incubations were carried out in the presence of fMLP-stimulated human neutrophils isolated from whole blood ($1.25 \times 10^6$/ml) with or without adenosine deaminase (0.125 U/ml). At the end of the incubation, the medium was removed and the monolayers of fibroblasts or endothelial cells and adherent neutrophils were fixed by addition of formaldehyde (3.7%) and, after washing to remove non-adherent neutrophils, adherent neutrophils were stained with Weigart's hematoxylin and counted under a light microscope. The results depicted in FIGS. 2A and 2B show that the adenosine kinase inhibitors GP-1-272 and GP-1-456 respectively inhibit neutrophil adhesion to endothelial cells and that this inhibition is reversed by adenosine deaminase treatment.

EXAMPLE H

INHIBITION OF CONTRACTION IN ISOLATED ILEUM

The ability of adenosine kinase inhibition to affect stimulated contraction of muscle strips from the isolated ileum has been investigated.

Segments (about 1 cm) of longitudinal muscle were stripped from the guinea pig ileum, connected to isotonic force transducers and suspended in jacketed tissue baths containing Krebs-Ringer solution aerated with 95% $O_2$/5% $CO_2$. Parallel platinum electrodes were used to deliver electrical current at 1 minute intervals at a voltage adequate to induce contraction of 90% of maximal. The adenosine kinase inhibitors, GP-1-515 or GP-1-547 were added to the tissue baths at different concentrations, with or without either the adenosine receptor antagonist, 8-sulphophenyltheophylline (8SPT) or adenosine deaminase (ADA), and the effects on contraction monitored.

Figure 3A:
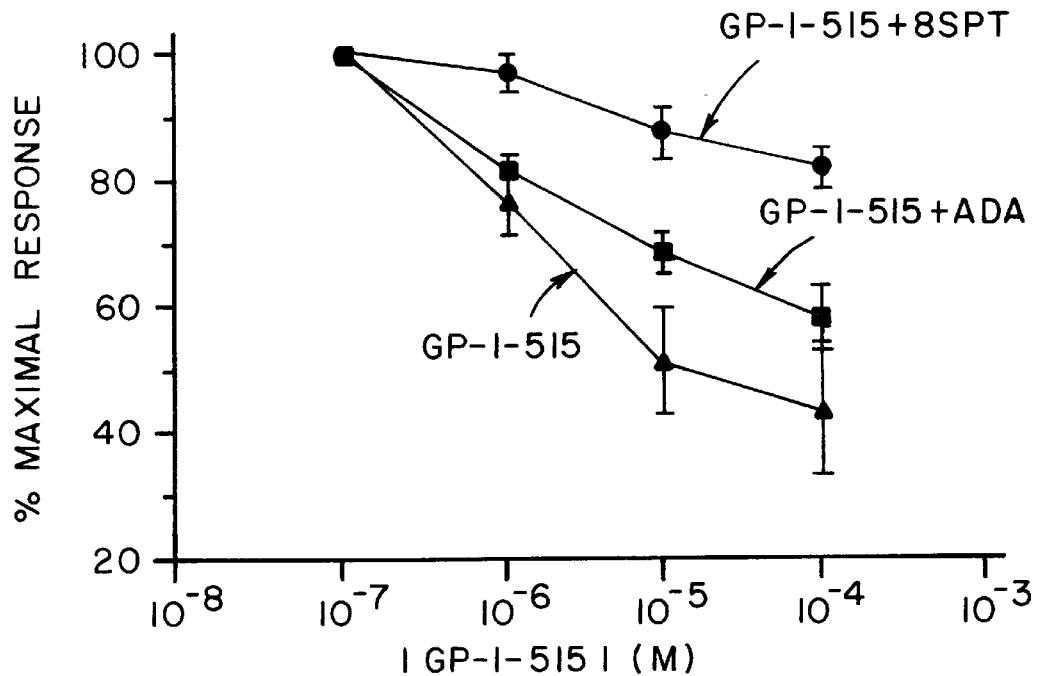
FIGS. 3A and 3B depict the dose-dependent inhibition of contraction in the isolated ileum by the adenosine kinase inhibitors (A) GP-1-515 and GP-1-547, respectively and the reversal of these inhibitions by co-treatment with the adenosine receptor antagonist, 8-sulfophenyltheophylline, or adenosine deaminase.
Figure 3B:
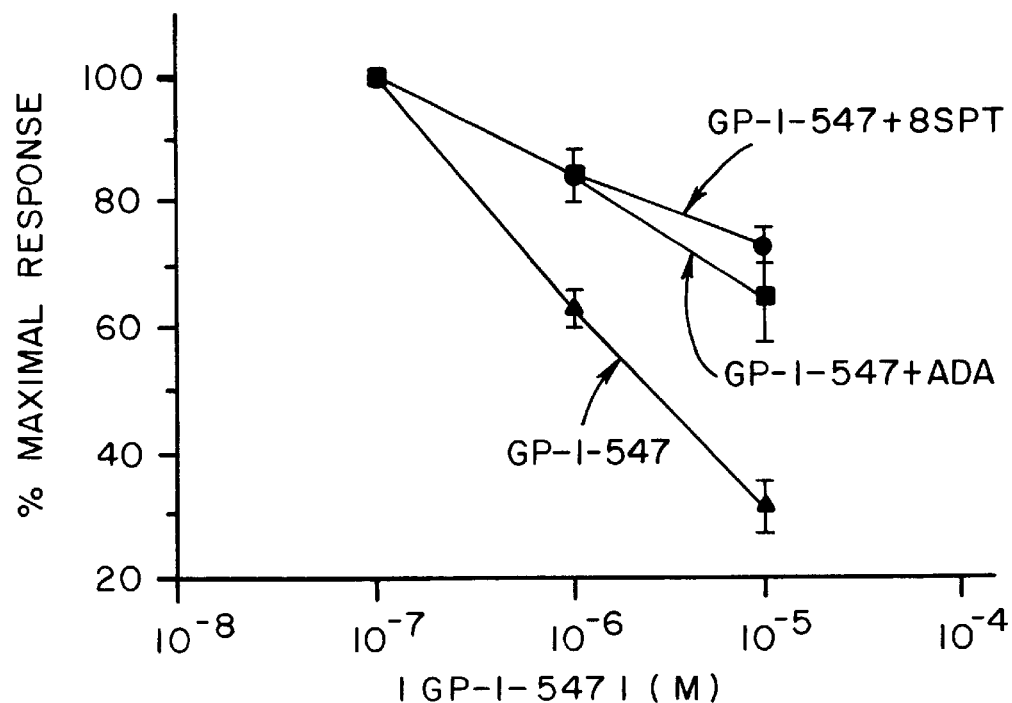

Inhibition of contraction by (A) GP-1-515 and (B) GP-1-547 together with reversal by both 8SPT and ADA are shown in FIGS. 3A and 3B, respectively.

EXAMPLE I

INHIBITION OF SEIZURES BY ADENOSINE KINASE INHIBITORS

The ability of selected adenosine kinase inhibitors to influence PTZ-induced seizures was evaluated in an experimental animal model.

Male Swiss Webster mice in groups of 6–8 were preinjected intraperitoneally (IP) with either vehicle or an adenosine kinase inhibitor followed 1 hour later by 100 mg/kg pentylenetetrazol (PTZ) administered subcutaneously in the upper back of the animal. After injections of the convulsant, animals were isolated in separate cages and observed for the onset of seizure. Animals were scored as being fully protected from seizure if they failed to seize for a period of 1 hour after PTZ administration (vehicle control animals seized after about 4 minutes). The results are shown in FIGS. 4A and 4B.

In FIG. 4A, the adenosine kinase inhibitor, GP-1-456, was administered IP at doses of 1, 5 and 10 mg/kg followed after 45 minutes by PTZ administration.

In FIG. 4B, GP-1-456 was administered IP at a dose of 2.5 mg/kg alone or together with either 34 mg/kg of theophylline or 70 mg/kg of 8-sulfophenyltheophylline followed after 45 minutes by PTZ administration.

In additional studies, mice were given GP-1-456 or GP-1-560 by oral administration 45 minutes prior to PTZ administration. The results are given in Table D and demonstrate that the adenosine kinase inhibitors exhibit oral anticonvulsant activity.

The ability of the adenosine kinase inhibitors to influence electroshock-induced seizures was also evaluated in an experimental model.

The adenosine kinase inhibitor GP-1-456 or vehicle were administered orally to rats prior to electroshock treatment. After 1 hour, corneal electrodes were applied to the eyes of each animal and an electrical stimulus of 160 mA delivered for 0.2 seconds. Animals were isolated in separate cages and observed for seizure. Abolition of the hindleg tonic extensor component is taken as the end point for this test and reflects ability of the compound to prevent seizure spread.

From the data presented in Table E, an $ED_{50}$ of 0.18 mg/kg was determined for protection of electroshock-induced seizures by the adenosine kinase inhibitor, GP-1-456.

TABLE D

| Treatment | N= | Percent Seizure | Seizure Score | Latency To First Seizure (minutes) |
|---|---|---|---|---|
| Control | 13 | 100 | 3.6 ± 1.2 | 3.3 |
| GP-1-456 (2.5 mg/kg) | 13 | 15 | 0.3 ± 0.4* | 8.2* |
| Control | 8 | 100 | 2.5 ± 1.6 | 4.5 |
| GP-1-560 (30 mg/kg) | 7 | 71 | 0.71 ± 0.5 | 4.5 |
| GP-1-560 (50 mg/kg) | 7 | 43 | 1.0 ± 0.9 | 7.0* |

*$p < 0.05$ vs. Control
Data is presented as the mean ± standard deviation.

TABLE E

| GP-1-456 (mg/kg) | No. of Animals (protected/tested) |
|---|---|
| 0.00 | 0/8 |
| 0.05 | 1/8 |
| 0.10 | 2/8 |
| 0.15 | 2/8 |
| 0.19 | 6/8 |
| 0.38 | 6/8 |
| 0.75 | 7/8 |
| 1.50 | 8/8 |

We claim:
1. A compound of the formula:

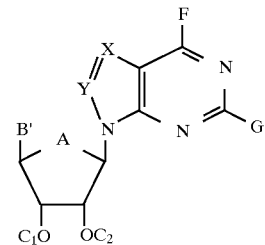

wherein
(a) A is oxygen;
(b) B' is —$(CH_2)_n$-B wherein n is 1, 2, 3, or 4 and B is hydrogen, hydroxy alkyl, alkoxy, amino, alkylamino, acylamino, hydrocarbyloxycarbonylamino, mercapro, alkylthio, azido, cyano, halogen, or B' is alkenyl or alkynyl;
(c) $C_1$ and $C_2$ are each independently hydrogen, acyl, hydrocarbyloxycarbonyl or taken together form a 5-membered ring wherein $C_1$ is a single bond to $C_2$ and $C_2$ is carbonyl or α-alkoxyalkylidene;
(d) X is

and Y is —N= or

(e) D is hydrogen, halogen, alkyl, aryl, aralkyl, alkenyl, alkynyl, haloalkyl, cyano, cyanoalkyl, acyl, carboxamido, a carboxylic acid or carboxylic acid ester group, alkoxy, aryloxy, aralkyloxy, alkyldlio, aryltbio, aralkyltio, amino, alkylamino, aryamino, aralkylanino, acylamino, or nitro;

(f) E is hydrogen, halogen, alkyl, or alkylthio;

(g) F is all, aryl, aralkyl, halogen, amino, alkylthio, arylamino, aralkylamino, cyano, cyanoalkyl, alkoxy, aryloxy, aralkoxy, alkylthio, arylthio, aralkylthio; optionally substituted indolinyl or indolyl; pyrrolidinyl or piperazinyl; and (h) G is hydrogen, halogen, lower alkyl, lower alkoxy, lower alkylamino or lower alkylthio; and pharmaceutically acceptable salts thereof; with the proviso that: when (i) X is

and Y is

then if B' is methyl, D is halogen, cyano or carboxamido, and F is amino, then G is not hydrogen; or if D is hydrogen, then F is not ammo; or (ii) X is

and Y is —N═, if B is hydrogen or halogen, and D and G are hydrogen, then F is not amino.

2. A compound according to claim 1 wherein D is hydrogen, halogen, alkyl, aryl, aralkyl, alkenyl, alkynyl, cyano, cyanoalkyl, alkoxy, aryloxy, aralkoxy, alkylthio, arylthio, aralkylthio, amino, alkylamino, arylamino, aralkylamino, amido, hydrocarbyloxycarbonyl; and E is hydrogen, halogen, alkyl, alkylamino, azido or alkylthio.

3. A compound according to claim 2 wherein B' is —(CH$_2$)$_n$B wherein B is hydrogen, halogen, alkyl, amino, alkylamino, alkoxy, mercapto; alkylthio, azido or cyano.

4. A compound according to claim 3 wherein G is hydrogen, halogen, lower alkyl or lower alkylthio.

5. A compound according to claim 4 wherein G is hydrogen, halogen, alkyl or alkylthio.

6. A compound according to claim 5 wherein G is hydrogen.

7. A compound according to claim 6 wherein E is hydrogen.

8. A compound according to claim 7 wherein F is halogen, amino, alkylamino, arylamino, aralkylamino, alkylthio, arylthio, alkyl, aryl or aralkyl.

9. A compound according to claim 8 wherein D is halogen or aryl.

10. A compound according to claim 7 wherein D is halogen or aryl.

11. A compound according to claim 7 wherein Y is —N═.

12. A compound according to claim 11 wherein B is hydrogen, halogen, lower alkyl, amino, lower alkylamino, azido or cyano.

13. A compound according to claim 11 wherein D is hydrogen, halogen, alkyl, aryl, aralkyl, cyano, alkoxy, aryloxy, aralkoxy, alkenyl, or alkynyl.

14. A compound according to claim 11 wherein B is hydrogen, halogen, lower alkyl, amino, lower alkylamino, lower alkoxy, lower alkylthio, azido, or cyano; and D is hydrogen, halogen, aryl, cyano, alkoxy or aryloxy.

15. A compound according to claim 14 wherein D is hydrogen, halogen or aryl.

16. A compound according to claim 15 wherein B is hydrogen, amino or azido.

17. A compound according to claim 15 wherein F is halogen, amino, alkylamino, arylamino, aralkylamino, alkylthio, arylthio, alkyl, aryl or aralkyl.

18. A compound according to claim 15 wherein B is hydrogen, amino or azido and F is halogen, amino, alkylamino, arylamino, aralkylamino, alkylthio, arylthio, alkyl, aryl or aralkyl and n is 1.

19. A compound according to claim 18 wherein B is amino, D is bromo, F is amino, and C$_1$ and C$_2$ are both hydrogen or acetyl.

20. A compound according to claim 18 wherein B is amino, D is iodo, F is amino and C$_1$ and C$_2$ are both hydrogen.

21. A compound according to claim 18 wherein B is hydrogen, D is iodo, F is amino and C$_1$ and C$_2$ are both hydrogen.

22. A compound according to claim 18 wherein B is hydrogen, D is phenyl, F is anilino and C$_1$ and C$_2$ are both hydrogen.

23. A compound according to claim 18 wherein B is azido, D is p-methoxyphenyl, F is amino and C$_1$ and C$_2$ are both hydrogen.

24. A compound according to claim 18 wherein B is azido, D is phenyl, F is anilino and C$_1$ and C$_2$ are both hydrogen.

25. A compound according to claim 18 wherein D is aryl.

26. A compound according to claim 1 wherein Y is —N═, B' is —(CH$_2$)$_n$-B wherein B is hydrogen, amino or azido; D is halogen or aryl, F is amino, arylamino, alkyl or aralkyl; G is hydrogen; and C$_1$ and C$_2$ are both hydrogen or acetyl.

27. A compound according to claim 1 wherein Y is —N═, B' is —(CH$_2$)$_n$-B wherein B is hydrogen, amino, or azido; D is halogen or aryl; F is amino or arylamino; G is hydrogen, and C$_1$ and C$_2$ are both hydrogen or acetyl.

28. A compound according to claim 27 wherein D is aryl.

29. A compound according to claim 28 wherein F is arylamino.

30. A compound according to claim 29 wherein D is optionally substituted phenyl.

31. A compound according to claim 7 wherein

32. A compound according to claim 31 wherein B is hydrogen, halogen, lower alkyl, amino, lower alkylamino, azido or cyano.

33. A compound according to claim 31 wherein D is hydrogen, alkyl, aryl, aralkyl, cyano, alkenyl or alkynyl.

34. A compound according to claim 31 wherein E is hydrogen or halogen.

35. A compound according to claim 34 wherein B is hydrogen, halogen, lower alkyl, amino, lower alkylamino, alkoxy, alkylthio, azido or cyano; and D is hydrogen, alkyl, aryl, aralkyl, cyano, alkenyl or alkynyl.

36. A compound according to claim 35 wherein D is hydrogen, halogen or aryl.

37. A compound according to claim 36 wherein B is hydrogen, amino or azido.

38. A compound according to claim 36 wherein F is halogen, amino, alkylamino, arylamino, aralkylamino, alkylthio, arylthio, alkyl, aryl or aralkyl.

39. A compound according to claim 36 wherein B is hydrogen, amino or azido and F is halogen, amino, alkylamino, arylamino, aralkylamino, alkylthio, arylthio, alkyl, aryl or aralkyl, and n is 1.

40. A compound according to claim 39 wherein B is azido, D is bromo, E is hydrogen, F is amino, and $C_1$ and $C_2$ are both hydrogen.

41. A compound according to claim 39 wherein B is hydrogen, D is iodo, E is hydrogen, F is anilino, and $C_1$ and $C_2$ are both hydrogen.

42. A compound according to claim 39 wherein B is hydrogen, D is phenyl, E is hydrogen and F is anilino, and $C_1$ and $C_2$ are both hydrogen.

43. A compound according to claim 39 wherein B is hydrogen, D is phenyl, E is hydrogen, F is amino, and $C_1$ and $C_2$ are both hydrogen.

44. A compound according to claim 39 wherein B is methyl, D is iodo, E is hydrogen, F is amino and $C_1$ and $C_2$ are both hydrogen.

45. A compound according to claim 38 wherein n is 2, B is azido, D is iodo, E is hydrogen, F is amino, and $C_1$ and $C_2$ and both hydrogen.

46. A compound according to claim 2 wherein Y is

B'-is vinyl, D is iodo, E is hydrogen, F is amino, G is hydrogen and $C_1$ and $C_2$ are both hydrogen.

47. A compound according to claim 1 wherein D is halogen or aryl; E is hydrogen or halogen and G is hydrogen.

48. A compound according to claim 43 wherein n is 2, B is hydrogen, D is iodo, E is hydrogen, F is amino and $C_1$ and $C_2$ are both hydrogen.

49. A compound according to claim 38 wherein n is 2, B is azido, D is iodo, E is hydrogen, F is amino and $C_1$ and $C_2$ are both hydrogen.

50. A compound according to claim 2 wherein B' is vinyl, $C_1$ and $C_2$ are both hydrogen, Y is

D is iodo, E is hydrogen, F is amino, and G is hydrogen.

51. A compound according to any of claims 2, 7 or 15 wherein F is alkyl, aryl or aralkyl.

52. A compound of the formula:

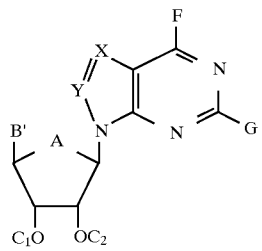

wherein:
(a) A is oxygen;
(b) B' is —(CH$_2$)$_n$-B wherein n is 1, 2, 3, or 4 and B is hydroxy, acyloxy, hydrocarbyloxycarbonyloxy, or —OCONR$_2$ wherein R is independently hydrocarbyl;

(c) $C_1$ and $C_2$ are each independently hydrogen, acyl, hydrocarbyloxycarbonyl or taken together form a 5-membered ring wherein $C_1$ is a single bond to $C_1$ and $C_2$ is carbonyl or α-alkoxyalkylidene;
(d) X is

and Y is

(e) D is halogen, aryl, or aralkyl;
(f) F is alkyl, aryl, aralkyl, halogen, amino, alkylamino, arylamino, aralkylamino, cyano, cyanoalkyl, alkoxy, aryloxy, aralkoxy, alkylthio, arylthio, aralkylthio; optionally substituted indolinyl or indolyl, pyrrolidinyl or piperazinyl; and
(g) G is hydrogen, halogen, lower alkyl, lower alkoxy, or lower alkylthio; ax)d pharmaceutically acceptable salts thereof; with the proviso that when D is halogen, then F is not amino.

53. A compound according to claim 52 wherein G is hydrogen.

54. A compound according to claim 53 wherein D is aryl.

55. A compound according to claim 54 wherein F is halogen, amino, alkylamino, arylamino, aralkylamino, alkylthio, arylthio, alkyl, aryl or aralkyl.

56. A compound according to claim 55 wherein n is 1, B is hydroxy, D is phenyl, F is anilino and $C_1$ and $C_2$ are both hydrogen.

57. A compound of the formula:

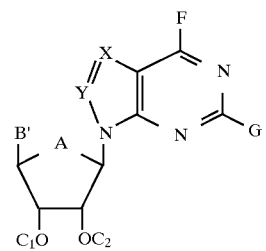

wherein:
(a) A is oxygen;
(b) B' is —(CH$_2$)$_n$-B wherein n is 1, 2, 3, or 4 and B is hydroxy, acyloxy, hydrocarbyloxycarbonyloxy, or —OCONR$_2$ wherein R is hydrocarbyl;
(c) $C_1$ and $C_2$, are each independently hydrogen, acyl, hydrocarbyloxycarbonyl or taken together form a 5-membered ring wherein $C_1$ is a single bond to $C_2$ and $C_2$ is carbonyl or α-alkoxyalkylidene;
(d) X is

and Y is

(e) D is aryl or aralkyl;

(f) E is hydrogen, halogen, alkyl, or alkylio;
(g) F is alkyl, aryl, aralkyl, halogen, amino, alkylamino, arylamino, aralkylamino, cyano, cyanoalkyl, alkoxy, aryloxy, aralkoxy, alkylthio, arylthio, aralkylthio; optionally substituted indolinyl or indolyl, pyrrolidinyl or piperazinyl; and
(g) G is hydrogen, halogen, lower alkyl, lower alkoxy, or lower alkylthio; and pharmaceutically acceptable salts thereof; with the proviso that: when D is oxadiazolyl, triazolyl or triazinyl, and E and G are both hydrogen, then F is not amino.

58. A compound according to claim 57 wherein E is hydrogen or halogen, and G is hydrogen and n is 1 or 2.

59. A compound according to claim 58 wherein D is aryl.

60. A compound according to claim 59 wherein F is halogen, amino, alkylamino, arylamino, aralkylamino, alkylthio, arylthio, alkyl, aryl or aralkyl.

61. A compound according to claim 60 wherein n is 1, B is hydroxy, D is 2-furanyl, E is hydrogen, F is anilino and $C_1$ and $C_2$ are both hydrogen.

62. A compound of the formula:

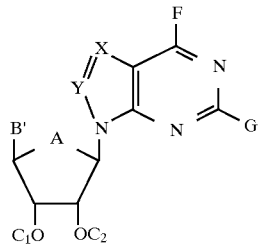

wherein
(a) A is oxygen;
(b) B' is —(CH$_2$)B wherein B is amino, alkylamino, or acylamino;
(c) $C_1$ and $C_2$ are each independently hydrogen, acyl, hydrocarbyloxycarbonyl or taken together form a 5-membered ring wherein $C_1$ is a single bond to $C_2$ and $C_2$ is carbonyl or α-alkoxyalkylidene;
(d) X is —N═ and Y is

(e) E is hydrogen, halogen, alkyl, amino, alkylamino, azido, acylamino, alkoxy or alkylthio;
(f) F is halogen, amino, alkylamino, arylamino, aralkylamino, cyanoalkyl, alkoxy, aryloxy, aralkoxy, alkylthio, arylthio, aralkylthio, alkyl, aryl, aralkyl, optionally substituted indolinyl or indolyl, pyrrolidinyl or piperazinyl; and
(g) G is hydrogen, halogen, lower alkyl, lower alkoxy, or lower alkylthio and pharmaceutical acceptable salts thereof; with the proviso that:
when B is amino or hydrocarbylamino, and E and G are hydrogen, then F is not amino.

63. A compound according to claim 62 wherein G is hydrogen, halogen, lower alkyl or lower alkylthio.

64. A compound according to claim 63 wherein E is halogen, alkyl or alkylthio.

65. A compound according to claim 64 wherein B is amino.

66. A compound according to claim 65 wherein F is halogen, amino, alkylamino, arylamino, aralkylamino, alkylthio, arylthio, alkyl, aryl or aralkyl.

67. A compound according to claim 66 wherein F is amino, arylamino, alkyl, aryl or aralkyl.

68. A compound according to claim 64 wherein B is amino, E is hydrogen or halogen, F is alkyl, aryl or aralkyl, and G is hydrogen.

* * * * *